US008241627B2

(12) United States Patent
Springer et al.

(10) Patent No.: US 8,241,627 B2
(45) Date of Patent: *Aug. 14, 2012

(54) MODIFIED POLYPEPTIDES STABILIZED IN A DESIRED CONFORMATION AND METHODS FOR PRODUCING SAME

(75) Inventors: Timothy A. Springer, Newton, MA (US); Motomu Shimaoka, Brookline, MA (US); Chafen Lu, Newton, MA (US)

(73) Assignee: The Center for Blood Research, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,873

(22) Filed: Jun. 22, 2011

(65) Prior Publication Data

US 2011/0305691 A1 Dec. 15, 2011

Related U.S. Application Data

(62) Division of application No. 12/964,813, filed on Dec. 10, 2010, now Pat. No. 7,968,284, which is a division of application No. 12/592,275, filed on Nov. 20, 2009, now Pat. No. 7,879,577, which is a division of application No. 11/080,043, filed on Mar. 15, 2005, now Pat. No. 7,674,604, which is a division of application No. 09/945,265, filed on Aug. 31, 2001, now Pat. No. 7,160,541.

(60) Provisional application No. 60/229,700, filed on Sep. 1, 2000.

(51) Int. Cl.
*A61K 39/395* (2006.01)

(52) U.S. Cl. ............... 424/130.1; 424/143.1; 424/144.1

(58) Field of Classification Search ........................ None
See application file for complete search history.

(56) References Cited

U.S. PATENT DOCUMENTS

| | | |
|---|---|---|
| 5,284,931 A | 2/1994 | Springer et al. |
| 5,288,854 A | 2/1994 | Diamond et al. |
| 5,395,929 A | 3/1995 | Corbi et al. |
| 5,460,945 A | 10/1995 | Springer et al. |
| 5,475,091 A | 12/1995 | Springer et al. |
| 5,489,533 A | 2/1996 | Springer et al. |
| 5,512,660 A | 4/1996 | Springer et al. |
| 5,514,555 A | 5/1996 | Springer et al. |
| 5,565,550 A | 10/1996 | Springer et al. |
| 5,599,676 A | 2/1997 | Vonderheide et al. |
| 5,612,216 A | 3/1997 | Springer et al. |
| 5,622,700 A | 4/1997 | Jardieu et al. |
| 5,629,162 A | 5/1997 | deFougerolles et al. |
| 5,686,265 A | 11/1997 | Corbi et al. |
| 5,739,032 A | 4/1998 | Springer et al. |
| 5,747,035 A | 5/1998 | Presta et al. |
| 5,821,337 A | 10/1998 | Carter et al. |
| 5,843,712 A | 12/1998 | Levine |
| 5,849,896 A | 12/1998 | Springer et al. |
| 5,869,046 A | 2/1999 | Presta et al. |
| 5,877,295 A | 3/1999 | Diamond et al. |
| 5,891,841 A | 4/1999 | deFougerolles et al. |
| 5,914,112 A | 6/1999 | Bednar et al. |
| 5,948,758 A | 9/1999 | Springer et al. |
| 6,030,947 A | 2/2000 | Corbi et al. |
| 6,037,454 A | 3/2000 | Jardieu et al. |
| 6,096,871 A | 8/2000 | Presta et al. |
| 6,121,022 A | 9/2000 | Presta et al. |
| 6,121,428 A | 9/2000 | Blank et al. |
| 6,358,510 B1 | 3/2002 | Springer et al. |
| 6,413,963 B2 | 7/2002 | Kahn et al. |
| 6,436,403 B1 | 8/2002 | Springer et al. |
| 6,511,664 B1 | 1/2003 | Springer et al. |
| 6,572,856 B1 | 6/2003 | Taylor et al. |
| 6,582,698 B1 | 6/2003 | Dedrick et al. |
| 6,683,158 B2 | 1/2004 | Springer et al. |
| 6,777,191 B1 | 8/2004 | Springer et al. |
| 6,797,270 B1 | 9/2004 | Springer et al. |
| 2001/0031260 A1 | 10/2001 | Lee et al. |
| 2003/0054440 A1 | 3/2003 | Mayo et al. |
| 2004/0120960 A1* | 6/2004 | Jardieu et al. ............... 424/164.1 |

FOREIGN PATENT DOCUMENTS

| | | |
|---|---|---|
| EP | 440351 | 8/1991 |
| WO | WO-94/04188 | 3/1994 |
| WO | WO/98/23761 | * 6/1998 |

OTHER PUBLICATIONS

Carreño et al. 2E8 Binds to the High Affinity I-domain in a Metal Ion-dependent Manner a Second Generation Monoclonal Antibody Selectively Targeting Activated LFA-1. J Biol Chem. Oct. 22, 2010; 285(43): 32860-32868.*
Springer et al. LFA-1, fully human antibody, anti-inflammatory, immune suppression, psoriasis, rheumatoid arthritis, transplant rejection, and ischemia/reperfusion injury. Abstract. 2011 http://www.idi.harvard.edu/uploads/inventions/00-004_06-004_NCS_-_AL-57_Antibody_-_Springer_Motomu.pdf.*
Shimaoka et al. AL-57, a ligand-mimetic antibody to integrin LFA-1, reveals chemokine-induced affinity up-regulation in lymphocytes. Proc Natl Acad Sci U S A. Sep. 19, 2006; 103(38): 13991-13996.*
Huang et al. Identification and characterization of a human monoclonal antagonistic antibody AL-57 that preferentially binds the high-affinity form of lymphocyte function-associated antigen-1. Journal of Leukocyte Biology. 2006;80:905-914.*
The Jin Lab. UAN polymer nanoparticles for targeted delivery of anti-inflammatory drugs. pp. 1-2, Feb. 9, 2012.*

(Continued)

*Primary Examiner* — Maher Haddad
(74) *Attorney, Agent, or Firm* — Rissman Hendricks & Oliverio LLP

(57) ABSTRACT

The present invention provides a method for stabilizing a protein in a desired conformation by introducing at least one disulfide bond into the polypeptide. Computational design is used to identify positions where crysteine residues can be introduced to form a disulfide bond in only one protein conformation, and therefore lock the protein in a given conformation. Accordingly, antibody and small molecule therapeutics are selected that are specific for the desired protein conformation.

The invention also provides modified integrin I-domain polypeptides that are stabilized in a desired conformation. The invention further provides screening assays and therapeutic methods utilizing the modified integrin I-domains of the invention.

8 Claims, 13 Drawing Sheets

OTHER PUBLICATIONS

Kevil et al. Loss of LFA-1, but not Mac-1, Protects MRL/MpJ-Faslpr Mice from Autoimmune Disease. American Journal of Pathology, vol. 165(2):609-616, 2004.*

Connolly MK, Anti-LFA-1 treatment inhibits autoantibody production but does not prolong life in Lupus-prone NZB/NZW mice. American Association of Immunologists. Absract No. 979, 1993.*

"National PBM Drug Monograph Efalizumab", www.vapbm.org, (Feb. 2004),1-25.

Bajt, et al., "Characterization of a Gain of Function Mutation of Integrin Alpha llb beta 3 (platelet glycoprotein llb-lllx)", *J. Biol. Chem*, 267, (1992),22211-22216.

Bost KL, Pascual DW, Antibodies Against a Peptide Sequence within the HIV Envelope Protein Crossreacts with Human Interleukin-2, Immunol. Invest., 17(6-7):577-586, 1988.

Bullard, et al., "A Polygenic Mouse Model of Psoriasiforn Skin Disease in CD18-deficient Mice", *PNAS*, 93, (1996),2116-2121.

Champe, et al., "Monoclonal Antibodies That Block the Activity of Leukocyte Function-associated Antigen I Recognize Three Discrete Epitopes in the Inserted Domain of CAlla", *J. Biol. Chem.*, 270(3), (1995),1388-1394.

Dransfield, et al., "Divalent Cation Regulation of the Function of the Leukocyte Integrin LFA-1", *J. Cell Biol.*, 116, (1992),219-226.

Dransfield, et al., "Interaction of Leukocyte Integrins with Ligand is Necessary but Not Sufficient for Function", *J. Cell. Biol.*, 116, (1992),1527-1535.

Huang, et al., "A Binding Interface on the I Domaine of Lymphocyte Function-associated Antigen-I (LFA-1) Required for Specific Interaction with Intercellular Adhesion Molecule I (ICAM-1)", *J. Biol. Chem.*, 270, (1995),19008-19016.

Huang, et al., "Folding of the Beta-Propeller Domain of the Integrin AlphaL Subunit is Independent of the I Domain and Dependent on the Beta2 Subunit", *Proc. Natl. Acad. Sci. USA*, 94(7), (1997),3162-3167.

Keizer, et al., "A Monoclonal Antibody (NKI-L16) Directed Against a Unique Epitope on the x-chain of Human Leukocyte Function Associated Antigen I . . . ", *J. Immunol.*, 140, (1988),1393.

Kooyk, et al., "Activation of LFA-1 Through the Ca2+-Dependent Epitope Stimulates Lymphocyte Adhesion", *J. Cell Biol.*, 112, (1991),345-354.

Landis, et al., "A Novel LFA-1 Activation Epitope Maps to the I Domain", *J. Cell Biol.*, 120, (1993),1519-1527

Landis, et al., "Involvement of the "I" Domain of the LFA-1 in Selective Binding to Ligands ICAM-1 and ICAM-3", *J. Cell. Biol.*, 126, (1994),529-537.

Larson, et al., "Primary Structure of the Leukocyte Function-associated Molecule 1xSubunit: An Integrin with an Embedded Domain Defining a Protein Superfamily", *J. Cell. Biol.*, 108, (1989),703-712.

Lu, et al., "Locking in Alternate Conformations of the Integrin AlphaLbeta2 I Domain with Disulfide Bonds Reveals Functional Relationships Among Integrin Domains", *Proc. Natl. Acad. Sci. USA*, 98(5), (2001),2393-2398

Owens RJ, Young RJ, "The Genetic Engineering of Monoclonal Antibodies", *J. Immunol Methods*, 168(2), (1994),149-165.

Oxvig, et al., "Conformational Changes in Tertiary Structure Near the Ligand Binding Site of an Integrin I Domain", *PNAS*, 96, (1999),2215-2200.

Qu, et al., "Crystal Structure of the I-Domain from the CD11a/CD18 (LFA-1, xb2) Integin", *PNAS*, 92, (1995),10277-10281.

Salas, et al., "Transition from Rolling to Firm Adhesion is Regulated by the Conformation of the I Domain of the Integrin Lymphocyte Function-associated Antigen-1", *J. Biol. Chem*, 277(52), (2002),50255-50262.

* cited by examiner

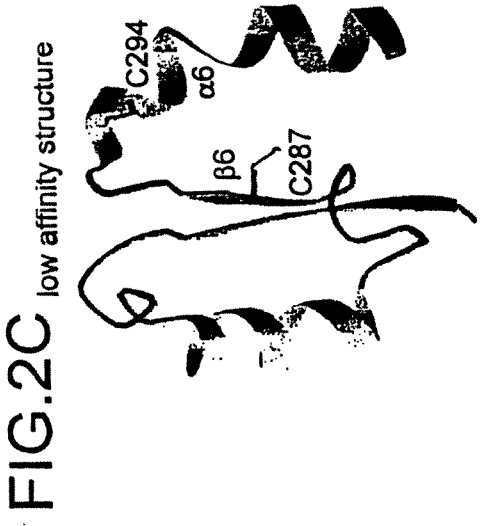
FIG.2A high affinity model
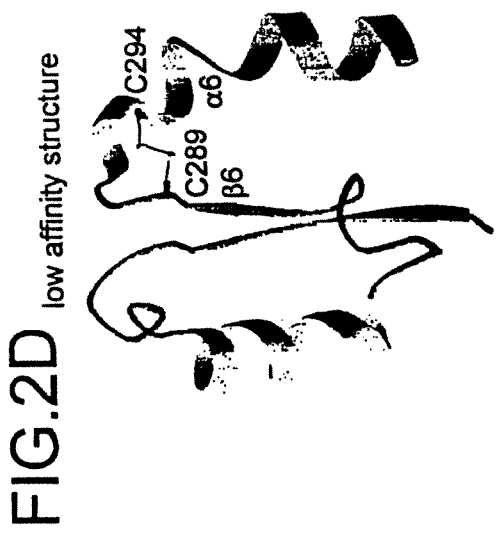
FIG.2C low affinity structure
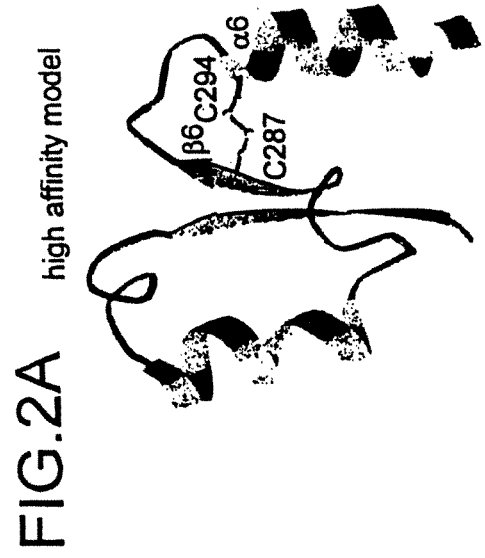
FIG.2B high affinity model
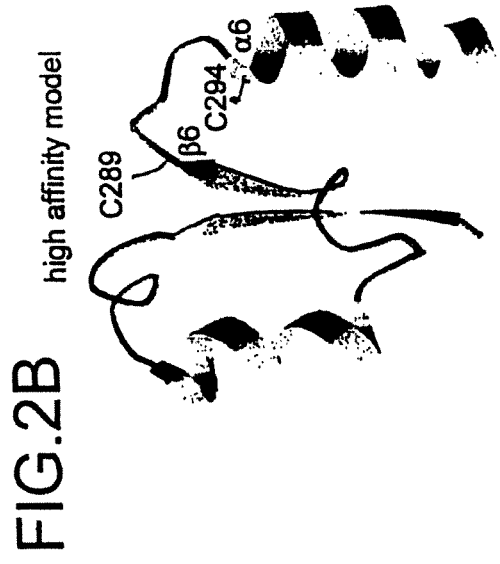
FIG.2D low affinity structure

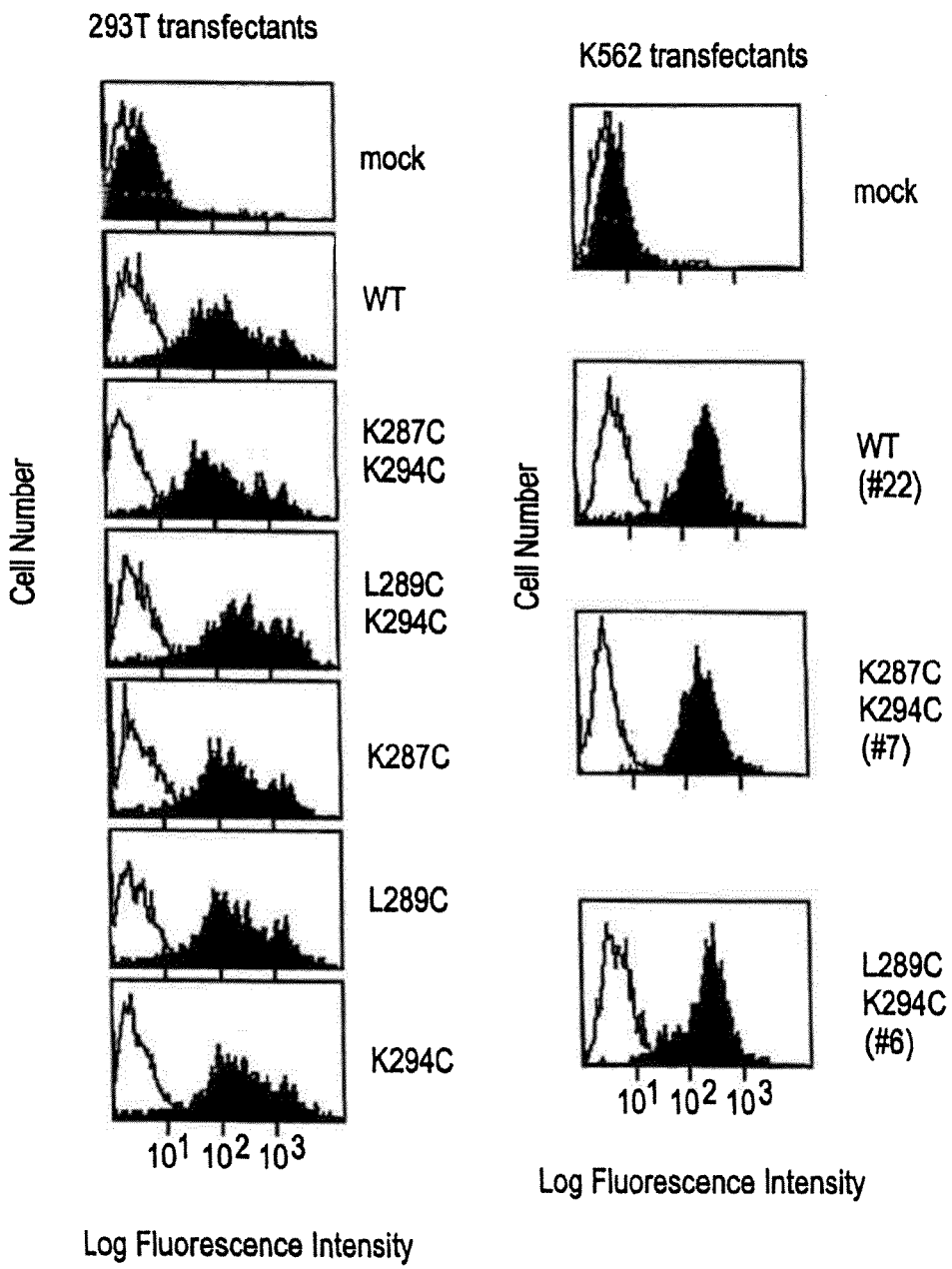

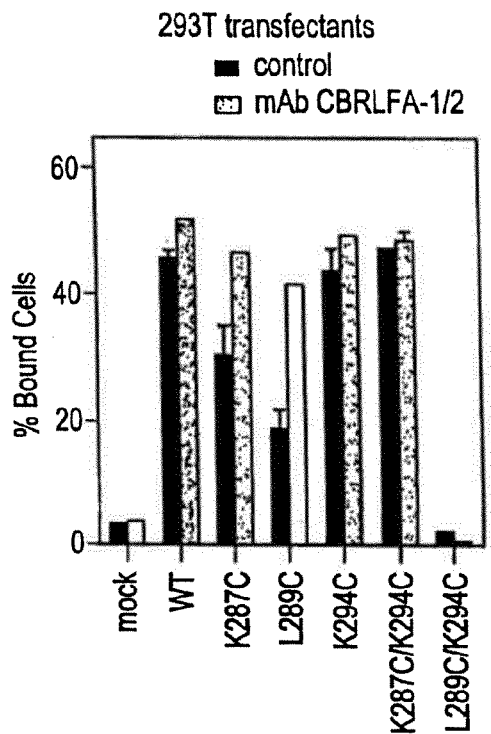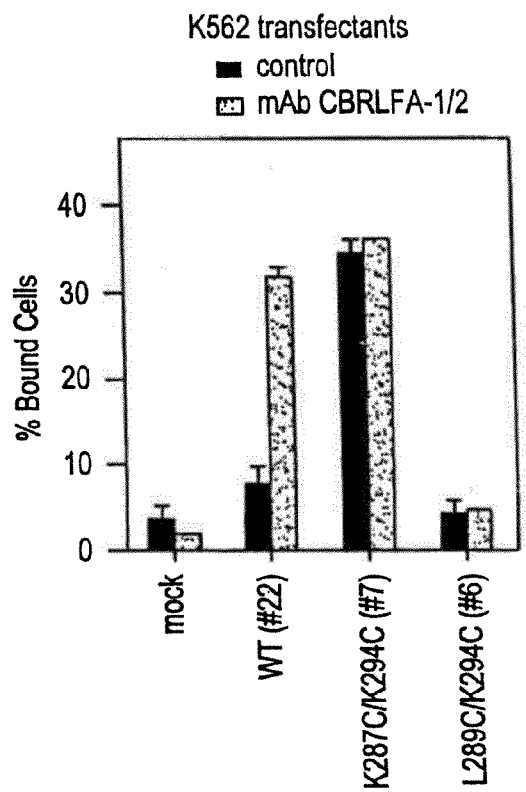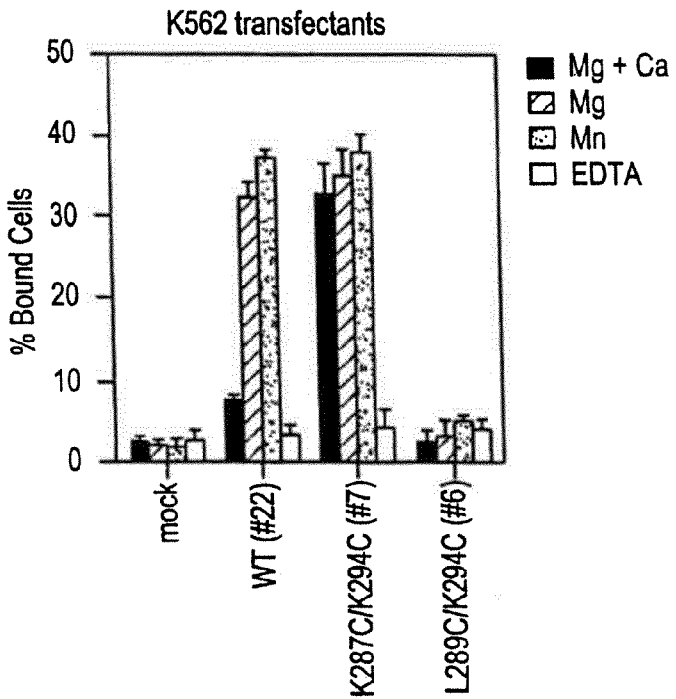

ICAM-1

ICAM-2

SEQUENCE LISTING

<160> NUMBER OF SEQ ID NOS: 5

<210> SEQ ID NO 1
<211> LENGTH: 5133
<212> TYPE: DNA
<213> ORGANISM: Homo sapiens

<400> SEQUENCE: 1

| | | | | | | |
|---|---|---|---|---|---|---|
| cctctttcac | cctgtctagg | ttgccagcaa | atcccacggg | cctcctgacg | ctgcccctgg | 60 |
| ggccacaggt | ccctcgagtg | ctggaaggat | gaaggattcc | tgcatcactg | tgatggccat | 120 |
| ggcgctgctg | tctgggttct | ttttcttcgc | gccggcctcg | agctacaacc | tggacgtgcg | 180 |
| gggcgcgcgg | agcttctccc | caccgcgcgc | cgggaggcac | tttggatacc | gcgtcctgca | 240 |
| ggtcggaaac | ggggtcatcg | tgggagctcc | aggggagggg | aacagcacag | gaagcctcta | 300 |
| tcagtgccag | tcgggcacag | gacactgcct | gccagtcacc | ctgagaggtt | ccaactatac | 360 |
| ctccaagtac | ttgggaatga | ccttggcaac | agacccacaa | gatggaagca | ttttggcctg | 420 |
| tgaccctggg | ctgtctcgaa | cgtgtgacca | gaacacctat | ctgagtggcc | tgtgttacct | 480 |
| cttccgccag | aatctgcagg | gtcccatgct | gcagggcgcg | cctggttttc | aggaatgtat | 540 |
| caagggcaac | gtagacctgg | tatttctgtt | tgatggttcg | atgagcttgc | agccagatga | 600 |
| atttcagaaa | attctggact | tcatgaagga | tgtgatgaag | aaactcagca | cacttcgta | 660 |
| ccagtttgct | gctgttcagt | tttccacaag | ctacaaaaca | gaatttgatt | tctcagatta | 720 |
| tgttaaatgg | aaggaccctg | atgctctgct | gaagcatgta | aagcacatgt | tgctgttgac | 780 |
| caataccttt | ggtgccatca | ttatgtcgc | gacagaggtg | ttccgggagg | agctgggggc | 840 |
| ccggccagat | gccaccaaag | tgcttatcat | catcacggat | ggggaggcca | ctgacagtgg | 900 |
| caacatcgat | gcggccaaag | acatcatccg | ctacatcatc | gggattggaa | agcattttca | 960 |
| gaccaaggag | agtcaggaga | ccctccacaa | atttgcatca | aaacccgcga | gcgagtttgt | 1020 |
| gaaaattctg | gacacatttg | agaagctgaa | agatctattc | actgagctgc | agaagaagat | 1080 |
| ctatgtcatt | gagggcacaa | gcaaacagga | cctgacttcc | ttcaacatgg | agctgtcctc | 1140 |
| cagcggcatc | agtgctgacc | tcagcagggg | ccatgcagtc | gtgggggcag | taggagccaa | 1200 |
| ggactgggct | gggggctttc | ttgacctgaa | ggcagacctg | caggatgaca | catttattgg | 1260 |
| gaatgaacca | ttgacaccag | aagtgagagc | aggctatttg | ggttacaccg | tgacctggct | 1320 |
| gccctcccgg | caaagacctt | cgttgctggc | ctcgggagcc | cctcgatacc | agcacatggg | 1380 |
| ccgagtgctg | ctgttccaag | agccacaggg | cggaggacac | tggagccagg | tccagacaat | 1440 |
| ccatgggacc | cagattggct | cttatttcgg | tggggagctg | tgtggcgtcg | acgtggacca | 1500 |
| agatggggag | acagagctgc | tgctgattgg | tgccccactg | ttctatgggg | agcagagagg | 1560 |
| aggccgggtg | tttatctacc | agagaagaca | gttgggggttt | gaagaagtct | cagagctgca | 1620 |
| gggggacccc | ggctacccac | tcgggcggtt | tggagaagcc | atcactgctc | tgacagacat | 1680 |
| caacggcgat | gggctggtag | acgtggcctgt | gggggcccct | ctggaggagc | aggggctgt | 1740 |
| gtacatcttc | aatgggaggc | acgggggggct | tagtccccag | ccaagtcagc | ggatagaagg | 1800 |
| gacccaagtg | ctctcaggaa | ttcagtggtt | tggacgctcc | atccatgggg | tgaaggacct | 1860 |
| tgaaggggat | ggcttggcag | atgtggctgt | gggggctgag | agccagatga | tcgtgctgag | 1920 |
| ctccggccc | gtggtggata | tggtcaccct | gatgtcctc | tctccagctg | agatcccagt | 1980 |
| gcatgaagtg | gagtgctcct | attcaaccag | taacaagatg | aaagaaggag | ttaatatcac | 2040 |

-continued

```
aatctgtttc cagatcaagt ctctctaccc ccagttccaa ggccgcctgg ttgccaatct    2100
cacttacact ctgcagctgg atggccaccg gaccagaaga cggggggttgt tcccaggagg    2160 gagacatgaa ctcagaagga atatagctgt caccaccagc atgtcatgca ctgacttctc    2220
atttcatttc ccggtatgtg ttcaagacct catctccccc atcaatgttt ccctgaattt    2280
ctctctttgg gaggaggaag ggacaccgag ggaccaaagg gcgcagggca aggacatacc    2340
gcccatcctg agaccctccc tgcactcgga aacctgggag atccctttttg agaagaactg    2400 tggggaggac aagaagtgtg aggcaaactt gagagtgtcc ttctctcctg caagatccag    2460
agccctgcgt ctaactgctt ttgccagcct ctctgtggag ctgagcctga gtaacttgga    2520
agaagatgct tactgggtcc agctggacct gcacttcccc ccgggactct ccttccgcaa    2580
ggtggagatg ctgaagcccc atagccagat acctgtgagc tgcgaggagc ttcctgaaga    2640
gtccaggctt ctgtccaggg cattatcttg caatgtgagc tctcccatct tcaaagcagg    2700
ccactcggtt gctctgcaga tgatgtttaa tacactggta aacagctcct gggggggactc    2760 ggttgaattg cacgccaatg tgacctgtaa caatgaggac tcagacctcc tggaggacaa    2820
ctcagccact accatcatcc ccatcctgta ccccatcaac atcctcatcc aggaccaaga    2880
agactccaca ctctatgtca gtttcacccc caaaggcccc aagatccacc aagtcaagca    2940
catgtaccag gtgaggatcc agccttccat ccacgaccac aacatacccca ccctggaggc    3000 tgtggttggg gtgccacagc ctcccagcga ggggcccatc acacaccagt ggagcgtgca    3060
gatggagcct cccgtgccct gccactatga ggatctggag aggctcccgg atgcagctga    3120
gccttgtctc cccggagccc tgttccgctg ccctgttgtc ttcaggcagg agatcctcgt    3180
ccaagtgatc gggactctgg agctggtggg agagatcgag gcctcttcca tgttcagcct    3240
ctgcagctcc ctctccatct ccttcaacag cagcaagcat ttccacctct atggcagcaa    3300
cgcctccctg gcccaggttg tcatgaaggt tgacgtggtg tatgagaagc agatgctcta    3360
cctctacgtg ctgagcggca tcgggggggct gctgctgctg ctgctcattt tcatagtgct    3420
gtacaaggtt ggtttcttca acggaacct gaaggagaag atggaggctg cagaggtgt    3480 cccgaatgga atccctgcag aagactctga gcagctggca tctgggcaag aggctgggga    3540
tcccggctgc ctgaagcccc tccatgagaa ggactctgag agtggtggtg gcaaggactg    3600
agtccaggcc tgtgaggtgc agagtgccca gaactggact caggatgccc agggccactc    3660
tgcctctgcc tgcattctgc cgtgtgccct cgggcgagtc actgcctctc cctggccctc    3720
agtttcccta tctcgaacat ggaactcatt cctgaatgtc tcctttgcag gctcataggg    3780
aagacctgct gagggaccag ccaagagggc tgcaaaagtg agggcttgtc attaccagac    3840
ggttcaccag cctctcttgg ttccttcctt ggaagagaat gtctgatcta aatgtggaga    3900
aactgtagtc tcaggaccta gggatgttct ggccctcacc cctgccctgg gatgtccaca    3960
gatgcctcca ccccccagaa cctgtccttg cacactcccc tgcactggag tccagtctct    4020
tctgctggca gaaagcaaat gtgacctgtg tcactacgtg actgtggcac acgccttgtt    4080
cttggccaaa gaccaaattc cttggcatgc cttccagcac cctgcaaaat gagaccctcg    4140
tggccttccc cagcctcttc tagagccgtg atgcctccct gttgaagctc tggtgacacc    4200
agcctttctc ccaggccagg ctccttcctg tcttcctgca ttcacccaga cagctccctc    4260
tgcctgaacc ttccatctcg cccaccccctc cttccttgac cagcagatcc cagctcacgt    4320
cacacacttg gttgggtcct cacatctttc acacttccac caccctgcac tactccctca    4380
aagcacacgt catgtttctt catccggcag cctggatgtt ttttcccctgt ttaatgattg    4440
```

-continued

```
acgtacttag cagctatctc tcagtgaact gtgagggtaa aggctatact tgtcttgttc    4500
accttgggat gacgccgcat gatatgtcag ggcgtgggac atctagtagg tgcttgacat    4560
aatttcactg aattaatgac agagccagtg ggaagataca gaaaagagg gccggggctg     4620 ggcgcggtgg ttcacgcctg taatcccagc actttgggag gccaaggagg gtggatcacc    4680
tgaggtcagg agttagaggc cagcctggcg aaaccccatc tctactaaaa atacaaaatc    4740
caggcgtggt ggcacacacc tgtagtccca gctactcagg aggttgaggt aggagaattg    4800
cttgaacctg ggaggtggag gttgcagtga gccaagattg cgccattgca ctccagcctg    4860
ggcaacacag cgagactccg tctcaaggaa aaaataaaaa taaaaagcgg gcacgggccc    4920
ggacatcccc acccttggag gctgtcttct caggctctgc cctgccctag ctccacaccc    4980
tctcccagga cccatcacgc ctgtgcagtg gccccacag aaagactgag ctcaaggtgg     5040
gaaccacgtc tgctaacttg gagccccagt gccaagcaca gtgcctgcat gtatttatcc    5100
aataaatgtg aaattctgtc caaaaaaaaa aaa                                 5133
```

<210> SEQ ID NO 2
<211> LENGTH: 1170
<212> TYPE: PRT
<213> ORGANISM: Homo sapiens

<400> SEQUENCE: 2

```
Met Lys Asp Ser Cys Ile Thr Val Met Ala Met Ala Leu Leu Ser Gly
  1               5                  10                  15

Phe Phe Phe Phe Ala Pro Ala Ser Ser Tyr Asn Leu Asp Val Arg Gly
                 20                  25                  30

Ala Arg Ser Phe Ser Pro Pro Arg Ala Gly Arg His Phe Gly Tyr Arg
             35                  40                  45

Val Leu Gln Val Gly Asn Gly Val Ile Val Gly Ala Pro Gly Glu Gly
         50                  55                  60

Asn Ser Thr Gly Ser Leu Tyr Gln Cys Gln Ser Gly Thr Gly His Cys
 65                  70                  75                  80

Leu Pro Val Thr Leu Arg Gly Ser Asn Tyr Thr Ser Lys Tyr Leu Gly
                 85                  90                  95

Met Thr Leu Ala Thr Asp Pro Thr Asp Gly Ser Ile Leu Ala Cys Asp
            100                 105                 110

Pro Gly Leu Ser Arg Thr Cys Asp Gln Asn Thr Tyr Leu Ser Gly Leu
        115                 120                 125

Cys Tyr Leu Phe Arg Gln Asn Leu Gln Gly Pro Met Leu Gln Gly Arg
    130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Arg Lys Asp Pro Asp Ala Leu Leu Lys His Val
    210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255
```

-continued

```
Lys Val Leu Ile Ile Ile Thr Asp Gly Glu Ala Thr Asp Ser Gly Asn
            260                 265                 270

Ile Asp Ala Ala Lys Asp Ile Arg Tyr Ile Gly Ile Gly Lys
        275                 280                 285

His Phe Gln Thr Lys Glu Ser Gln Glu Thr Leu His Lys Phe Ala Ser
    290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
        355                 360                 365

Gly Ala Lys Asp Trp Ala Gly Gly Phe Leu Asp Leu Lys Ala Asp Leu
    370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
        435                 440                 445

Gln Thr Ile His Gly Thr Gln Ile Gly Ser Tyr Phe Gly Gly Glu Leu
    450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
        515                 520                 525

Thr Asp Ile Asn Gly Asp Gly Leu Val Asp Val Ala Val Gly Ala Pro
    530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
                565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
        595                 600                 605

Val Leu Ser Ser Arg Pro Val Val Asp Met Val Thr Leu Met Ser Phe
    610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
                645                 650                 655

Lys Ser Leu Tyr Pro Gln Phe Gln Gly Arg Leu Val Ala Asn Leu Thr
            660                 665                 670

Tyr Thr Leu Gln Leu Asp Gly His Arg Thr Arg Arg Gly Leu Phe
        675                 680                 685
```

```
Pro Gly Gly Arg His Glu Leu Arg Arg Asn Ile Ala Val Thr Thr Ser
    690                 695                 700
Met Ser Cys Thr Asp Phe Ser Phe His Phe Pro Val Cys Val Gln Asp
705                 710                 715                 720
Leu Ile Ser Pro Ile Asn Val Ser Leu Asn Phe Ser Leu Trp Glu Glu
            725                 730                 735
Glu Gly Thr Pro Arg Asp Gln Arg Ala Gln Gly Lys Asp Ile Pro Pro
            740                 745                 750
Ile Leu Arg Pro Ser Leu His Ser Glu Thr Trp Glu Ile Pro Phe Glu
            755                 760                 765
Lys Asn Cys Gly Glu Asp Lys Lys Cys Glu Ala Asn Leu Arg Val Ser
770                 775                 780
Phe Ser Pro Ala Arg Ser Arg Ala Leu Arg Leu Thr Ala Phe Ala Ser
785                 790                 795                 800
Leu Ser Val Glu Leu Ser Leu Ser Asn Leu Glu Glu Asp Ala Tyr Trp
                805                 810                 815
Val Gln Leu Asp Leu His Phe Pro Pro Gly Leu Ser Phe Arg Lys Val
            820                 825                 830
Glu Met Leu Lys Pro His Ser Gln Ile Pro Val Ser Cys Glu Glu Leu
            835                 840                 845
Pro Glu Glu Ser Arg Leu Leu Ser Arg Ala Leu Ser Cys Asn Val Ser
850                 855                 860
Ser Pro Ile Phe Lys Ala Gly His Ser Val Ala Leu Gln Met Met Phe
865                 870                 875                 880
Asn Thr Leu Val Asn Ser Ser Trp Gly Asp Ser Val Glu Leu His Ala
                885                 890                 895
Asn Val Thr Cys Asn Asn Glu Asp Ser Asp Leu Leu Glu Asp Asn Ser
            900                 905                 910
Ala Thr Thr Ile Ile Pro Ile Leu Tyr Pro Ile Asn Ile Leu Ile Gln
            915                 920                 925
Asp Gln Glu Asp Ser Thr Leu Tyr Val Ser Phe Thr Pro Lys Gly Pro
930                 935                 940
Lys Ile His Gln Val Lys His Met Tyr Gln Val Arg Ile Gln Pro Ser
945                 950                 955                 960
Ile His Asp His Asn Ile Pro Thr Leu Glu Ala Val Val Gly Val Pro
                965                 970                 975
Gln Pro Pro Ser Glu Gly Pro Ile Thr His Gln Trp Ser Val Gln Met
            980                 985                 990
Glu Pro Pro Val Pro Cys His Tyr Glu Asp Leu Glu Arg Leu Pro Asp
            995                 1000                1005
Ala Ala Glu Pro Cys Leu Pro Gly Ala Leu Phe Arg Cys Pro Val Val
    1010                1015                1020
Phe Arg Gln Glu Ile Leu Val Gln Val Ile Gly Thr Leu Glu Leu Val
1025                1030                1035                1040
Gly Glu Ile Glu Ala Ser Ser Met Phe Ser Leu Cys Ser Ser Leu Ser
                1045                1050                1055
Ile Ser Phe Asn Ser Ser Lys His Phe His Leu Tyr Gly Ser Asn Ala
            1060                1065                1070
Ser Leu Ala Gln Val Val Met Lys Val Asp Val Val Tyr Glu Lys Gln
            1075                1080                1085
Met Leu Tyr Leu Tyr Val Leu Ser Gly Ile Gly Gly Leu Leu Leu Leu
            1090                1095                1100
Leu Leu Ile Phe Ile Val Leu Tyr Lys Val Gly Phe Phe Lys Arg Asn
```

```
                1105                1110                1115                1120
Leu Lys Glu Lys Met Glu Ala Gly Arg Gly Val Pro Asn Gly Ile Pro
                    1125                1130                1135

Ala Glu Asp Ser Glu Gln Leu Ala Ser Gly Gln Glu Ala Gly Asp Pro
            1140                1145                1150

Gly Cys Leu Lys Pro Leu His Glu Lys Asp Ser Glu Ser Gly Gly Gly
        1155                1160                1165

Lys Asp
    1170

<210> SEQ ID NO 3
<211> LENGTH: 4740
<212> TYPE: DNA
<213> ORGANISM: Homo sapiens

<400> SEQUENCE: 3
```

| | | | | | |
|---|---|---|---|---|---|
| gaattccgtg | gttcctcagt | ggtgcctgca | acccctggtt | cacctccttc | caggttctgg | 60 |
| ctccttccag | ccatggctct | cagagtcctt | ctgttaacag | ccttgacctt | atgtcatggg | 120 |
| ttcaacttgg | acactgaaaa | cgcaatgacc | ttccaagaga | cgcaaggggg | cttcgggcag | 180 |
| agcgtggtcc | agcttcaggg | atccagggtg | gtggttggag | ccccccagga | gatagtggct | 240 |
| gccaaccaaa | gggcagcct | ctaccagtgc | gactacagca | caggctcatg | cgagcccatc | 300 |
| cgcctgcagg | tccccgtgga | ggccgtgaac | atgtccctgg | gcctgtccct | ggcagccacc | 360 |
| accagccccc | ctcagctgct | ggcctgtggt | cccaccgtgc | accagacttg | cagtgagaac | 420 |
| acgtatgtga | aagggctctg | cttcctgttt | ggatccaacc | tacggcagca | gccccagaag | 480 |
| ttcccagagg | ccctccgagg | gtgtcctcaa | gaggatagtg | acattgcctt | cttgattgat | 540 |
| ggctctggta | gcatcatccc | acatgacttt | cggcggatga | aggagtttgt | ctcaactgtg | 600 |
| atggagcaat | aaaaaagtc | caaaaccttg | ttctctttga | tgcagtactc | tgaagaattc | 660 |
| cggattcact | ttaccttcaa | agagttccag | aacaacccta | acccaagatc | actggtgaag | 720 |
| ccaataacgc | agctgcttgg | gcggacacac | acgccacgg | gcatccgcaa | agtggtacga | 780 |
| gagctgttta | acatcaccaa | cggagcccga | agaatgcct | taagatcct | agttgtcatc | 840 |
| acggatggag | aaaagtttgg | cgatcccttg | ggatatgagg | atgtcatccc | tgaggcagac | 900 |
| agagagggag | tcattcgcta | cgtcattggg | gtggagatgg | ccttccgcag | tgagaaatcc | 960 |
| cgccaagagc | ttaataccat | cgcatccaag | ccgcctcgtg | atcacgtgtt | ccaggtgaat | 1020 |
| aactttgagg | ctctgaagac | cattcagaac | cagcttcggg | agaagatctt | tgcgatcgag | 1080 |
| ggtactcaga | caggaagtag | cagctccttt | gagcatgaga | tgtctcagga | aggcttcagc | 1140 |
| gctgccatca | cctctaatgg | ccccttgctg | agcactgtgg | ggagctatga | ctgggctggt | 1200 |
| ggagtctttc | tatatacatc | aaaggagaaa | agcaccttca | tcaacatgac | cagagtggat | 1260 |
| tcagacatga | atgatgctta | cttgggttat | gctgccgcca | tcatcttacg | gaaccggggt | 1320 |
| caaagcctgg | ttctgggggc | acctcgatat | cagcacatcg | gcctggtagc | gatgttcagg | 1380 |
| cagaacactg | gcatgtggga | gtccaacgct | aatgtcaagg | gcacccagat | cggcgcctac | 1440 |
| ttcgggccct | ccctctgctc | cgtggacgtg | gacagcaacg | gcagcaccga | cctggtcctc | 1500 |
| atcgggcccc | ccattacta | cgagcagacc | cgaggggggcc | aggtgtccgt | gtgcccttg | 1560 |
| cccaggggc | agagggctcg | gtggcagtgt | gatgctgttc | tctacgggga | gcagggccaa | 1620 |
| ccctggggcc | gctttgggc | agccctaaca | gtgctggggg | acgtaaatgg | ggacaagctg | 1680 |
| acggacgtgg | ccattgggc | cccaggagag | gaggacaacc | ggggtgctgt | ttacctgttt | 1740 |

```
cacggaacct caggatctgg catcagcccc tcccatagcc agcggatagc aggctccaag    1800
ctctctccca ggctccagta ttttggtcag tcactgagtg ggggccagga cctcacaatg    1860
gatggactgg tagacctgac tgtaggagcc caggggcacg tgctgctgct caggtcccag    1920
ccagtactga gagtcaaggc aatcatggag ttcaatccca gggaagtggc aaggaatgta    1980
tttgagtgta atgatcaggt ggtgaaaggc aaggaagccg agaggtcag agtctgcctc     2040 catgtccaga gagcacacg ggatcggcta agagaaggac agatccagag tgttgtgact     2100
tatgacctgg ctctggactc cggccgccca cattcccgcg ccgtcttcaa tgagacaaag    2160
aacagcacac gcagacagac acaggtcttg ggctgaccc agacttgtga ccctgaaa      2220 ctacagttgc cgaattgcat cgaggaccca gtgagcccca ttgtgctgcg cctgaacttc    2280
tctctggtgg aacgccatt gtctgctttc gggaacctcc ggccagtgct ggcggaggat     2340
gctcagagac tcttcacagc cttgtttccc tttgagaaga attgtggcaa tgacaacatc    2400
tgccaggatg acctcagcat caccttcagt ttcatgagcc tggactgcct cgtggtgggt    2460
gggccccggg agttcaacgt gacagtgact gtgagaaatg atggtgagga ctcctacagg    2520
acacaggtca ccttcttctt cccgcttgac ctgtcctacc ggaaggtgtc cacactccag    2580
aaccagcgct cacagcgatc ctggcgcctg gcctgtgagt ctgcctcctc caccgaagtg    2640
tctggggcct tgaagagcac cagctgcagc ataaaccacc ccatcttccc ggaaaactca    2700
gaggtcacct ttaatatcac gtttgatgta gactctaagg cttcccttgg aaacaaactg    2760
ctcctcaagg ccaatgtgac cagtgagaac aacatgccca gaaccaacaa aaccgaattc    2820
caactggagc tgccggtgaa atatgctgtc tacatggtgg tcaccagcca tgggggtctcc   2880 actaaatatc tcaacttcac ggcctcagag aataccagtc gggtcatgca gcatcaatat    2940
caggtcagca acctggggca gaggagcctc cccatcagcc tggtgttctt ggtgcccgtc    3000
cggctgaacc agactgtcat atgggaccgc ccccaggtca ccttctccga aacctctcg    3060 agtacgtgcc acaccaagga gcgcttgccc tctcactccg actttctggc tgagcttcgg    3120
aaggcccccg tggtgaactg ctccatcgct gtctgccaga gaatccagtg tgacatcccg    3180
ttctttggca tccaggaaga attcaatgct accctcaaag gcaacctctc gtttgactgg    3240
tacatcaaga cctcgcataa ccacctcctg atcgtgagca cagctgagat cttgtttaac    3300
gattccgtgt tcaccctgct gccgggacag ggggcgtttg tgaggtccca gacggagacc    3360
aaagtggagc cgttcgaggt ccccaacccc ctgccgctca tcgtgggcag ctctgtcggg    3420
ggactgctgc tcctggccct catcaccgcc gcgctgtaca agctcggctt cttcaagcgg    3480
caatacaagg acatgatgag tgaagggggt ccccccgggg ccgaacccca gtagcggctc    3540
cttcccgaca gagctgcctc tcggtggcca gcaggactct gcccagacca cacgtagccc    3600
ccaggctgct ggacacgtcg gacagcgaag tatccccgac aggacgggct ggggcttcca    3660
tttgtgtgtg tgcaagtgtg tatgtgcgtg tgtgcgagtg tgtgcaagtg tctgtgtgca    3720
agtgtgtgca cgtgtgcgtg tgcgtgcatg tgcactcgca cgcccatgtg tgagtgtgtg    3780
caagtatgtg agtgtgtcca gtgtgtgtgc gtgtgtccat gtgtgtgcag tgtgtgcatg    3840
tgtgcgagtg tgtgcatgtg tgtgctcagg ggctgtggct cacgtgtgtg actcagagtg    3900
tctctggcgt gtgggtaggt gacggcagcg tagcctctcc ggcagaaggg aactgcctgg    3960
gctcccttgt gcgtgggtaa gccgctgctg gttttcctc cgggagaggg gacggtcaat     4020
cctgtgggta agagagagg gaaacacagc agcatctctc cactgaaaga agtgggactt    4080
cccgtcgcct gcgagcctgc ggcctgctgg agcctgcgca gcttggatgg atactccatg    4140
```

-continued

```
agaaaagccg tgggtggaac caggagcctc ctccacacca gcgctgatgc ccaataaaga    4200
tgcccactga ggaatcatga agcttccttt ctggattcat ttattatttc aatgtgactt    4260
taattttttg gatggataag cctgtctatg gtacaaaaat cacaaggcat tcaagtgtac    4320
agtgaaaagt ctcccttttcc agatattcaa gtcacctcct taaaggtagt caagattgtg    4380
ttttgaggtt tccttcagac agattccagg cgatgtgcaa gtgtatgcac gtgtgcacac    4440
accacacaca tacacacaca caagcttttt tacacaaatg gtagcatact ttatattggt    4500
ctgtatcttg cttttttttca ccaatatttc tcagacatcg gttcatatta agacataaat    4560 tacttttca ttcttttata ccgctgcata gtattccatt gtgtgagtgt accataatgt    4620
atttaaccag tcttcttttg atatactatt ttcatctctt gttattgcat ctgctgagtt    4680
aataaatcaa atatatgtca aaaaaaaaa aaaaaaaaaa aaaaaaaaa aaaaaaaaa       4740
```

<210> SEQ ID NO 4
<211> LENGTH: 1152
<212> TYPE: PRT
<213> ORGANISM: Homo sapiens

<400> SEQUENCE: 4

```
Met Ala Leu Arg Val Leu Leu Thr Ala Leu Thr Leu Cys His Gly
 1               5                  10                 15

Phe Asn Leu Asp Thr Glu Asn Ala Met Thr Phe Gln Glu Asn Ala Arg
                20                  25                  30

Gly Phe Gly Gln Ser Val Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
```

```
            275                 280                 285
Asp Ala Phe Arg Ser Glu Lys Ser Arg Gln Glu Leu Asn Thr Ile Ala
290                 295                 300
Ser Lys Pro Pro Arg Asp His Val Phe Gln Val Asn Asn Phe Glu Ala
305                 310                 315                 320
Leu Lys Thr Ile Gln Asn Gln Leu Arg Glu Lys Ile Phe Ala Ile Glu
            325                 330                 335
Gly Thr Gln Thr Gly Ser Ser Ser Phe Glu His Glu Met Ser Gln
            340                 345                 350
Glu Gly Phe Ser Ala Ala Ile Thr Ser Asn Gly Pro Leu Leu Ser Thr
            355                 360                 365
Val Gly Ser Tyr Asp Trp Ala Gly Gly Val Phe Leu Tyr Thr Ser Lys
            370                 375                 380
Glu Lys Ser Thr Phe Ile Asn Met Thr Arg Val Asp Ser Asp Met Asn
385                 390                 395                 400
Asp Ala Tyr Leu Gly Tyr Ala Ala Ala Ile Ile Leu Arg Asn Arg Val
                405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
            435                 440                 445
Lys Gly Thr Gln Ile Gly Ala Tyr Phe Gly Ala Ser Leu Cys Ser Val
450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                485                 490                 495
Pro Arg Gly Arg Ala Arg Trp Gln Cys Asp Ala Val Leu Tyr Gly Glu
            500                 505                 510
Gln Gly Gln Pro Trp Gly Arg Phe Gly Ala Ala Leu Thr Val Leu Gly
            515                 520                 525
Asp Val Asn Gly Asp Lys Leu Thr Asp Val Ala Ile Gly Ala Pro Gly
530                 535                 540
Glu Glu Asp Asn Arg Gly Ala Val Tyr Leu Phe His Gly Thr Ser Gly
545                 550                 555                 560
Ser Gly Ile Ser Pro Ser His Ser Gln Arg Ile Ala Gly Ser Lys Leu
                565                 570                 575
Ser Pro Arg Leu Gln Tyr Phe Gly Gln Ser Leu Ser Gly Gly Gln Asp
            580                 585                 590
Leu Thr Met Asp Gly Leu Val Asp Leu Thr Val Gly Ala Gln Gly His
            595                 600                 605
Val Leu Leu Leu Arg Ser Gln Pro Val Leu Arg Val Lys Ala Ile Met
610                 615                 620
Glu Phe Asn Pro Arg Glu Val Ala Arg Asn Val Phe Glu Cys Asn Asp
625                 630                 635                 640
Gln Val Val Lys Gly Lys Glu Ala Gly Glu Val Arg Val Cys Leu His
                645                 650                 655
Val Gln Lys Ser Thr Arg Asp Arg Leu Arg Glu Gly Gln Ile Gln Ser
            660                 665                 670
Val Val Thr Tyr Asp Leu Ala Leu Asp Ser Gly Arg Pro His Ser Arg
            675                 680                 685
Ala Val Phe Asn Glu Thr Lys Asn Ser Thr Arg Arg Gln Thr Gln Val
690                 695                 700
```

-continued

```
Leu Gly Leu Thr Gln Thr Cys Glu Thr Leu Lys Leu Gln Leu Pro Asn
705                 710                 715                 720

Cys Ile Glu Asp Pro Val Ser Pro Ile Val Leu Arg Leu Asn Phe Ser
            725                 730                 735

Leu Val Gly Thr Pro Leu Ser Ala Phe Gly Asn Leu Arg Pro Val Leu
        740                 745                 750

Ala Glu Asp Ala Gln Arg Leu Phe Thr Ala Leu Phe Pro Phe Glu Lys
    755                 760                 765

Asn Cys Gly Asn Asp Asn Ile Cys Gln Asp Asp Leu Ser Ile Thr Phe
770                 775                 780

Ser Phe Met Ser Leu Asp Cys Leu Val Val Gly Gly Pro Arg Glu Phe
785                 790                 795                 800

Asn Val Thr Val Thr Val Arg Asn Asp Gly Glu Asp Ser Tyr Arg Thr
            805                 810                 815

Gln Val Thr Phe Phe Phe Pro Leu Asp Leu Ser Tyr Arg Lys Val Ser
        820                 825                 830

Thr Leu Gln Asn Gln Arg Ser Gln Arg Ser Trp Arg Leu Ala Cys Glu
    835                 840                 845

Ser Ala Ser Ser Thr Glu Val Ser Gly Ala Leu Lys Ser Thr Ser Cys
850                 855                 860

Ser Ile Asn His Pro Ile Phe Pro Glu Asn Ser Glu Val Thr Phe Asn
865                 870                 875                 880

Ile Thr Phe Asp Val Asp Ser Lys Ala Ser Leu Gly Asn Lys Leu Leu
            885                 890                 895

Leu Lys Ala Asn Val Thr Ser Glu Asn Asn Met Pro Arg Thr Asn Lys
        900                 905                 910

Thr Glu Phe Gln Leu Glu Leu Pro Val Lys Tyr Ala Val Tyr Met Val
    915                 920                 925

Val Thr Ser His Gly Val Ser Thr Lys Tyr Leu Asn Phe Thr Ala Ser
930                 935                 940

Glu Asn Thr Ser Arg Val Met Gln His Gln Tyr Gln Val Ser Asn Leu
945                 950                 955                 960

Gly Gln Arg Ser Leu Pro Ile Ser Leu Val Phe Leu Val Pro Val Arg
            965                 970                 975

Leu Asn Gln Thr Val Ile Trp Asp Arg Pro Gln Val Thr Phe Ser Glu
        980                 985                 990

Asn Leu Ser Ser Thr Cys His Thr Lys Glu Arg Leu Pro Ser His Ser
    995                 1000                1005

Asp Phe Leu Ala Glu Leu Arg Lys Ala Pro Val Val Asn Cys Ser Ile
    1010                1015                1020

Ala Val Cys Gln Arg Ile Gln Cys Asp Ile Pro Phe Phe Gly Ile Gln
1025                1030                1035                1040

Glu Glu Phe Asn Ala Thr Leu Lys Gly Asn Leu Ser Phe Asp Trp Tyr
            1045                1050                1055

Ile Lys Thr Ser His Asn His Leu Leu Ile Val Ser Thr Ala Glu Ile
        1060                1065                1070

Leu Phe Asn Asp Ser Val Phe Thr Leu Leu Pro Gly Gln Gly Ala Phe
    1075                1080                1085

Val Arg Ser Gln Thr Glu Thr Lys Val Glu Pro Phe Glu Val Pro Asn
    1090                1095                1100

Pro Leu Pro Leu Ile Val Gly Ser Ser Val Gly Gly Leu Leu Leu Leu
1105                1110                1115                1120

Ala Leu Ile Thr Ala Ala Leu Tyr Lys Leu Gly Phe Phe Lys Arg Gln
            1125                1130                1135
```

```
Tyr Lys Asp Met Met Ser Glu Gly Gly Pro Gly Ala Glu Pro Gln
            1140                1145                1150

<210> SEQ ID NO 5
<211> LENGTH: 1145
<212> TYPE: PRT
<213> ORGANISM: Homo sapiens

<400> SEQUENCE: 5

Tyr Asn Leu Asp Val Arg Gly Ala Arg Ser Phe Ser Pro Arg Ala
 1               5                  10                  15

Gly Arg His Phe Gly Tyr Arg Val Leu Gln Val Gly Asn Gly Val Ile
             20                  25                  30

Val Gly Ala Pro Gly Glu Gly Asn Ser Thr Gly Ser Leu Tyr Gln Cys
             35                  40                  45

Gln Ser Gly Thr Gly His Cys Leu Pro Val Thr Leu Arg Gly Ser Asn
         50                  55                  60

Tyr Thr Ser Lys Tyr Leu Gly Met Thr Leu Ala Thr Asp Pro Thr Asp
 65                  70                  75                  80

Gly Ser Ile Leu Ala Cys Asp Pro Gly Leu Ser Arg Thr Cys Asp Gln
                 85                  90                  95

Asn Thr Tyr Leu Ser Gly Leu Cys Tyr Leu Phe Arg Gln Asn Leu Gln
            100                 105                 110

Gly Pro Met Leu Gln Gly Arg Pro Gly Phe Gln Glu Cys Ile Lys Gly
            115                 120                 125

Asn Val Asp Leu Val Phe Leu Phe Asp Gly Ser Met Ser Leu Gln Pro
130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Arg Lys Asp Pro
            180                 185                 190

Asp Ala Leu Leu Lys His Val Lys His Met Leu Leu Leu Thr Asn Thr
            195                 200                 205

Phe Gly Ala Ile Asn Tyr Val Ala Thr Glu Val Phe Arg Glu Glu Leu
        210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
                245                 250                 255

Tyr Ile Ile Gly Ile Gly Lys His Phe Gln Thr Lys Glu Ser Gln Glu
            260                 265                 270

Thr Leu His Lys Phe Ala Ser Lys Pro Ala Ser Glu Phe Val Lys Ile
        275                 280                 285

Leu Asp Thr Phe Glu Lys Leu Lys Asp Leu Phe Thr Glu Leu Gln Lys
290                 295                 300

Lys Ile Tyr Val Ile Glu Gly Thr Ser Lys Gln Asp Leu Thr Ser Phe
305                 310                 315                 320

Asn Met Glu Leu Ser Ser Ser Gly Ile Ser Ala Asp Leu Ser Arg Gly
                325                 330                 335

His Ala Val Val Gly Ala Val Gly Ala Lys Asp Trp Ala Gly Gly Phe
            340                 345                 350

Leu Asp Leu Lys Ala Asp Leu Gln Asp Asp Thr Phe Ile Gly Asn Glu
        355                 360                 365
```

```
Pro Leu Thr Pro Glu Val Arg Ala Gly Tyr Leu Gly Tyr Thr Val Thr
    370                 375                 380

Trp Leu Pro Ser Arg Gln Lys Thr Ser Leu Leu Ala Ser Gly Ala Pro
385                 390                 395                 400

Arg Tyr Gln His Met Gly Arg Val Leu Leu Phe Gln Glu Pro Gln Gly
            405                 410                 415

Gly Gly His Trp Ser Gln Val Gln Thr Ile His Gly Thr Gln Ile Gly
            420                 425                 430

Ser Tyr Phe Gly Gly Glu Leu Cys Gly Val Asp Val Asp Gln Asp Gly
            435                 440                 445

Glu Thr Glu Leu Leu Leu Ile Gly Ala Pro Leu Phe Tyr Gly Glu Gln
    450                 455                 460

Arg Gly Gly Arg Val Phe Ile Tyr Gln Arg Arg Gln Leu Gly Phe Glu
465                 470                 475                 480

Glu Val Ser Glu Leu Gln Gly Asp Pro Gly Tyr Pro Leu Gly Arg Phe
                485                 490                 495

Gly Glu Ala Ile Thr Ala Leu Thr Asp Ile Asn Gly Asp Gly Leu Val
                500                 505                 510

Asp Val Ala Val Gly Ala Pro Leu Glu Glu Gln Gly Ala Val Tyr Ile
            515                 520                 525

Phe Asn Gly Arg His Gly Gly Leu Ser Pro Gln Pro Ser Gln Arg Ile
    530                 535                 540

Glu Gly Thr Gln Val Leu Ser Gly Ile Gln Trp Phe Gly Arg Ser Ile
545                 550                 555                 560

His Gly Val Lys Asp Leu Glu Gly Asp Gly Leu Ala Asp Val Ala Val
                565                 570                 575

Gly Ala Glu Ser Gln Met Ile Val Leu Ser Ser Arg Pro Val Val Asp
                580                 585                 590

Met Val Thr Leu Met Ser Phe Ser Pro Ala Glu Ile Pro Val His Glu
            595                 600                 605

Val Glu Cys Ser Tyr Ser Thr Ser Asn Lys Met Lys Glu Gly Val Asn
    610                 615                 620

Ile Thr Ile Cys Phe Gln Ile Lys Ser Leu Tyr Pro Gln Phe Gln Gly
625                 630                 635                 640

Arg Leu Val Ala Asn Leu Thr Tyr Thr Leu Gln Leu Asp Gly His Arg
                645                 650                 655

Thr Arg Arg Arg Gly Leu Phe Pro Gly Gly Arg His Glu Leu Arg Arg
                660                 665                 670

Asn Ile Ala Val Thr Thr Ser Met Ser Cys Thr Asp Phe Ser Phe His
            675                 680                 685

Phe Pro Val Cys Val Gln Asp Leu Ile Ser Pro Ile Asn Val Ser Leu
    690                 695                 700

Asn Phe Ser Leu Trp Glu Glu Glu Gly Thr Pro Arg Asp Gln Arg Ala
705                 710                 715                 720

Gln Gly Lys Asp Ile Pro Pro Ile Leu Arg Pro Ser Leu His Ser Glu
                725                 730                 735

Thr Trp Glu Ile Pro Phe Glu Lys Asn Cys Gly Glu Asp Lys Lys Cys
            740                 745                 750

Glu Ala Asn Leu Arg Val Ser Phe Ser Pro Ala Arg Ser Arg Ala Leu
    755                 760                 765

Arg Leu Thr Ala Phe Ala Ser Leu Ser Val Glu Leu Ser Leu Ser Asn
770                 775                 780

Leu Glu Glu Asp Ala Tyr Trp Val Gln Leu Asp Leu His Phe Pro Pro
```

```
                785                 790                 795                 800
Gly Leu Ser Phe Arg Lys Val Glu Met Leu Lys Pro His Ser Gln Ile
                805                 810                 815
Pro Val Ser Cys Glu Leu Pro Glu Ser Arg Leu Leu Ser Arg
                820                 825                 830
Ala Leu Ser Cys Asn Val Ser Pro Ile Phe Lys Ala Gly His Ser
                835                 840                 845
Val Ala Leu Gln Met Met Phe Asn Thr Leu Val Asn Ser Ser Trp Gly
                850                 855                 860
Asp Ser Val Glu Leu His Ala Asn Val Thr Cys Asn Asn Glu Asp Ser
865                 870                 875                 880
Asp Leu Leu Glu Asp Asn Ser Ala Thr Thr Ile Ile Pro Ile Leu Tyr
                885                 890                 895
Pro Ile Asn Ile Leu Ile Gln Asp Gln Glu Asp Ser Thr Leu Tyr Val
                900                 905                 910
Ser Phe Thr Pro Lys Gly Pro Lys Ile His Gln Val Lys His Met Tyr
                915                 920                 925
Gln Val Arg Ile Gln Pro Ser Ile His Asp His Asn Ile Pro Thr Leu
                930                 935                 940
Glu Ala Val Val Gly Val Pro Gln Pro Ser Glu Gly Pro Ile Thr
945                 950                 955                 960
His Gln Trp Ser Val Gln Met Glu Pro Pro Val Pro Cys His Tyr Glu
                965                 970                 975
Asp Leu Glu Arg Leu Pro Asp Ala Ala Glu Pro Cys Leu Pro Gly Ala
                980                 985                 990
Leu Phe Arg Cys Pro Val Val Phe Arg Gln Glu Ile Leu Val Gln Val
                995                 1000                1005
Ile Gly Thr Leu Glu Leu Val Gly Glu Ile Glu Ala Ser Ser Met
    1010                1015                1020
Phe Ser Leu Cys Ser Ser Leu Ser Ile Ser Phe Asn Ser Ser Lys
    1025                1030                1035
His Phe His Leu Tyr Gly Ser Asn Ala Ser Leu Ala Gln Val Val
    1040                1045                1050
Met Lys Val Asp Val Val Tyr Glu Lys Gln Met Leu Tyr Leu Tyr
    1055                1060                1065
Val Leu Ser Gly Ile Gly Gly Leu Leu Leu Leu Leu Leu Ile Phe
    1070                1075                1080
Ile Val Leu Tyr Lys Val Gly Phe Phe Lys Arg Asn Leu Leu Glu
    1085                1090                1095
Lys Met Glu Ala Gly Arg Gly Val Pro Asn Gly Ile Pro Ala Glu
    1100                1105                1110
Asp Ser Glu Gln Leu Ala Ser Gly Gln Glu Ala Gly Asp Pro Gly
    1115                1120                1125
Cys Leu Lys Pro Leu His Glu Lys Asp Ser Glu Ser Gly Gly Gly
    1130                1135                1140
Lys Asp
    1145
```

MODIFIED POLYPEPTIDES STABILIZED IN A DESIRED CONFORMATION AND METHODS FOR PRODUCING SAME

CROSS REFERENCE TO RELATED APPLICATIONS

This application is a divisional of U.S. application Ser. No. 12/964,813, filed Dec. 10, 2010 now U.S. Pat. No. 7,968,284, which is a divisional of U.S. application Ser. No. 12/592,275, filed Nov. 20, 2009 now U.S. Pat. No. 7,879,577, which is a divisional of U.S. application Ser. No. 11/080,043, filed Mar. 15, 2005 now U.S. Pat. No. 7,674,604, which is a divisional of U.S. application Ser. No. 09/945,265, filed Aug. 31, 2001 now U.S. Pat. No. 7,160,541, which claims priority to U.S. provisional Application No. 60/229,700, filed Sep. 1, 2000, all of which are hereby incorporated herein in their entirety by reference.

BACKGROUND OF THE INVENTION

The integrin family of adhesion molecules are noncovalently-associated $\alpha/\beta$ heterodimers. To date, at least fourteen different integrin $\alpha$ subunits and eight different $\beta$ subunits have been reported (Hynes, R O (1992) Cell 69:1-25). Lymphocyte function-associated antigen-1 (LFA-1) is a member of the leukocyte integrin subfamily. Members of the leukocyte integrin subfamily share the common $\beta 2$ subunit (CD 18) but have distinct $\alpha$ subunits, $\alpha L$ (CD11a), $\alpha M$ (CD11b), $\alpha X$ (CD11c) and $\alpha d$ for LFA-1, Mac-1, p150.95 and $\alpha d/\beta 2$, respectively (Springer, T A (1990) Nature 346: 425-433; Larson, R S and Springer T A, (1990) Immunol Rev 114:181-217; Van der Vieren, M et al. (1995) Immunity 3:683-690). The leukocyte integrins mediate a wide range of adhesive interactions that are essential for normal immune and inflammatory responses.

Both integrin $\alpha$ and $\beta$ subunits are type I transmembrane glycoproteins, each with a large extracellular domain, a single transmembrane region and a short cytoplasmic tail. Several structurally distinct domains have been identified or predicted in the $\alpha$ and $\beta$ subunit extracellular domains.

The N-terminal region of the integrin $\alpha$ subunits contains seven repeats of about 60 amino acids each, and has been predicted to fold into a 7-bladed $\beta$-propeller domain (Springer, T A (1997) Proc Natl Acad Sci USA 94:65-72). The leukocyte integrin $\alpha$ subunits, the $\alpha 1$, $\alpha 2$, $\alpha 10$, $\alpha 11$, and $\alpha E$ subunits contain an inserted domain or I-domain of about 200 amino acids (Larson, R S et al. (1989) J Cell Biol 108: 703-712; Takada, Y et al. (1989) EMBO J 8:1361-1368; Briesewitz, R et al. (1993) J Biol Chem 268:2989-2996; Shaw, S K et al. (1994) J Biol Chem 269:6016-6025; Camper, L et al. (1998) J Biol Chem 273:20383-20389). The I-domain is predicted to be inserted between $\beta$-sheets 2 and 3 of the $\beta$-propeller domain. The three dimensional structure of the $\alpha M$, $\alpha L$, $\alpha 1$ and $\alpha 2$ I-domains has been solved and shows that it adopts the dinucleotide-binding fold with a unique divalent cation coordination site designated the metal ion-dependent adhesion site (MIDAS) (Lee, J-O, et al. (1995) Structure 3:1333-1340; Lee, J-O, et al. (199S) Cell 80:631-638; Qu, A and Leahy, D J (1995) Proc Natl Acad Sci USA 92:10277-10281; Qu, A and Leahy, D J (1996) Structure 4:931-942; Emsley, J et al. (1997) J Biol Chem 272:28512-28517; Baldwin, E T et al. (1998) Structure 6:923-935; Kallen, J et al. (1999) J Mol Biol 292:1-9). The C-terminal region of the $\alpha M$ subunit has been predicted to fold into a $\beta$-sandwich structure (Lu, C et al. (1998) J Biol Chem 273:15138-15147).

The integrin $\beta$ subunits contain a conserved domain of about 250 amino acids in the N-terminal portion, and a cysteine-rich region in the C-terminal portion. The $\beta$ conserved domain, or I-like domain, has been predicted to have an "I-domain-like" fold (Puzon-McLaughlin, W and Takada, Y (1996) J Biol Chem 271:20438-20443; Tuckwell, D S and Humphries, M J (1997) FEBS Lett 400: 297-303; Huang, C et al. (2000) J Biol Chem 275:21514-24). The C-terminal Cys-rich region of the $\beta$ subunits appears to be important in the regulation of integrin function, as a number of activating antibodies to the $\beta 1$, $\beta 2$ and $\beta 3$ subunits bind to this region (Petruzzelli, L et al. (1995) J Immunol 155:854-866; Robinson, M K et al. (1992) J Immunol 148:1080-1085; Faull, R J et al. (1996) J Biol Chem 271:25099-25106; Shih, D T et al. (1993) J Cell Biol 122:1361-1371; Du, X et al. (1993) J Biol Chem 268:23087-23092).

Electron microscopic images of integrins reveal that the N-terminal portions of the .alpha. and .beta. subunits fold into a globular head that is connected to the membrane by two rod-like tails about 16 nm long corresponding to the C-terminal portions of the .alpha. and .beta. extracellular domains (Nermut, M V et al. (1988), EMBO J 7:4093-4099; Weisel, J W et al. (1992) J Biol Chem 267:16637-16643; Wippler, J et al. (1994) J Biol Chem 269: 8754-8761).

LFA-1 is expressed on all leukocytes and is the receptor for three Ig superfamily members, intercellular adhesion molecule-1, -2 and -3) (Marlin, S D et al. (1987) Cell 51:813-819; Staunton, D E et al. (1989) Nature 339:61-64; de Fougerolles, et al. (1991) J Exp Med 1 74:253-267). Substantial data indicate that the I-domain of LFA-1 is critical for interaction with ligands. Mutagenesis studies have shown that residues M140, E146, T175, L205, E241, T243, S245 and K263 in the I-domain are important for ligand binding (Huang, C et al. (1995) J Biol Chem 270:19008-19016; Edwards, C P et al. (1998) J Biol Chem 273:28937-28944). These residues are located on the surface of the I-domain surrounding the $Mg^{2+}$ ion, defining a ligand binding interface on the upper surface of the I-domain. The importance of the I-domain in ligand binding is further underscored by mAb blocking studies. A large number mAbs that inhibit LFA-1 interaction with its ligands map to the I-domain (Randi, A M et al. (1994) J Biol Chem 269:12395-12398; Champe, M et al. (1995) J Biol Chem 270:1388-1394; Huang, C et al. (1995) J Biol Chem 270:19008-19016; Edwards, C P et al. (1998) J Biol Chem 273:28937-28944). Two groups have recently shown that I-domain deleted LFA-1 lacks ligand recognition and binding ability, further demonstrating the role of the I-domain in LFA-1 function (Leitinger, B et al. (2000) Mol Biol Cell 11, 677-690; Yalamanchili, P et al. (2000) J Biol Chem 275:21877-82). The I-domains of other I-domain containing integrins have also been implicated in ligand binding (Diamond, M S (1993) J Cell Biol 120:545556; Michishita, M et al. (1993) Cell 72:857-867; Muchowski, P J et al. (1994) J Biol Chem 269:26419-26423; Zhou, L et al. (1994) J Biol Chem 269:17075-17079; Ueda, T et al. (1994) Proc Natl Acad USA 91:10680-10684; Kamata, T et al. (1994) J Biol Chem 269:96599663; Kern, A et al. (1994) J Biol Chem 269:22811-22816).

Binding of LFA-1 to ICAMs requires LFA-1 activation. LFA-1 can be activated by signals from the cytoplasm, called "inside-out" signaling (Diamond, M S et al. (1994) Current Biology 4:506-517). Divalent cations $Mn^{2+}$, $Mg^{2+}$ and $Ca^{2+}$ can directly modulate ligand-binding function of LFA-1 (Dransfield, I et al. (1989) EMBO J 8:3759-3765; Dransfield, I et al. (1992). J Cell Biol 116:219-226; Stewart, M P et al. (1996) J Immunol 156:1810-1817). In addition, LFA-1 can be activated by certain mAbs that bind the extracellular domains of the αL or β2 subunit (Keizer, G D et al. (1988) J Immunol 140:1393-1400; Robinson, M K et al. (1992) J Immunol 148:1080-1085; Andrew, D et al. (1993) Eur J Immunol 23:2217-2222; Petruzzelli, L et al. (1995) J Immunol 155: 854-866). The molecular mechanism for integrin activation is not yet well understood. It has been proposed that intramolecular conformational changes accompanying integrin activation increase integrin affinity for ligand, and this is supported by the existence of antibodies that only recognize activated integrins (Dransfield, I et al. (1989) EMBO J 8:3759-3765; Diamond, M S et al. (1993) J Cell Biol 120: 545-556; Shattil, S J et al. (1985) J Biol Chem 260:11107-11114). One of such antibodies CBRLFA-1/5 binds to the Mac-1 I-domain very close to the ligand binding site (Oxvig, C et al. (1999) Proc Natl Acad USA 96:2215-2220), providing further evidence that the I-domain itself undergoes conformational changes with activation.

Two different crystal forms of the Mac-1 I-domain have been obtained, and it has been hypothesized that the two structures represent the "active" and "inactive" conformation, respectively (Lee, J-O et al. (1995) Structure 3, 1333-1340; Lee, J-O et al. (1995) Cell 80:631-638). In the "active" form, crystallized with $Mg^{2+}$, a glutamate from a neighboring I-domain provides the sixth metal coordination site, while in the "inactive" conformation, complexed with $Mn^{2+}$, a water molecule completes the metal coordination sphere. The change in metal coordination is linked to a large shift of the C-terminal α-helix; in the putative "active" conformation, the C-terminal helix moves 10 .ANG. down the body of the I-domain (Lee, J-O et al. (1995) Structure 3:1333-1340). Results from epitope mapping of mAb CBRM-1/5 that only recognizes activated Mac-1 have suggested that the conformational differences are physiologically (Oxvig, C et al. (1999) Proc Natl Acad Sci USA 96:2215-2220). The crystal and NMR structures of the LFA-1 I-domain have a conformation similar to the putative "inactive" conformation of the Mac-1 I-domain (Qu, A et al. (1995) Proc Natl Acad Sci USA 92:10277-10281; Qu, A (1996) Structure 4: 931-942; Kallen, J et al. (1999) J Mol Biol 292:1-9; Legge, G B et al. (2000) J Mol Biol 295:1251-1264).

In addition to integrins, many pharmaceutically important proteins exist in two alternative three-dimensional structures, referred to as conformations or conformers. Often these proteins have important signaling functions, such as small G proteins, trimeric G protein a subunits, tyrosine kinases, and G protein-coupled receptors. Typically, one of these conformations and not the other is enzymatically active or has effector functions. Therefore, antibody or small molecule therapeutics that are specific for a protein in a particular conformation, for example, the active conformation, would have great advantages over non-selective alternatives.

SUMMARY OF THE INVENTION

Computational design can be used to introduce a disulfide bond into a protein or polypeptide such that the molecule is stabilized in a desired conformation. Accordingly, antibodies, e.g., anti-LFA-1 antibodies, or small molecule therapeutics that are specific for a desired protein conformation, e.g., an "open" or active conformation or a "closed" or inactive conformation can be identified.

The invention pertains to methods for stabilizing a polypeptide, e.g., a polypeptide comprising a functional domain of a protein, in a desired conformation. The method comprises introducing at least one disulfide bond into the polypeptide such that the polypeptide is stabilized in a desired conformation. In a preferred embodiment the disulfide bond is formed by the introduction of at least one cysteine substitution into the amino acid sequence of the polypeptide. In another embodiment, the distance between the Cβ carbons in the disulfide bond is in the range of 3.00-8.09.ANG. In another embodiment, the distance between the Cβ carbons in the disulfide bond is in the range of 3.41-7.08.ANG.

Computational design can be used to introduce a disulfide bond into a protein or polypeptide such that the molecule is stabilized in a desired conformation. Accordingly, antibody or small molecule therapeutics that are specific for a desired protein conformation can be identified.

The method of the invention is widely applicable to a variety of biologically and pharmaceutically important proteins that exist in two different three-dimensional conformations, including an integrin subunit, a small G protein, a heterotrimeric G protein α subunit, a tyrosine kinase, a G protein-coupled receptor, an enzyme under allosteric control, a zymogen, complement C3, complement C4, and fibrinogen. In a preferred embodiment, the polypeptide is an integrin I-domain polypeptide.

In another aspect, the invention provides a modified integrin I-domain polypeptide that is stabilized in a desired conformation by the introduction of at least one disulfide bond. In one embodiment, a modified integrin I-domain is encoded by an amino acid sequence containing at least one cysteine substitution as compared to the wild-type sequence, such that a disulfide bond is formed. In another embodiment, the distance between the Cβ carbons of the residues that are substituted for cysteines is in the range of 3.00-8.09.ANG. In yet another embodiment, the distance between the Cβ carbons in the disulfide bond is in the range of 3.41-7.08.ANG.

In one embodiment, a modified integrin I-domain polypeptide of the invention is derived from an I-domain of an integrin a subunit, for example, α1, α2, α10, α11, αD, αE, αL (CD11a), αM (CD11b), and αX (CD11c). For example, in one embodiment of the invention, a modified integrin I-domain polypeptide is derived from the I-domain of the human αL subunit and contains amino acid substitutions K287C/K294C, E284C/E301C, L161C/F299C, K160C/F299C, L161C/T300C, or L289C/K294C. In another embodiment of the invention, a modified integrin I-domain polypeptide is derived from the I-domain of the human αM subunit and contains amino acid substitutions Q163C/Q309C, D294C/Q311C, or Q163C/R313c.

In a preferred embodiment, a modified integrin I-domain polypeptide of the invention is stabilized in the open conformation. In another embodiment, a modified integrin I-domain polypeptide of the invention is stabilized in the closed conformation. In another embodiment, a modified integrin I-domain binds ligand with high affinity. In yet another embodiment, a modified integrin I-domain polypeptide is operatively linked to a heterologous polypeptide.

In a related aspect, the invention provides isolated nucleic acid molecules which encode a modified integrin I-domain polypeptide of the invention.

The modified integrin I-domain polypeptides, and/or biologically active or antigenic fragments thereof, are useful, for example, as reagents or targets in assays applicable to the treatment and/or diagnosis of integrin-mediated disorders.

Accordingly, in one aspect, the invention provides an antibody, or an antigen binding fragment thereof, which selectively binds to a modified integrin I-domain in the open conformation. In another aspect, the invention provides an antibody, or an antigen binding fragment thereof, which selectively binds to an integrin I-domain polypeptide in the open conformation, an integrin I-domain polypeptide in the closed conformation, or a modified integrin I-domain polypeptide. In one embodiment, the antibody binds to an activation specific epitope on the integrin I-domain. In another embodiment, the antibody blocks an interaction between an integrin and a cognate ligand. In one embodiment, the antibody is an anti-LFA-1 antibody, or an antigen binding fragment thereof, e.g., an anti-LFA-1 antibody which reacts with or binds an open or closed conformation of an LFA-1 polypeptide, or a modified LFA-1 I-domain integrin polypeptide, or fragment thereof.

In another aspect the invention provides a method for identifying a modulator of integrin activity comprising assaying the ability of a test compound to bind to a modified integrin I-domain polypeptide which is stabilized in the open conformation. In another embodiment, the invention provides a method for identifying a compound capable of modulating the interaction of an integrin and a cognate ligand wherein binding of a ligand to a modified integrin I-domain polypeptide which is stabilized in the open conformation is assayed in the presence and absence of a test compound.

In another aspect, the invention provides a composition comprising a modified integrin I-domain polypeptide or an anti-integrin I-domain antibody (or an antigen binding fragment thereof), such composition can further include a pharmaceutically acceptable carrier.

In yet another aspect, the invention pertains to methods for treating or preventing an integrin-mediated disorder (e.g., an inflammatory or autoimmune disorder) in a subject, or for inhibiting the binding of an integrin to a cognate ligand in a subject comprising administering to a subject a therapeutically effective amount of a modified integrin I-domain polypeptide stabilized in the open conformation or an antibody (or antigen binding fragment thereof) which selectively binds to an integrin I-domain in the open conformation. In one embodiment, the antibody is an LFA-1 antibody, or an antigen binding fragment thereof, which specifically reacts with or binds an LFA-1 I-domain in the open conformation or specifically reacts with or binds a modified LFA-1 I-domain polypeptide. In a preferred embodiment, the modified integrin I-domain polypeptide binds ligand with high affinity. In another preferred embodiment, the modified integrin I-domain polypeptide for therapeutic use is a soluble polypeptide, e.g., a fusion protein.

Other features and advantages of the invention will be apparent from the following detailed description and claims.

BRIEF DESCRIPTION OF THE FIGURES

FIG. 2 depicts predicted disulfide bonds that are selective for high affinity or low affinity conformers of the LFA-1 I domain. The K287C/K294C mutation (Panels A, C) and L289C/K294C mutation (Panels B, D) were modeled in both high affinity (Panels A, B) and low affinity (Panels C, D) I domain conformers. Residues 254 to 305 of the models are shown. The four models were superimposed using residues not involved in conformational shifts and were used in exactly the same orientation for figure preparation. Therefore, the downward shift in the α6 helix in panels A and B compared to panels C and D is readily apparent. The remodeling of the loop connecting β6 and α6 is accompanied by a reversal in the orientation of the sidechain of residue 289 (panel B compared to panel D). Prepared with RIBBONS.

FIG. 3 depicts the cell surface expression of LFA-1 cysteine substitution mutants on 293T transient transfectants (Panel A), and K562 stable transfectants (Panel B) as determined by flow cytometric analysis using monoclonal antibody TS2/4 (shaded histogram) to αL in αL/β2 complex, or the nonbinding antibody X63 (open histogram). Numbers in the parentheses are clone numbers of the K562 stable transfectants.

FIG. 4 depicts the binding of LFA-1 transfectants to immobilized ICAM-1. Panel A, 293T transient transfectants, and Panels B and C, K562 stable transfectants. In Panels A and B, binding of the transfectants to immobilized ICAM-1 was determined in L 15 medium containing $Ca^{2+}$ and $Mg^{2+}$ in the presence or absence (control) of the activating antibody CBRLFA-1/2 at 10 .mu.g/ml. In Panel C, the binding assay was performed in TBS, pH7.5 supplemented with divalent cations or EDTA as indicated. Numbers in the parentheses are clone numbers of the K562 stable transfectants. Results are mean±SD of triplicate samples and representative of at least three experiments.

DETAILED DESCRIPTION OF THE INVENTION

Figure 1:
FIG. 1 is a stereodiagram of the high affinity model of the LFA-1 I domain, with mutations to introduce a disulfide bond. The model was prepare using segments of the putative high affinity Mac-1 I domain structures and a putative low affinity LFA-1 I domain structure as templates. The K287C and K294C mutations were included in the model. The sidechains and disulfide bond of C287 and C294 are shown. The $Mg^{2+}$ ion of the MIDAS is shown as a sphere. Sidechains of residues important in binding to ICAM-1 and ICAM-2 are shown with sidechains and sulfur, oxygen, and nitrogen atoms. These residues, defined as important in species-specific binding to ICAM-1 (Huang, C and Springer, T A (1995) *J Biol Chem* 270:19008-19016) or by at least a 2-fold effect on binding to ICAM-1 or ICAM-2 upon mutation to alanine (Edwards, C P et al. (1998) *J Biol Chem* 273:28937-28944), are M140, E146, T175, L205, E241, T243, S245, and K263. Note that these residues surround the $Mg^{2+}$ ion, and are distant from the disulfide. Prepared with RIBBONS (Carson, M (1997) Methods in Enzymology, R M Sweet and C W Carter eds., Academic Press pp. 493-505).

The present invention is based, at least in part, on a method for stabilizing a polypeptide in a desired conformation by introducing at least one disulfide bond into the polypeptide. In one embodiment, based on NMR or crystal structures of specific protein conformations, computational design is used to introduce a disulfide bond that locks the protein in a particular conformation. As used herein, a "conformation" or "conformer" refers to the three dimensional structure of a protein. A "desired" conformation includes a protein conformation that is conducive to a particular use of the polypeptide, e.g., a conformation that supports a particular biological function and/or activity, or a therapeutic effect. As used herein, the terms "polypeptide" and "protein" are used interchangeably throughout.

In one embodiment, a desired conformation is a protein conformation which promotes or activates a biological function and/or activity, e.g., an open or active conformation. In another embodiment, a desired conformation is a protein conformation which inhibits or suppresses a biological function and/or activity, e.g., a closed or inactive conformation.

In particular, the method of the invention includes modeling a protein, or a functional domain thereof, on a template of the desired three-dimensional structure of the protein and introducing cysteines which are able to form a disulfide bond only in the desired conformation of the protein, thus stabilizing the protein in that particular conformation. The protein can be any protein, or domain thereof, for which a three dimensional structure is known or can be generated, and is preferably a protein that exists in two different conformations. Computational algorithms for designing and/or modeling protein conformations are described, for example, in WO 98/47089. The SSBOND program (Hazes, B and Dijkstra, B W (1988) Protein Engineering 2:119-125) can be used to identify positions where disulfide bonds can be introduced in a protein structure by mutating appropriately positioned pairs of residues to cysteine.

Disulfide bond formation occurs between two cysteine residues that are appropriately positioned within the three-dimensional structure of a polypeptide. In one embodiment of the invention, a polypeptide is stabilized in a desired conformation by introducing at least one cysteine substitution into the amino acid sequence such that a disulfide bond is formed. The introduction of a single cysteine substitution is performed in circumstances in which an additional cysteine residue is present in the native amino acid sequence of the polypeptide at an appropriate position such that a disulfide bond is formed. In a preferred embodiment, two cysteine substitutions are introduced into the amino acid sequence of the polypeptide at positions that allow a disulfide bond to form, thereby stabilizing the polypeptide in a desired conformation. In another embodiment, the distance between the Cβ carbons of the residues that are substituted for cysteine is 3.00-8.09.ANG. In yet another embodiment, the distance between the Cβ carbons in the disulfide bond is in the range of 3.41-7.08.ANG.

In one embodiment of the invention, cysteine substitutions are introduced such that the formation of a disulfide bond is favored only in one protein conformation, such that the protein is stabilized in that particular conformation.

Preparation of a Modified Polypeptide of the Invention by Introducing Cysteine substitutions is preferably achieved by mutagenesis of DNA encoding the polypeptide of interest (e.g., an integrin polypeptide). For example, an isolated nucleic acid molecule encoding a modified integrin I-domain polypeptide can be created by introducing one or more nucleotide substitutions into the nucleotide sequence of an integrin gene such that one or more amino acid substitutions, e.g., cysteine substitutions, are introduced into the encoded protein. Mutations can be introduced into a nucleic acid sequence by standard techniques, such as site-directed mutagenesis and PCR-mediated mutagenesis.

Suitable proteins include, but are not limited to, industrially and therapeutically important proteins such as: 1) signaling molecules, such as small G proteins, trimeric G protein alpha subunits, tyrosine kinases, and G protein-coupled receptors; 2) enzymes under allosteric control, 3) zymogens that undergo conformational change after activation by proteolytic cleavage, such as the proteases (convertases and factors) of the complement and clotting cascades, and 4) proteolytically activated effector molecules such as complement components C3 and C4, and fibrinogen. In one embodiment, the method of the invention can be used to stabilize a protein in a biologically active conformation, e.g., a conformation that is enzymatically active or has ligand binding capacity and/or effector functions, e.g., an "open" conformation. In another embodiment, the method of the invention can be used to stabilize a protein in a biologically inactive conformation, e.g., a conformation that is enzymatically inactive or does not have ligand binding capacity and/or effector functions, e.g., a "closed" conformation.

Proteins that are stabilized in a particular conformation may find use in, for example, in proteomic screening technologies. In proteomic screens of tissues and disease states, antibodies, polypeptide, and/or small molecules that are specific for, e.g., an active protein conformer or an inactive protein conformer, can be used to assess the activity of different cellular signaling, metabolic, and adhesive pathways. Thus, associations can be made between specific diseases and the activation of specific biochemical and signaling pathways. Furthermore, the invention relates to the polypeptides, antibodies, and small molecules identified using the methods described herein and uses for same, e.g., to treat, for example, inflammatory disorders. Conformer-specific reagents can also be placed on chips and used to screen tissue extracts, or used to stain tissue sections. Furthermore, drugs or antibodies, e.g., anti-integrin antibodies which specifically recognize a modified integrin I-domain polypeptide, e.g., an anti-LFA-1 antibody which specifically recognizes a modified LFA-1 I-domain polypeptide, that are selective for a particular conformer, e.g., an open conformer or a closed conformer, may provide differential therapeutic effects. Therefore, selective screening assays using a protein stabilized in a particular conformer can be used to rationally obtain compounds with a desired activity.

Integrins

Integrins exist on cell surfaces in an inactive conformation that does not bind ligand. Upon cell activation, integrins change shape (conformation) and can bind ligand. Over 20 different integrin heterodimers (different α and β subunit combinations) exist that are expressed in a selective fashion on all cells in the body. After activation, integrins bind in a specific manner to protein ligands on the surface of other cells, in the extracellular matrix, or that are assembled in the clotting or complement cascades. Integrins on leukocytes are of central importance in leukocyte emigration and in inflammatory and immune responses. Ligands for the leukocyte integrin Mac-1 (.alpha.M.beta.2) include the inflammation-associated cell surface molecule ICAM-1, the complement component iC3b, and the clotting component fibrinogen. Ligands for the leukocyte integrin LFA-1 (.alpha.L.beta.2) include ICAM-1, ICAM-2, and ICAM-3. Antibodies to leukocyte integrins can block many types of inflammatory and auto-immune diseases, by, e.g., modulating, e.g., inhibiting, for example, cell to cell interactions or cell to extracellular matrix interactions. Integrins on platelets are important in clotting and in heart disease; approved drugs include the antibody abciximab (Reopro™) and the peptide-like antagonist eptifibatide (Integrilin™). Integrins on connective tissue cells, epithelium, and endothelium are important in disease states affecting these cells. They regulate cell growth, differentiation, wound healing, fibrosis, apoptosis, and angiogenesis. Integrins on cancerous cells regulate invasion and metastasis.

To antagonize integrins, drugs are needed that bind to the active, ligand-binding conformation. Most antibodies bind to both the active and inactive conformations, since only a small portion of the surface of the integrin molecule changes shape. It is desirable that antibodies bind only to the active integrin conformation, e.g., the "open" conformation, because binding to the inactive conformation can lead to side reactions, generation of anti-idiotypic antibodies, and result in clearance of the antibody and, thus, requires much higher doses to be administered.

The methods described herein have been successfully used to introduce disulfide bonds into the I domains of the integrins, e.g., LFA-1 and Mac-1. Accordingly, in another aspect, the invention provides a modified integrin I-domain polypeptide containing at least one disulfide bond, such that said modified I-domain polypeptide is stabilized in a desired conformation. A modified integrin I-domain polypeptide of the invention may be derived from an I-domain of an integrin α subunit including α1, α2, α 10, α11, αD, αE, αL (CD11a), αM (CD11b) and αX (CD11c).

As used herein, a "modified integrin I-domain polypeptide" or "modified integrin polypeptide" includes an integrin I-domain polypeptide that has been altered with respect to the wild-type sequence or the native state such that at least one disulfide bond has been introduced into the polypeptide thereby stabilizing the I-domain in a desired conformation.

The terms "derived from" or "derivative", as used interchangeably herein, are intended to mean that a sequence is identical to or modified from another sequence, e.g., a naturally occurring sequence. Derivatives within the scope of the invention include polynucleotide and polypeptide derivatives. Polypeptide or protein derivatives include polypeptide or protein sequences that differ from the sequences described or known in amino acid sequence, or in ways that do not involve sequence, or both, and still preserve the activity of the polypeptide or protein. Derivatives in amino acid sequence are produced when one or more amino acid is substituted with a different natural amino acid, an amino acid derivative or non-native amino acid. In certain embodiments protein derivatives include naturally occurring polypeptides or proteins, or biologically active fragments thereof, whose sequences differ from the wild-type sequence by one or more conservative amino acid substitutions, which typically have minimal influence on the secondary structure and hydrophobic nature of the protein or peptide. Derivatives may also have sequences which differ by one or more non-conservative amino acid substitutions, deletions or insertions which do not abolish the biological activity of the polypeptide or protein.

Conservative substitutions (substituents) typically include the substitution of one amino acid for another with similar characteristics (e.g., charge, size, shape, and other biological properties) such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

In other embodiments, derivatives with amino acid substitutions which are less conservative may also result in desired derivatives, e.g., by causing changes in charge, conformation and other biological properties. Such substitutions would include, for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics. The polypeptides and proteins of this invention may also be modified by various changes such as insertions, deletions and substitutions, either conservative or nonconservative where such changes might provide for certain advantages in their use.

In a preferred embodiment, a modified integrin I-domain polypeptide is stabilized in the open conformation, and binds ligand with high affinity.

In one embodiment, a modified integrin I-domain polypeptide of the invention is encoded by an amino acid sequence containing at least one cysteine substitution, and preferably two cysteine substitutions, as compared to the wild-type sequence. In another embodiment, the distance between the Cβ carbons of the residues that are substituted for cysteines is in the range of 3.00-8.09.ANG., e.g., as predicted by protein modeling. In a further embodiment, the distance between the Cβ carbons in the disulfide bond is in the range of 3.41-7.08.ANG.

The introduction of cysteine residues at appropriate positions within the amino acid sequence of the I-domain polypeptide allows for the formation of a disulfide bond that stabilizes the domain in a particular conformation, e.g., an active "open" conformation, or an inactive "closed" conformation. For example, the αL K287C/K294C, E284C/E301C, L161C/F299C, K160C/F299C, L161C/T300C, and L289C/K294C mutants, and the αM Q163C/Q309C and D294C/Q31 IC mutants are stabilized in the "open" conformation that bind ligand with high or intermediate affinity, whereas the αL L289C/K294C mutant and the αM Q163C/R313C mutants are stabilized in an inactive or "closed" conformation that does not bind ligand. The affinity of E284C/E301C is nearly comparable to that of K287C/K294C, e.g., high-affinity. The affinity of L161C/F299C, K160C/F299C, and L161C/T300C are significantly higher than wild-type, but 20-30 times lower than high-affinity αL I-domain, K287C/K294C. L161C/F299C, K160C/F299C, and L161C/T300C are referred to herein as intermediate affinity αL I-domains.

In one embodiment, the invention provides a modified integrin I-domain which is comprised within an integrin α subunit, and which may be further associated with an integrin β subunit. In another embodiment, a modified integrin I-domain polypeptide of the invention is a soluble polypeptide. Furthermore, the invention provides a modified integrin I-domain polypeptide which is operatively linked to a heterologous polypeptide.

A model of the I-like domain of the integrin β-subunit that is supported by experimental data (Huang, C et al. (2000) J Biol Chem 275:21514-24) has also been made. The data confirm the location of the key C-terminal α-helix that undergoes the dramatic 10 .ANG. conformational movement in I domains. The I and I-like domains align well in this region. Accordingly, in another aspect, the invention provides a modified integrin I-like domain polypeptide containing at least one disulfide bond, such that said modified I-like domain polypeptide is stabilized in a desired conformation.

In a preferred embodiment, a modified integrin I-like domain polypeptide is stabilized in the open conformation, and binds ligand with high affinity. In one embodiment, a modified integrin I-like domain polypeptide of the invention is encoded by an amino acid sequence containing at least one cysteine substitution, and preferably two cysteine substitutions, as compared to the wild-type sequence.

In one embodiment, the invention provides a modified integrin I-like domain which is comprised within an integrin β subunit, and which may be further associated with an integrin α subunit. In another embodiment, a modified integrin I-like domain polypeptide of the invention is a soluble polypeptide. Furthermore, the invention provides a modified integrin I-like domain polypeptide which is operatively linked to a heterologous polypeptide.

Integrins are key targets in many diseases. Accordingly, isolated high affinity I-domains of the invention, as well as antibodies, or small molecule antagonists selective for activated leukocyte integrins can be used to modulate, e.g., inhibit or prevent, autoimmune and inflammatory disease, transplant rejection, and ischemia/reperfusion injury as in hypovolemic shock, myocardial infarct, and cerebral shock. Furthermore, co-crystals of high affinity I domains bound to natural ligands and/or small molecule antagonists can readily be made, which will enable computational drug design, and advance modification and improvement of drug development candidates.

Accordingly, the invention provides a method for identifying a modulator of integrin activity comprising assaying the ability of a test compound to bind to a modified integrin I-domain polypeptide which is stabilized in the open conformation. In another embodiment, the invention provides a method for identifying a compound capable of modulating the interaction of an integrin and a cognate ligand wherein binding of a ligand to a modified integrin I-domain polypeptide which is stabilized in the open conformation is assayed in the presence and absence of a test compound.

The invention also provides a composition comprising a modified integrin I-domain polypeptide or an anti-integrin antibody, e.g., an anti-LFA-1 antibody (or an antigen binding fragment thereof) which selectively binds to a modified integrin I-domain, e.g., an I-domain in the open conformation, and a pharmaceutically acceptable carrier. The compositions of the invention are used in therapeutic methods of the invention. For example, the invention provides methods for treating or preventing an integrin-mediated disorder (e.g., an inflammatory or autoimmune disorder) in a subject, or for inhibiting the binding of an integrin to a cognate ligand in a subject comprising administering to a therapeutically effective amount of a modified integrin I-domain polypeptide stabilized in the open conformation or anti-integrin antibody (or an antigen binding fragment thereof) which selectively binds to an integrin I-domain in the open conformation. In a preferred embodiment, the modified integrin I-domain polypeptide binds ligand with high affinity. In another preferred embodiment, the modified integrin I-domain polypeptide for therapeutic use is a soluble polypeptide, e.g., a fusion protein.

As used herein, an integrin mediated disorder includes, for example, an inflammatory or immune system disorder, and/or a cellular proliferative disorder. Examples of integrin-mediated disorders include myocardial infarction, stroke, restenosis, transplant rejection, graft versus host disease or host versus graft disease, and reperfusion injury. An inflammatory or immune system disorder includes, but is not limited to adult respiratory distress syndrome (ARDS), multiple organ injury syndromes secondary to septicemia or trauma, viral infection, inflammatory bowel disease, ulcerative colitis, Crohn' disease, leukocyte adhesion deficiency II syndrome, thermal injury, hemodialysis, leukapheresis, peritonitis, chronic obstructive pulmonary disease, lung inflammation, asthma, acute appendicitis, dermatoses with acute inflammatory components, wound healing, septic shock, acute glomerulonephritis, nephritis, amyloidosis, reactive arthritis, rheumatoid arthritis, chronic bronchitis, Sjorgen's syndrome, sarcoidosis, sclerodenna, lupus, polymyositis, Reiter' syndrome, psoriasis, dermatitis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, necrotizing enterocolitis, granulocyte transfusion associated syndromes, cytokine-induced toxicity, chronic mucocutaneous candidiasis, severe combined immunodeficiency), autoimmune disorders, and acute purulent meningitis or other central nervous system inflammatory disorders.

A "cellular proliferative disorder" includes those disorders that affect cell proliferation, activation, adhesion, growth, differentiation, or migration processes. As used herein, a "cellular proliferation, activation, adhesion, growth, differentiation, or migration process" is a process by which a cell increases in number, size, activation state, or content, by which a cell develops a specialized set of characteristics which differ from that of other cells, or by which a cell moves closer to or further from a particular location or stimulus. Disorders characterized by aberrantly regulated growth, activation, adhesion, differentiation, or migration. Such disorders include cancer, e.g., carcinoma, sarcoma, lymphoma or leukemia, examples of which include, but are not limited to, breast, endometrial, ovarian, uterine, hepatic, gastrointestinal, prostate, colorectal, and lung cancer, melanoma, neurofibromatosis, adenomatous polyposis of the colon, Wilms' tumor, nephroblastoma, teratoma, rhabdomyosarcoma; tumor invasion, angiogenesis and metastasis; skeletal dysplasia; hematopoietic and/or myeloproliferative disorders.

Various aspects of the invention are described in further detail in the following subsections.

Modified Integrin I-domain Polypeptides and Anti-Integrin I-Domain Antibodies

The methods of the invention include the use of isolated, modified integrin polypeptides, and biologically active portions thereof. As used herein, a modified integrin polypeptide includes a modified I-domain polypeptide and a modified I-like domain polypeptide. Modified integrin polypeptides of the invention include modified integrin I-domain and I-like domain polypeptides that are comprised within an integrin α or β subunit polypeptide, respectively; soluble modified integrin I-domain and I-like domain polypeptides; and modified integrin I-domain and I-like domain polypeptides that are operatively linked to a heterologous polypeptide, e.g., fusion proteins.

The cDNAs for multiple human integrin α and β subunit polypeptides have been cloned and sequenced, and the polypeptide sequences have been determined (see, for example, GenBank Accession Numbers: NM.sub.-002203 (α2), AF112345 (α10), NM_012211 (α11), NM-005353 (αD), NM-002208 (.αE), NM-000887 (αX), NM-000632 (αM), NM-002209 (αL), X68742 and P56199 (α1), NM-000211 (02), NM-000212 (β3), NM-002214 (β8)). In particular, the polypeptide sequences encoding human αL and βM are set forth as SEQ ID NO:2 (GenBank Accession No. P20701) and SEQ ID NO:4 (GenBank Accession No. P11215), respectively. In addition, the sequences encoding integrin α and β subunit polypeptides from other species are available in the art. Furthermore, as described previously, three dimensional structure of the αM, αL, α1 and α2 I-domains has been solved (Lee, J-O, et al. (1995) Structure 3:1333-1340; Lee, J-O, et al. (199S) Cell 80:631-638; Qu, A and Leahy, D J (1995) Proc Natl Acad USA 92:10277-10281; Qu, A and Leahy, D J (1996) Structure 4:931-942; Emsley, J et al. (1997) J Biol Chem 272:28512-28517; Baldwin, E T et al. (1998) Structure 6:923-935; Kallen, J et al. (1999) J Mol Biol 292:1-9).

Isolated modified integrin polypeptides of the present invention preferably have an amino acid sequence that is sufficiently identical to the amino acid sequence of a native integrin polypeptide, yet which comprise at least one, and preferably two cysteine substitutions, such that a disulfide bond is formed that stabilizes the polypeptide in a desired conformation. As used herein, the term "sufficiently identical" refers to an amino acid (or nucleotide) sequence which contains a sufficient or minimum number of identical or equivalent (e.g., an amino acid residue that has a similar side chain) amino acid residues (or nucleotides) to a integrin amino acid (or nucleotide) sequence such that the polypeptide shares common structural domains or motifs, and/or a common functional activity with a native integrin polypeptide. For example, amino acid or nucleotide sequences which share at least 30%, 40%, or 50%, preferably 60%, more preferably 70%, 75%, 80%, 85% or 90%, 91%, 92%, 93%, 94%, 95% or greater identity and share a common functional activity (e.g., an activity of a modified integrin I-domain or I-like domain as described herein) are defined herein as sufficiently identical. An integrin I-domain polypeptide may differ in amino acid sequence from the integrin polypeptides disclosed herein due to natural allelic variation or mutagenesis.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4.

As used herein, a "biologically active portion" of a modified integrin polypeptide (e.g., a modified integrin I-domain polypeptide) includes a fragment of a modified integrin polypeptide which retains a modified integrin polypeptide activity. Typically, a biologically active portion of a modified integrin polypeptide comprises at least one domain or motif with at least one activity of the modified integrin polypeptide, e.g., ligand binding. In a preferred embodiment, biologically active portions of a modified integrin polypeptide include modified integrin I-domain polypeptides. Biologically active portions of a modified integrin polypeptide may comprise amino acid sequences sufficiently identical to or derived from the amino acid sequence of a modified integrin polypeptide, which include less amino acids than the full length modified integrin polypeptide, and exhibit at least one activity of a modified integrin polypeptide. Biologically active portions of a modified integrin polypeptide, e.g., a modified I-domain or I-like domain, can be used as targets for developing agents which modulate a integrin polypeptide activity, e.g., ligand binding, adhesion, e.g., cell to cell adhesion or cell to extracellular matrix adhesion, and/or signaling activity. A biologically active portion of a modified integrin polypeptide comprises a polypeptide which can be prepared by recombinant techniques and evaluated for one or more of the functional activities of a modified integrin polypeptide.

In a preferred embodiment, modified integrin polypeptides are produced by recombinant DNA techniques. For example, a modified integrin polypeptide can be isolated from a host cell transfected with a polynucleotide sequence encoding a modified integrin polypeptide (e.g., a I-domain polypeptide or a soluble I-domain fusion protein) using an appropriate purification scheme using standard protein purification techniques. Alternative to recombinant expression, a modified integrin polypeptide can be synthesized chemically using standard peptide synthesis techniques.

An "isolated" or "purified" polypeptide or protein, or biologically active portion thereof is substantially free of cellular material or other contaminating proteins from the source, e.g., the cellular source, from which the modified integrin I-domain polypeptide is derived, or substantially free from chemical precursors or other chemicals when chemically synthesized. The language "substantially free of cellular material" includes preparations of modified integrin polypeptide in which the protein is separated from cellular components of the cells from which it is isolated or recombinantly produced. In one embodiment, the language "substantially free of cellular material" includes preparations of modified integrin polypeptide having less than about 30% (by dry weight) of non-modified integrin polypeptide (also referred to herein as a "contaminating protein"), more preferably less than about 20% of non-modified integrin polypeptide, still more preferably less than about 10% of non-modified integrin polypeptide, and most preferably less than about 5% non-modified integrin polypeptide. When the modified integrin polypeptide or biologically active portion thereof is recombinantly produced, it is also preferably substantially free of culture medium, i.e., culture medium.represents less than about 20%, more preferably less than about 10%, and most preferably less than about 5% of the volume of the protein preparation.

The language "substantially free of chemical precursors or other chemicals" includes preparations of modified integrin polypeptide in which the protein is separated from chemical precursors or other chemicals which are involved in the synthesis of the protein. In one embodiment, the language "substantially free of chemical precursors or other chemicals" includes preparations of modified integrin polypeptide having less than about 30% (by dry weight) of chemical precursors or non-modified integrin polypeptide chemicals, more preferably less than about 20% chemical precursors or non-modified integrin polypeptide chemicals, still more preferably less than about 10% chemical precursors or non-modified integrin polypeptide chemicals, and most preferably less than about 5% chemical precursors or non-modified integrin polypeptide chemicals.

The methods of the invention may also use modified integrin polypeptides that are chimeric or fusion proteins. As used herein, a modified integrin "chimeric protein" or "fusion protein" comprises a modified integrin polypeptide operatively linked to a non-modified integrin polypeptide, e.g., a heterologous polypeptide. In a preferred embodiment, a modified integrin fusion protein comprises at least an I-domain or an I-like domain. Within the fusion protein, the term "operatively linked" is intended to indicate that the modified integrin polypeptide and the heterologous polypeptide sequences are fused in-frame to each other. The heterologous polypeptide can be fused to the N-terminus or C-terminus of the modified integrin polypeptide.

For example, in a preferred embodiment, the fusion protein is a modified integrin-I-domain fusion protein in which the Fc region, e.g., the hinge, C1 and C2 sequences, of an immunoglobulin, (e.g., human IgG1) is fused to the C-terminus of the modified integrin sequences. Integrin immunoglobulin chimeras can be constructed essentially as described in WO 91/08298. Such fusion proteins can facilitate the purification of recombinant modified integrin polypeptides. In another embodiment, the fusion protein is a modified integrin I-domain polypeptide fused to a heterologous transmembrane domain, such that the fusion protein is expressed on the cell surface.

The modified integrin polypeptides and fusion proteins of the invention can be incorporated into pharmaceutical compositions and administered to a subject in vivo. In an exemplary embodiment, a soluble modified integrin I-domain polypeptide stabilized in an open, ligand binding conformation, or fusion protein thereof may be used to modulate integrin activity (e.g., integrin binding to a cognate ligand) in a subject. In another embodiment, a soluble modified integrin I-domain polypeptide or fusion protein may be used to treat an inflammatory or immune system disorder, e.g., an autoimmune disorder. In another embodiment, a soluble modified integrin polypeptide or fusion protein may be used to treat a cellular proliferative disease. Use of soluble modified integrin polypeptides and fusion proteins can also be used to affect the bioavailability of a integrin ligand, e.g., ICAM.

Moreover, the modified integrin polypeptides and fusion proteins of the invention can be used as immunogens to produce anti-integrin antibodies in a subject, e.g., anti-LFA-1 antibodies, and in screening assays to identify molecules which modulate integrin activity, and/or modulate the interaction of a integrin polypeptide with a integrin ligand or receptor.

Preferably, a modified integrin fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A modified integrin polypeptide-encoding nucleic acid can be cloned into such an expression vector such that the fusion moiety is linked in-frame to the modified integrin polypeptide.

The methods of the present invention may also include the use of modified integrin polypeptides which function as either integrin agonists (mimetics) or as integrin antagonists. An agonist of an integrin polypeptide can retain substantially the same, or a subset, of the biological activities of the naturally occurring form of a integrin polypeptide. An antagonist of an integrin polypeptide can inhibit one or more of the activities of a native form of the integrin polypeptide by, for example, competitively modulating an integrin activity. Thus, specific biological effects can be elicited by treatment with a modified integrin polypeptide stabilized in a desired conformation.

An isolated, modified integrin polypeptide, e.g., a modified LFA-1 polypeptide, or a portion or fragment thereof, can be used as an immunogen to generate antibodies that bind to a specific conformation of an integrin, e.g., an integrin I-domain, using standard techniques for polyclonal and monoclonal antibody preparation (see, generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet. 3:231-36). Moreover, the ordinarily skilled artisan will appreciate that there are many variations of such methods which also would be useful. Preparation of anti-LFA-1 antibodies is described in, for example, U.S. Pat. No. 5,622,700, the entire content of which is incorporated herein by this reference.

The term "antibody" as used herein refers to immunoglobulin molecules and immunologically active portions of immunoglobulin molecules, i.e., molecules that contain an antigen binding site which specifically binds (immunoreacts with) an antigen, e.g., an integrin I-domain in an open or closed conformation, or a modified integrin I-domain, such as an LFA-1 I-domain, e.g., an open or closed LFA-1 I-domain or a modified integrin I-domain of LFA-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind a modified integrin polypeptide e.g., a modified LFA-1 polypeptide, or a portion or fragment thereof. The term "monoclonal antibody" or "monoclonal antibody composition", as used herein, refers to a population of antibody molecules that contain only one species of an antigen binding site capable of immunoreacting with a particular epitope of a modified integrin polypeptide, e.g., a modified LFA-1 polypeptide, or a portion or fragment thereof. A monoclonal antibody composition thus typically displays a single binding affinity for a particular modified integrin polypeptide, or a portion or fragment thereof with which it immunoreacts.

Alternative to preparing monoclonal antibody-secreting hybridomas, a monoclonal anti-integrin antibody can be identified and isolated by screening a recombinant combinatorial immunoglobulin library (e.g., an antibody phage display library) with a modified integrin polypeptide, e.g., a modified integrin I-domain stabilized in the open conformation, to thereby isolate immunoglobulin library members that bind to an conformation specific epitope on an integrin polypeptide, e.g., an open conformation. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). With regard to screening for phage libraries with integrin I-domains locked in the high affinity conformation with a disulfide bond, note that it should be possible to elute specific phage by adding a reducing agent that breaks the disulfide and abolishes the high affinity conformation of the I-domain.

Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc. Acid Res. 19:4133-4137; Barbas et al. (1991) Proc. Natl. Acad. Sci. USA 88:7978-7982; and McCafferty et al. Nature (1990) 348:552-554.

Additionally, recombinant anti-integrin antibodies, such as chimeric and humanized monoclonal antibodies, comprising both human and non-human portions, which can be made using standard recombinant DNA techniques, can also be used in the methods of the present invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

In a preferred embodiment, an anti-integrin antibody of the invention binds selectively to an integrin I-domain in the open, high-affinity conformation, e.g., at an epitope that is unique to an activated integrin (also referred to herein as an activation specific epitope). In a preferred embodiment, an anti-integrin antibody of the invention modulates (e.g., inhibits) the binding interaction between an activated integrin and its cognate ligand. In another embodiment, an anti-integrin antibody inhibits leukocyte adhesion and/or aggregation. In another embodiment, an anti-integrin antibody of the invention binds selectively to an integrin I-domain in an open conformation, e.g., an LFA-1 I1-domain in an open conformation, or a modified integrin I-domain, e.g., a modified I-domain of an LFA-1 molecule.

An anti-integrin antibody (e.g., a monoclonal antibody) can be used in the methods of the invention to modulate the expression and/or activity of an integrin or an integrin I-domain polypeptide. An anti-integrin antibody can also be used to isolate modified integrin or integrin I-domain polypeptides, e.g., a modified LFA-1 polypeptide, or fusion proteins by standard techniques, such as affinity chromatography or immunoprecipitation. In another embodiment, an anti-integrin antibody can be used to remove and/or kill cells expressing activated integrin. Moreover, an anti-integrin antibody can be used to detect integrin polypeptides in a particular conformation (e.g., an activated integrin), for example, for the localization of stimulated and/or activated leukocytes. Furthermore, an anti-integrin antibody, e.g., an antibody which reacts with or binds an integrin I-domain in an open conformation or a modified integrin I-domain, can be used therapeutically as described herein. Accordingly anti-integrin antibodies can be used diagnostically to monitor protein levels in blood as part of a clinical testing procedure, e.g., to, for example, detect inflammation. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Isolated Nucleic Acid Molecules

The invention includes the use of isolated nucleic acid molecules that encode integrin polypeptides (e.g., a modified integrin I-domain polypeptide, e.g., a modified integrin I-domain or I-like domain polypeptide) or biologically active portions thereof.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleotide sequences encoding the wild-type human αL and αM polypeptides are set forth as SEQ ID NO:1 (GenBank Accession No. NM_002209) and SEQ ID NO:3 (Genbank Accession No. J03925), respectively. The isolated nucleic acid molecules of the present invention include the nucleotide sequences of SEQ ID NO:1 and SEQ ID NO:3, which encode the modified amino acid sequences of the αL and αM mutants described herein, e.g. identified below in Table 9. Table 9 illustrates the specific nucleotide residues which are altered to result in the modified αL and αM mutants as described herein. For example, the αL K287C/K294C mutant is a modified αL polypeptide, wherein there is a change in the amino acid sequence of αL (SEQ ID NO:2) such that amino acid residues 187 and 194 are substituted with cysteine residues. The corresponding wild-type nucleotide sequence, SEQ ID NO:1, is modified at nucleotide residues 1022-1024 and 1043-1045, respectively. Therefore, as shown in Table 9, for the αL K287C/K294C mutant at amino acid K287, the corresponding nucleotide residues in the wild-type αL nucleic acid sequence (SEQ ID NO:1), nucleotide residues 1022-1024, are modified from "aaa" to "tgt."

TABLE 9

| Mutants | | | | Nucleotide sequence | |
|---|---|---|---|---|---|
| αM or αL | Mutations | # Amino Acid | # Nucleotode | WT | mutant |
| αL | K287C/K294C | K287 | 1022-1024 | aaa | tgt |
| | | K294 | 1043-1045 | aag | tgt |
| | E284C/E301C | E284 | 1013-1015 | gag | tgt |
| | | E301 | 1064-1066 | gag | tgt |
| | L161C/F299C | L161 | 644-646 | ctc | tgt |
| | | F299 | 1058-1060 | ttc | tgt |
| | K160C/F299C | K160 | 641-643 | aaa | tgt |
| | | F299 | 1058-1060 | ctc | tgt |
| | L161C/T300C | L161 | 644-646 | ctc | tgt |
| | | T300 | 1061-1063 | act | tgt |
| | L289C/K294C | L289 | 1028-1030 | ctg | tgt |
| | | K294 | 1043-1045 | aag | tgt |
| αM | Q163C/Q309C | Q163 | 607-609 | caa | tgt |
| | | Q309 | 1045-1047 | cag | tgt |
| | D294C/Q311C | D294 | 1000-1002 | gat | tgt |
| | | Q311 | 1051-1053 | cag | tgt |
| | Q163C/R313C | Q163 | 607-609 | caa | tgt |
| | | R313 | 1057-1059 | cgg | tgt |

αL; GenBank NM_002209
αM; GeneBank J03925

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, an isolated nucleic acid molecule encoding a modified integrin I-domain polypeptide can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The skilled artisan will further appreciate that further changes can be introduced by mutation into the nucleotide sequence encoding a modified integrin polypeptide, thereby leading to changes in the amino acid sequence of the encoded modified integrin polypeptide, without further altering the structural characteristics or functional ability of the modified integrin polypeptide. For example, nucleotide substitutions leading to amino acid substitutions at "non-essential" amino acid residues can be made in the sequence encoding a modified integrin polypeptide. A "non-essential" amino acid residue is a residue that can be altered from the sequence of a modified integrin polypeptide without further altering the structure and/or biological activity. In accordance with the methods of the invention, computational design and modeling are used to determine which amino acid residues are amenable to alteration in order to achieve the desired protein conformation.

Accordingly, the methods of the invention may include the use of nucleic acid molecules encoding modified integrin polypeptides that contain changes in amino acid residues that are not essential for activity.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a modified integrin polypeptide is preferably replaced with another amino acid residue from the same side chain family.

Recombinant Expression Vectors and Host Cells

Another aspect of the invention pertains to vectors, for example, recombinant expression vectors, containing a nucleic acid encoding a modified integrin polypeptide (or a portion thereof), e.g., an integrin I-domain or I-like domain polypeptide or fusion protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the methods of the invention may include other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., modified integrin I-domain polypeptides, fusion proteins, and the like).

Accordingly, the invention provides a method for producing a modified integrin polypeptide, e.g., a modified integrin I-domain polypeptide, by culturing in a suitable medium, a host cell of the invention (e.g., a prokaryotic or eukaryotic host cell) containing a recombinant expression vector such that the protein is produced.

The recombinant expression vectors of the invention can be designed for expression of modified integrin polypeptides or fusion proteins in prokaryotic or eukaryotic cells, e.g., for use in the methods of the invention. For example, modified integrin I-domain polypeptides or fusion proteins can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility and/or stability of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Purified modified integrin I-domain fusion proteins (e.g., soluble 1-domain-Ig) can be utilized to modulate integrin activity, as described herein.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec 1 (Baldari, et al., (1987) EMBO J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picz (InVitrogen Corp, San Diego, Calif.).

Alternatively, modified integrin polypeptides can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J 6:187-195). When used in mammalian cells, the expression vector'control functions are often provided by viral regulatory elements.

For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:23 5-275), in particular promoters of T cell receptors (Winoto and Baltimore (1989) EMBO J 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), endothelial cell-specific promoters (e.g., KDR/flk promoter; U.S. Pat. No. 5,888,765), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Another aspect of the invention pertains to host cells into which a nucleic acid molecule encoding a modified integrin polypeptide of the invention is introduced, e.g., a modified integrin I-domain nucleic acid molecule within a recombinant expression vector or a modified integrin I-domain nucleic acid molecule containing sequences which allow it to homologously recombine into a specific site of the host cell'genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a modified integrin polypeptide or fusion protein can be expressed in bacterial cells such as *E. coli*, insect cells, yeast or mammalian cells (such as hematopoietic cells, leukocytes, K562 cells, 293T cells, human umbilical vein endothelial cells (HUVEC), human microvascular endothelial cells (HMVEC), Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acids encoding a selectable marker can be introduced into a host cell on the same vector as that encoding a modified integrin polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a modified integrin polypeptide, e.g., a modified integrin I-domain polypeptide or fusion protein, for use in the methods of the invention. In one embodiment, a host cell (into which a recombinant expression vector encoding a modified integrin I-domain polypeptide or fusion protein has been introduced) is cultured in a suitable medium such that a modified integrin I-domain polypeptide or fusion protein is produced. In another embodiment, a modified integrin I-domain polypeptide or fusion protein is isolated from the medium or the host cell. A recombinant cell expressing a modified integrin polypeptide or fusion protein can also be administered to a subject to modulate integrin activity.

The host cells of the invention can also be used to produce non-human transgenic animals. For example, in one embodiment, a host cell of the invention is a fertilized oocyte or an embryonic stem cell into which a modified integrin I-domain polypeptide-coding sequences have been introduced. Such host cells can then be used to create non-human transgenic animals in which exogenous modified integrin I-domain sequences have been introduced into their genome or homologous recombinant animals in which endogenous integrin I-domain sequences have been altered. Such animals are useful for studying the function and/or activity of a modified integrin I-domain molecule and for identifying and/or evaluating modulators of modified integrin I-domain polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous integrin I-domain gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a modified integrin I-domain-encoding nucleic acid into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a modified integrin I-domain transgene to direct expression of a modified integrin I-domain protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986).

To create a homologous recombinant animal, a vector is prepared which contains at least a portion of a modified integrin I-domain gene into which a deletion, addition or substitution has been introduced to thereby alter, e.g., functionally disrupt, the modified integrin I-domain gene. The modified integrin I-domain gene can be a human gene, but more preferably, is a non-human homologue of a human modified integrin I-domain gene. For example, a mouse modified integrin I-domain gene can be used to construct a homologous recombination nucleic acid molecule, e.g., a vector, suitable for altering an endogenous modified integrin I-domain gene in the mouse genome. In a preferred embodiment, the homologous recombination nucleic acid molecule is designed such that, upon homologous recombination, the endogenous modified integrin I-domain gene is functionally disrupted (i.e., no longer encodes a functional protein; also referred to as a "knock out" vector). Alternatively, the homologous recombination nucleic acid molecule can be designed such that, upon homologous recombination, the endogenous modified integrin I-domain gene is mutated or otherwise altered but still encodes functional protein (e.g., the upstream regulatory region can be altered to thereby alter the expression of the endogenous modified integrin I-domain protein). In the homologous recombination nucleic acid molecule, the altered portion of the modified integrin I-domain gene is flanked at its 5' and 3' ends by additional nucleic acid sequence of the modified integrin I-domain gene to allow for homologous recombination to occur between the exogenous modified integrin I-domain gene carried by the homologous recombination nucleic acid molecule and an endogenous modified integrin I-domain gene in a cell, e.g., an embryonic stem cell. The additional flanking modified integrin I-domain nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced modified integrin I-domain gene has homologously recombined with the endogenous modified integrin I-domain gene are selected (see e.g., Li, E. et al. (1992) Cell 69:915). The selected cells can then injected into a blastocyst of an animal (e.g., a mouse) to form aggregation chimeras (see e.g., Bradley, A. in Teratocarcinomas and Embryonic Stem Cells:A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) Current Opinion in Biotechnology 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Screening Assays

The invention provides a method (also referred to herein as a "screening assay") for identifying modulators, i.e., candidate or test compounds or agents (e.g., peptides, antibodies, peptidomimetics, small molecules (organic or inorganic) or other drugs) which modulate integrin activity. These assays are designed to identify compounds, for example, that bind to an integrin I-domain polypeptide, e.g., an integrin I-domain polypeptide in an active conformation, bind to other proteins that interact with an integrin I-domain polypeptide, induce binding, and modulate the interaction of an integrin I-domain polypeptide with other proteins, e.g., an integrin ligand, e.g., ICAM, and thus modulate integrin activity.

As used herein, the term "modulator of integrin activity" includes a compound or agent that is capable of modulating or regulating at least one integrin activity, as described herein. Modulators of integrin activity may include, but are not limited to, small organic or inorganic molecules, nucleic acid molecules, peptides, antibodies, and the like. A modulator of integrin activity can be an inducer or inhibitor of integrin activity, e.g., cell adhesion or ligand binding. As used herein, an "inducer of integrin activity" stimulates, enhances, and/or mimics an integrin activity. As used herein, an "inhibitor of integrin activity" reduces, blocks or antagonizes an integrin activity.

As used interchangeably herein, an "integrin activity", or an "integrin-mediated activity" refers to an activity exerted by an integrin polypeptide or nucleic acid molecule on an integrin responsive cell, or on integrin ligand or receptor, as determined in vitro and in vivo, according to standard techniques. In one embodiment, an integrin activity is the ability to mediate cell adhesion events, e.g., cell to cell or cell to extracellular matrix adhesion. In another embodiment, an integrin activity is the ability to transduce cellular signaling events. In yet another embodiment, an integrin activity is the ability to bind a ligand, e.g., ICAM.

In a preferred embodiment, a soluble, recombinant high affinity integrin I-domain can be used to screen for small molecule antagonists that interfere with integrin ligand binding. Furthermore, antagonists, e.g., antibodies, with direct/competitive and indirect/noncompetitive modes of inhibition can be discriminated, based on comparison with effects on wild-type integrin I-domains which show minimal ligand binding activity. For example, an indirect inhibitor should inhibit ligand binding by an activated, wild-type integrin I-domain, but not by a disulfide-locked high affinity I-domain.

In another embodiment, an assay is a cell-based assay comprising contacting a cell expressing a modified integrin polypeptide on the cell surface with a test compound and determining the ability of the test compound to modulate (e.g., induce or inhibit) an integrin activity. For example, a cell expressing a modified integrin I-domain polypeptide stabilized in an open conformation on the cell surface is contacted with a test compound, and the ability of the test compound to modulate adhesion to an integrin ligand is determined, as described and exemplified herein.

In yet another embodiment, the ability of a test compound to modulate integrin ligand binding can also be determined, for example, by coupling a modified integrin I-domain polypeptide that is stabilized in an open conformation with a detectable label such that the binding of the modified integrin polypeptide can be determined by detecting the amount of labeled integrin I-domain binding to an immobilized integrin ligand.

Animal-based model systems, such as an animal model of inflammation, may be used, for example, as part of screening strategies designed to identify compounds which are modulators of integrin activity. Thus, the animal-based models may be used to identify drugs, pharmaceuticals, therapies and interventions which may be effective in modulating inflammation and treating integrin-mediated disorders. For example, animal models may be exposed to a compound, suspected of exhibiting an ability to modulate integrin activity, and the response of the animals to the exposure may be monitored by assessing inflammatory activity before and after treatment. Transgenic animals, e.g., transgenic mice, which express modified integrin I-domain polypeptides as described herein can also be used to identify drugs, pharmaceuticals, therapies and interventions which may be effective in modulating inflammation and treating integrin-mediated disorders In another aspect, the invention pertains to a combination of two or more of the assays described herein. For example, a modulator of integrin activity can be identified using a cell-based assay, and the ability of the agent to modulate integrin activity can be confirmed in vivo, e.g., in an animal such as an animal model for inflammation.

Moreover, screening assays can be used to identify inducers of integrin activity, for example, that mimic the activity of a integrin polypeptide, e.g., the binding of an integrin to a ligand or receptor, or the activity of an integrin towards an integrin responsive cell. Such compounds may include, but are not limited to, peptides, antibodies, or small organic or inorganic compounds. In one embodiment, an anti-integrin antibody, e.g., an anti-LFA-1 antibody of the invention which selectively binds to an open, activated conformer can be used to assess the ability of a test compound to activate integrin.

The test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

This invention further pertains to novel agents identified by the above-described screening assays. With regard to intervention, any treatments which modulate integrin activity and/or inflammatory activity should be considered as candidates for human therapeutic intervention.

Pharmaceutical Compositions

The nucleic acid molecules encoding modified integrin polypeptides, modified integrin polypeptides (e.g., modified I-domain polypeptides and fusion proteins), and active fragments thereof, anti-integrin I-domain antibodies, and integrin modulators (also referred to herein as "active compounds") DNA vaccines, or DNA vectors of the invention can be incorporated into pharmaceutical compositions suitable for administration. As used herein, a "modulator" of integrin activity, e.g., inhibitors and inducers, includes a compound that modulates an integrin activity, e.g., an integrin-mediated signaling event, an integrin-mediated adhesion event, or integrin binding to a cognate ligand. Integrin modulators include modified integrin I-domain or I-like domain polypeptides of the invention, anti-integrin I-domain polypeptides, as well as compounds identified in a screening assay described herein. Such compositions typically comprise the compound, nucleic acid molecule, vector, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media, and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, ophthalmic, and rectal administration, including direct installation into a disease site. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a soluble modified integrin I-domain fusion protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The administration of the active compounds of the invention may be for either a prophylactic or therapeutic purpose. Accordingly, in one embodiment, a "therapeutically effective dose" refers to that amount of an active compound sufficient to result in a detectable change in the physiology of a recipient patient. In one embodiment, a therapeutically effective dose refers to an amount of an active compound sufficient to result in modulation of an inflammatory and/or immune response. In another embodiment, a therapeutically effective dose refers to an amount of an active compound sufficient to result in the amelioration of symptoms of an inflammatory and/or immune system disorder. In another embodiment, a therapeutically effective dose refers to an amount of an active compound sufficient to prevent an inflammatory and/or immune system response. In yet another embodiment, a therapeutically effective dose refers to that amount of an active compound sufficient to modulate an integrin activity (e.g., a signaling activity, an adhesion activity or a ligand binding activity) as described herein.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of antibody, protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. Ranges intermediate to the above recited values, also are intended to be part of this invention. For example, ranges of span values using a combination of any of the above recited values as upper and/or lower limits are intended to be included.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

In another preferred example, a subject is treated with an initial dosing of a therapeutically effective amount of an anti-integrin antibody, e.g., an anti-integrin antibody, e.g., an anti-LFA-1 antibody, which reacts with or binds to an I-domain of an integrin in the open or active conformation, or an anti-integrin antibody, e.g., an anti-LFA-1 antibody, which reacts with or binds to a modified LFA-1 I-domain, followed by a subsequent intermittent dosing of a therapeutically effective amount of the antibody that is less than 100%, calculated on a daily basis, of the initial dosing of the antibody wherein the antibody is administered not more than once per week during the subsequent dosing. In another embodiment, the subsequence dosing is two or more times per week. In another embodiment, the subsequence dosing is one or more time every two weeks. In still another embodiment, the subsequence dosing is one or more times every three weeks. In yet another embodiment, the subsequence dosing is one or more times every four weeks. In one embodiment, the subsequent dosing is less than about 50%, 45%, 40%, 35%, 30%, 25%, 20%, 15%, 10%, 9%, 8%, 7%, 6% 3%, 2%, or 1%, calculated on a daily basis, of the initial dosing of the antibody. In one embodiment, the initial dosage is between 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. In a preferred embodiment, the initial dosage is less than 0.3 mg/kg body weight, e.g., between 0.001 to 0.30, e.g., 0.1, 0.125, 0.15, 0.175, 0.2, 0.225, 0.25, and 0.275. Ranges intermediate to the above recited values, also are intended to be part of this invention.

In yet another example, a subject is treated with an initial dosing of a therapeutically effective amount of an anti-integrin antibody, e.g., an anti-integrin antibody, e.g., an anti-LFA-1 antibody, which reacts with or binds to an I-domain of an integrin in the open or active conformation, or an anti-integrin antibody, e.g., an anti-LFA-1 antibody, which reacts with or binds to a modified LFA-1 I-domain, followed by a subsequent intermittent dosing of a therapeutically effective amount of the antibody that is greater than 100%, calculated on a daily basis, of the initial dosing of the antibody wherein the antibody is administered to the mammal not more than once per week during the subsequent dosing. In another embodiment, the subsequence dosing is two or more times per week. In another embodiment, the subsequence dosing is one or more time every two weeks. In still another embodiment, the subsequence dosing is one or more times every three weeks. In yet another embodiment, the subsequence dosing is one or more times every four weeks. In one embodiment, the initial dosage is between 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. In a preferred embodiment, the initial dosage is less than 0.3 mg/kg body weight, e.g., between 0.001 to 0.3, e.g., 0.1, 0.125, 0.15, 0.175, 0.2, 0.225, 0.25, and 0.275. Ranges intermediate to the above recited values, also are intended to be part of this invention. Dosages for anti-integrin antibodies, e.g., anti-LFA-1 are described in, for example, U.S. Pat. No. 5,622,700.

In still another example, an initial dosage is followed by the same dosage, for example, not more than once per week during the subsequent dosing. In another embodiment, the subsequence dosing is two or more times per week. In another embodiment, the subsequence dosing is one or more time every two weeks. In still another embodiment, the subsequence dosing is one or more times every three weeks. In yet another embodiment, the subsequence dosing is one or more times every four weeks.

Dosages for anti-integrin antibodies, e.g., anti-LFA-1 are described in, for example, U.S. Pat. No. 5,622,700.

In another embodiment, the an effective amount of an anti-inflammatory or immunosuppressive agent to the mammal in combination with the antibody, either at the same time, or at different time points.

The present invention encompasses active agents which modulate an integrin activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of integrin activity is administered in combination with other agents (e.g., a small molecule), or in conjunction with another, complementary treatment regime. For example, in one embodiment, an inhibitor of integrin activity is used to treat an inflammatory or immune system disorder. Accordingly, the subject may be treated with an inhibitor of integrin activity, and further treated with an anti-inflammatory or immunosuppressive agent.

Further, an antibody, e.g., an anti-LFA-1 antibody, (or fragment thereof) may be conjugated to a therapeutic moiety such as a cytotoxin, a therapeutic agent or a radioactive metal ion. The conjugates of the invention can be used for modifying a given biological response, and the drug moiety is not to be construed as limited to classical chemical therapeutic agents; For example, the drug moiety may be a protein or polypeptide possessing a desired biological activity. Such proteins may include, for example, a coagulation factor such as tissue factor; a protein such as vascular endothelial growth factor ("VEGF"), platelet derived growth factor, and tissue plasminogen activator; biological response modifiers such as, for example, lymphokines, cytokines and growth factors; or a toxin.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (.sub.2.sup.nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules of the invention, e.g., a nucleic acid molecule encoding, for example, a high-affinity modified integrin I-domain polypeptide, or active fragment thereof, can be used as a gene-based therapy alone, or, can be inserted into vectors and used as gene therapy vectors. Gene therapy is the insertion of a functioning gene into the cells of a patient (i) to correct an inborn error of metabolism, or (ii) to provide a new function in a cell (Kulver, K. W., "Gene Therapy", 1994, p. xii, Mary Ann Liebert, Inc., Publishers, New York, N.Y.). Vectors, e.g., viral vectors, may be used to introduce and stably express a gene normally expressed in mammals, for example, in a location in the body where that gene is not naturally present. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The gene therapy vector can include, for example, DNA encoding an antigen of interest to induce an immune response in the subject in vivo. Therefore, the modified integrin I-domain polypeptide, e.g., a high-affinity modified integrin I-domain polypeptide, or active fragment thereof, acts as an adjuvant to produce an increased antibody reaction to the antigen. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The nucleic acid molecules of the invention can also be used in DNA vaccine formulations for therapeutic or prophylactic treatment of integrin-mediated disorders, e.g., inflammatory disorders. In one embodiment, the DNA vaccine formulation comprises a nucleic acid molecule encoding a modified integrin polypeptide, e.g., a modified integrin I-domain polypeptide, or fragment thereof, coupled with an antigenic component, e.g., DNA encoding an antigenic component. As used herein, an antigenic component is a moiety that is capable of binding to a specific antibody with sufficiently high affinity to form a detectable antigen-antibody complex. In another embodiment, the DNA vaccine further comprises a pharmaceutically acceptable carrier.

The pharmaceutical compositions can be included in a container, pack, or dispenser together with instructions for administration.

Methods of Treatment

The present invention provides for both prophylactic and therapeutic methods of treating a subject at risk of an integrin-mediated disorder or having an integrin-mediated disorder such as an inflammatory or immune disorder, and/or a cellular proliferative disorder. "Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, nucleic acid molecules, DNA vaccines, gene-based therapies, small molecules, peptides, antibodies, e.g., anti-LFA-1 antibodies, which react with or bind to modified I-domain polypeptides, ribozymes and antisense oligonucleotides.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient' genes determine his or her response to a drug (e.g., a patient "drug response phenotype", or "drug response genotype"). Thus, another aspect of the invention provides methods for tailoring an individual' prophylactic or therapeutic treatment with either the integrin I-domain polypeptides of the present invention or modulators thereof according to that individual' drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject a disease or condition associated with a integrin-mediated disorder by administering to the subject one or more integrin I-domain polypeptides of the present invention or modulators thereof. Subjects at risk for an integrin-mediated disorder can be identified by, for example, any or a combination of diagnostic or prognostic assays as described herein. Administration of a prophylactic agent can occur prior to the manifestation of symptoms characteristic of the integrin-mediated disorders, such that a disease or disorder is prevented or, alternatively, delayed in its progression. Depending on the type of integrin-mediated disorder, for example, appropriate integrin I-domain polypeptides of the present invention, or modulators thereof, can be used for treating the subject. The appropriate agent can be determined based on screening assays described herein.

2. Therapeutic Methods

Another aspect of the invention pertains to methods of modulating expression of integrin I-domain polypeptides or their activity for therapeutic purposes (e.g., treating a subject at risk of an integrin-mediated disorder or having an integrin-mediated disorder such as an inflammatory or immune disorder, and/or a cellular proliferative disorder). Accordingly, in an exemplary embodiment, the modulatory method of the invention involves contacting a cell with one or more integrin I-domain polypeptides of the present invention, or one or more modulators thereof, e.g., an antibody which reacts of binds to an integrin I-domain in an open conformation or a modified integrin I-domain polypeptide, e.g., an anti-LFA-1 antibody specific for an LFA-1 I-domain in an open conformation or a modified LFA-1 I-domain polypeptide. An agent that modulates integrin I-domain polypeptide activity can be an agent as described herein, such as a nucleic acid or a protein, a target molecule of an integrin I-domain polypeptide (e.g., a substrate), an antibody which reacts or binds to a modified integrin I-domain polypeptide, an integrin I-domain polypeptide agonist or antagonist, a peptidomimetic of an integrin I-domain polypeptide agonist or antagonist, or other small molecule. In one embodiment, the agent stimulates one or more integrin I-domain polypeptide activities.

Examples of such stimulatory agents include active integrin I-domain polypeptide protein and a nucleic acid molecule encoding integrin I-domain polypeptide that has been introduced into the cell. In another embodiment, the agent inhibits one or more integrin I-domain polypeptide activities. Examples of such inhibitory agents include antisense integrin I-domain polypeptide nucleic acid molecules, gene therapy vectors, DNA vaccines, anti-integrin I-domain polypeptide antibodies, and integrin I-domain polypeptide inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized associated with an integrin-mediated disorder. In one embodiment, the method involves administering an agent (e.g., an agent identified by a screening assay described herein), or combination of agents that modulates (e.g., upregulates or downregulates) integrin I-domain polypeptide expression or activity.

3. Pharmacogenomics

The integrin I-domain polypeptide molecules of the present invention, as well as agents, or modulators which have a stimulatory or inhibitory effect on integrin I-domain polypeptide activity (e.g., integrin I-domain polypeptide gene expression) as identified by a screening assay described herein can be administered to individuals to treat (prophylactically or therapeutically) an integrin-mediated disorder such as an inflammatory or immune disorder, and/or a cellular proliferative disorder. In conjunction with such treatment, pharmacogenomics (i.e., the study of the relationship between an individual' genotype and that individual' response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an integrin I-domain polypeptide molecule (and/or a modulator thereof) as well as tailoring the dosage and/or therapeutic regimen of treatment with such molecule and/or modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (antimalarials, sulfonamides, analgesics, nitroflirans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SN.beta. may occur once per every 1000 bases of DNA. A SN.beta. may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., an integrin I-domain polypeptide molecule or integrin I-domain polypeptide modulator) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an integrin I-domain polypeptide molecule or modulator thereof, such as a modulator identified by one of the exemplary screening assays described herein.

This invention is further illustrated by the following examples which should not be construed as limiting. The contents of all references, patents and published patent applications cited throughout this application, as well as the figures and sequence listing are incorporated herein by reference.

EXAMPLES

Example 1

Design of LFA-1 and Mac-1 Mutants that are Locked in Open or Closed Conformation Current crystal and NMR structures of the LFA-1 I domain (Qu, A and Leahy, D J (1995) Proc Natl Acad Sci USA 92:10277-1028 1; Qu, A and Leahy, D J (1996) Structure 4:931-942; Kallen, J et al. (1999) J Mol Biol 292:1-9) have a conformation that is similar to the low affinity, closed conformer of the Mac-1 I domain (Ulm) (Lee, J-O et al. (1995) Cell 80:631-638). Therefore, the high affinity, open conformer of the Mac-1 I domain (1ido) (Lee, J-O et al. (1995) Structure 3:1333-1340) was used to model a high affinity, open LFA-1 I domain. The template for this model consisted of segments of the 1ido structure in regions where the Cα backbone differed significantly from the 1jlm structure, and segments of the 1lfa structure in regions where 1ido and 1jlm were similar.

Briefly, I domains with the following protein data bank (PDB) identifiers were structurally superimposed using C.alpha. carbons, the CD MALIGN algorithm of MODELLER 4 (Sali, A and Blundell, T L (1993) J Mol Biol 234:779-815), and a gap extension penalty of 1 .ANG.: Mac-1, 1ido and 1jlm (Lee, J-O et al. (1995) Structure 3:1333-1340; Lee, J-O et al. (1995) Cell 80:631-638); LFA-1, 1lfa molecules A and B (Qu, A and Leahy, D J (1995) Proc Natl Acad USA 92:10277-10281), 1zon and 1zop (Qu, A and Leahy, D J (1996) Structure 4:931-942); and VLA-2, 1aox (Emsley, J et al. (1997) J Biol Chem 272:28512-28517). The algorithm found 121 framework residues that were utilized for superposition. A sequence alignment was then done. The 1ido and 1jlm structures were aligned by their sequence, and 1lfa molecule A and 1zon were aligned by structural similarity to 1jlm. Using the structural superposition, and the sequence alignment, the distances between all Cα carbons at equivalent sequence positions were calculated using a Microsoft Excel spreadsheet. This was analogous to the comparison between 1jlm and 1ido (Lee, J-O et al. (1995) Structure 3:1333-1340), except that LFA-1 I domain structures were included. For use as templates for the high affinity, open LFA-1 I domain model, segments from 1lfa molecule A were chosen where differences between all four I domains were small, or differences between 1lfa and 1jlm (low affinity, closed LFA-1 and Mac-1 I domains) were greater than between 1ido and 1jlm (open and closed Mac-1 I domains). Segments from 1ido were chosen when differences between 1ido and 1jlm were greater than between 1lfa and 1jlm. These segments were spliced together in regions where the backbones were as similar as possible. Thus, the template utilized segments G128 to F136, M154 to L203, F209 to L234, T243 to 1255, and E272 to A282 of 1lfa; and segments D140 to F156, G207 to T211, V238 to K245, R266 to R281, and R293 to K315 of 1ido. No chain breaks were detected by LOOK™ (Molecular Application Group, Palo Alto, Calif.) in the spliced template, dubbed lfa-mac. Models of a high affinity open form of LFA-1 were made with MODELLER 4™ using this template, the $Mg^{2+}$ and water molecules 403 and 404 of 1ido, with heteroatom, water, and hydrogen input turned on, and dynamic Coloumb turned on. The resulting model ($^{lfa.sub.}$13 hi.063) followed the template C.alpha. coordinates closely (RMS=0.12 .ANG.). The QUACHK score (Vriend, G (1990) J Mol Graph 8:52-56) is excellent (−0.135 compared to 0.215 for the lfa-mac template, −0.08 for 1ido, and 0.0 for 1lfa).

The SSBOND program (Hazes, B and Dijkstra, B W (1988) Protein Engineering 2:119-125) was used to identify positions where disulfide bonds could be introduced by mutating two appropriately positioned pairs of residues to cysteine. It was hypothesized that it might be possible to use disulfide bonds to trap the LFA-1 I domain in either the open or closed conformations.

The high affinity open LFA-1 I domain model (the lfa_hi.063 model) was examined and two low affinity closed LFA-1 I domain structures, 1lfa and 1zon, with SSBOND and found 14 to 19 pairs of such residues in each structure. Out of these, one pair of residues in the high affinity open model, and one pair of residues in the low affinity closed structures, underwent large movements between the two conformers, such that disulfide bond formation could only occur in one conformer (FIG. 1). These disulfides bridge .beta.-strand 6 to the C-terminal .alpha.-helix, α6. The numbering of β-strands and α-helices differs among I domains; we use a uniform nomenclature (Huang, C et al. (2000) J Biol Chem, 275: 21514-24). Helix α6 moves 10 .ANG. along its axis down the body of the I domain in the high affinity open structure, and this movement is accompanied by a complete remodeling and downward shift of the loop between β6 and α6. Cysteines introduced in place of K287 and K294 were predicted to form a disulfide only in the high affinity open conformer, and thus lock the I domain in the high affinity open state (FIG. 2). The Cβ carbons of K287 and K294 are predicted to be 3.8 .ANG. apart in the high affinity open model (lfa.sub.13 hi.063), within the range of 3.41 to 4.25 .ANG. that is ideal for disulfide formation, and after checking for Cβ-Sγ and Sγ-Sγ distances, were found to have four favorable sidechain-disulfide conformations. By contrast, in the low affinity closed conformers 1lfa and 1zon, the Cβ atoms of these residues are 8.9 to 9.2 .ANG. apart (FIG. 2).

Cysteines introduced in place of L289 and K294 were predicted to form a disulfide only in the low affinity closed conformer (FIG. 2), and thus lock the I domain in the low affinity closed state. The Cβ carbons of L289 and K294 are 3.9 to 4.0 .ANG. apart in the low affinity closed 1lfa and 1zon conformers, within the favorable range, although favorable cysteine sidechain conformations were not found. Nonetheless, the α-helix in which residue 294 is present shows small displacements between 1lfa, 1zon, and the recent NMR structure (Qu, A and Leahy, D J (1995) Proc Natl Acad USA 92:10277-10281; Qu, A and Leahy, D J (1996) Structure 4:931-942; Kallen, J et al. (1999) J Mol Biol 292:1-9), and it was expected that a disulfide could form with minor adjustment of the α-helix. By contrast, in the high affinity open model, the Cβ atoms of these residues are predicted to be 8.0 .ANG. apart (FIG. 2).

Models were also built in which the predicted cysteines were present and disulfide bonds were formed if appropriate using the PATCH DISULFIDE routine of MODELLER 4 (FIG. 2); however, it should be noted that all Cβ atom distances reported here are based on models or structures without introduced disulfides.

In addition to the computational search for pairs of cysteine substitutions to form conformation-specific disulfide bridge, the structure-oriented manual approach (or visual inspection) was also used. Regions of I domains that differ in conformation between the open and closed conformations were inspected for positions in which pairs of cysteines could be introduced that would form disulfides that would favor one conformation over the other. Thus, the region of the conformationally mobile C-terminal α-helix and the preceding loop were examined for positions in which one cysteine could be introduced, and structurally adjacent regions were searched for positions where a second cysteine could be introduced that would form a disulfide bond. Pairs of residues whose sidechains face towards one another were chosen. The distance between the Cα and Cβ atoms of each of these pairs was measured by software Look™ both in the open and closed conformation. The ideal separation for cysteine Cβ carbons for formation of a disulfide bond is reported to be 3.41 to 4.25. However, the crystal structures or models from which these were measured represent average positions of snapshots, whereas proteins are dynamic and exhibit atomic mobility. Furthermore, structural adjustments are possible to accommodate disulfide bonds. Much more adjustment is expected to be possible in loops and α-helices than in β-sheets. Therefore greater distances were predicted to be allowable for disulfide formation when one of the residues was in a loop or helix.

For αL, 4 pairs of cysteine substitutions were found where the Cα-Cα and Cβ-Cβ distances were more favorable for disulfide formation in the open conformation than in the closed conformation; E284C/E301C, L161C/F299C, K160C/F299C, and L161C/T300C (Table 1).

For αM, 4 pairs of cysteine substitutions were found where the Cα-Cα and Cβ-Cβ distances were more favorable for disulfide formation in the open conformation than in the closed conformation: Q163C/Q309C, Q298C/N301C, D294C/T307C, and D294C/Q311c (Table 7), and one pair of cysteine substitutions where the Cα-Cα and Cβ-Cβ distances were more favorable for disulfide formation in the closed conformation than in the open conformation: Q163C/R313c. Additionally, F297C/A304C, which is an analogous mutation to K287C/K294C in αL, was included.

Example 2

Construction and Expression of LFA-1 Cysteine Substitution Mutants

Five open αL I-domain mutants were generated. To generate the high affinity open mutant K287C/K294C, the K287 and K294 in the I-domain of the αL subunit were replaced by cysteines. To generate the high affinity open mutant E284C/E301C, the E284 and E301 in the I-domain of the αL subunit were replaced by cysteines. In addition, three intermediate-affinity open αL I-domain mutants were made, and are identified herein as follows: L161C/F299C, K160C/F299C, and L161C/T300C. L161C/F299C was made by substituting cysteines for the L161 and F299. K160C/F299C was made by substituting cysteines for the K160 and F299. L161C/T300C was made by substituting cysteines for the L161 and T300. The low affinity closed mutant L289C/K294C was made by substituting cysteines for the L289 and K294. The distance between mutated residues for these six mutant is shown in Table 1, below. Also, single cysteine substitution mutants K287C, L289C and K294C were generated.

TABLE 1

Cα and Cβ between mutated residues in either open or closed confirmation

| αL I-domain | Open conformation | | Closed conformation | |
|---|---|---|---|---|
| | Cα (A) | Cβ (A) | Cα (A) | Cβ (A) |
| Locked open | | | | |
| K287C/K294C | 6.32 | 3.75 | 10.72 | 9.08 |
| E284C/E301C | 9.12 | 6.96 | 12.88 | 12.52 |
| L161C/F299C | 9.16 | 8.09 | 11.87 | 11.38 |
| K160C/F299C | 9.97 | 7.75 | 9.83 | 7.96 |
| L161C/T300C | 12.30 | 13.00 | 13.50 | 14.87 |
| Locked closed | | | | |
| L289C/K294C | 7.90 | 7.96 | 6.19 | 3.86 |

The distance between wild-type residues was measured by Look™ software in open conformation (lfa_hi.063) or closed conformation (1lfaA).

The human αL cDNA was contained in vector AprM8, a derivative of CDM8 (Seed, B and Aruffo, A (1987) Proc Natl Acad Sci USA 84:3365-3369). Overlap extension PCR was used to generate cysteine substitution mutations in the αL I-domain (Ho, S N et al. (1989) Gene 77:51-59; Horton, R M et al. (1990) BioTechniques 8:528).

The outer left primer for PCR extension was complementary to the vector sequence at 5' to the EcoRI site at position 1826, and the outer right primer was 3' to the EcoRI site in the αL cDNA. The inner primers were designed for each individual mutation and contained overlapping sequences. Wild-type αL cDNA in AprM8 was used as template for the first PCR reaction. The second PCR product was digested with EcoRI and ligated into the same site in the wild-type αL cDNA in AprM8. The correct orientation of the insert was confirmed by restriction enzyme digestion. All mutations were confirmed by DNA sequencing.

For stable expression, the XbaI fragment of αL wild-type and mutant cDNA was subcloned into the same site of the stable expression vector pEFpuro (Lu, C and Springer T A., (1997) J Immunol 159:268-278).

The mutated αL subunit was transiently coexpressed with the β2 subunit in 293T cells, and cell surface expression of the αL/β2 complex was determined by flow cytometry with monoclonal antibody TS2/4 to the αL subunit in the αLβ2 complex.

Briefly, human embryonic kidney 293T cells (SV40 transformed) were cultured in DMEM medium supplemented with 10% fetal bovine serum (FBS), 2 mM glutamine and 50 .mu.g/ml gentamycin. 293T cells were transiently transfected using the calcium phosphate method (DuBridge, R B et al. (1987) Mol Cell Biol 7:379-387; Heinzel, S S et al. (1988) J Virol 62:3738-3746). Briefly, 7.5 .mu.g of wild-type or mutant αL cDNA in plasmid AprM8 and 7.5 .mu.g of β2 cDNA in AprM8 were used to co-transfect one 6-cm plate of 70-80% confluent cells. Two days after transfection, cells were detached from the plate with Hanks' balanced salt solution (HBSS) containing 5 mM EDTA for LFA-1 expression and functional analyses.

Flow cytometric analysis was performed as previously described (Lu, C and Springer T A, (1997) J Immunol 159: 268-278). Briefly, cells were washed and resuspended in L15 medium (Sigma) supplemented with 2.5% FBS (L15/FBS). $1 \times 10 \times 10^5$ cells were incubated with primary antibodies in 100 μL15/FBS on ice for 30 min. Monoclonal antibodies were used at final concentration of 1:20 hybridoma supernatant, 1:200 ascites, or 10 μg/ml purified IgG. Cells were then washed twice with L15/FBS, and incubated with FITC-conjugated goat anti-mouse IgG (heavy and light chain, Zymed Laboratories, San Francisco, Calif.) for 30 min on ice. After washing, cells were resuspended in cold PBS and analyzed on a FACScan (Becton Dickinson, San Jose, Calif.).

As shown in FIG. 3A, the predicted high and low affinity mutants, and the single cysteine substitution mutants expressed similar levels of cell surface αL/β2 complex.

To test whether introducing the cysteines affected the overall conformation of the I-domain, a panel of monoclonal antibodies to different regions in the I-domain were tested for their reactivity with the I-domain mutants. The monoclonal antibodies used in these studies are as follows:

The mouse anti-human αL (CD11a) monoclonal antibodies TS1/11, TS1/12, TS1/22, TS2/4, TS2/6 and TS2/14; anti-β2 (CD18) monoclonal antibodies TS1/18, CBRLFA-1/2, and CBRLFA-1/7; mAb YFC51; and the nonbinding mAb X63 have been described previously (Sanchez-Madrid, F et al. (1982) Proc Natl Acad USA 79:7489-7493; Hale, Lβ et al. (1989) Arthritis Rheum 32:22-30; Petruzzelli, L et al. (1995) J Immunol 155:854-866). Monoclonal antibodies BL5, F8.8, 25-3-1, May.035, CBRLFA-1/9, CBRLFA-1/1, S6F, and May.017 were described in Leukocyte Type V and were obtained from the Fifth International Leukocyte Workshops.

Monoclonal antibodies X63 and TS1/11 were used as hybridoma supernatants at a 1:20 dilution; monoclonal antibodies TS1I/12, DBRLFA-1/2, CBRLFA-1/7 and YFC51 were used as purified IgG at 10 μg/ml; monoclonal antibodies TS1/2, TS2/14, TS1/18 and TS2/4 used as ascites at a 1:200 dilution; and all monoclonal antibodies from the Fifth International Leukocyte Workshops were used at a 1:200 dilution. All of the antibodies, except for CBRLFA-1/1, bound to the mutants K287C/K294C and L289C/K294C and wild-type LFA-1 equally well (Table 2), indicating that the cysteine substitutions did not disrupt the I-domain structure. Binding of monoclonal antibody CBRLFA-1/1 to the high-affinity open mutant K287C/K294C was reduced to 40-50% of wild-type, however, this antibody reacted with mutant L289C/K294C and the single cysteine substitution mutants K287C, L289C and K294C as well as wild-type. Since antibody CBRLFA-1/1 maps to residues 301-359 (Huang, C and Springer T A, (1995) J Biol Chem 270:19008-19016), and single Cys substitution for K287 and K294 did not affect binding of this antibody, it is likely that reduced binding of CBRLFA-1/1 to mutant K287C/K294C was an indirect effect. Therefore, the conformation at the interface between the I- and β-propeller domains in mutant K287C/K294C may be different from that in wild-type LFA-1.

The reactivity of antibody to the β-propeller domain of αL and to the β subunit with mutants K287C/K294C and L289C/K294C was similar to that of wild-type LFA-1, confirming that the structure of other domains of LFA-1 molecule was not affected by the mutations.

K294C did not bind to ICAM-1. Whereas the single cysteine substitution mutants K287C and L289C exhibited reduced binding to ICAM-1, binding of mutant K294C was comparable to that of the wild-type. Binding of mutants K287C and L289C was increased by the activating monoclonal antibody CBRLFA-1/2 to a level similar to wild-type binding. However, CBRLFA-1/2 was not able to activate binding of the low-affinity closed mutant L289C/K294C to ICAM-1 (FIG. 4A). Similar results were obtained with two other LFA-1 activating monoclonal antibodies Kim127 and Kim185. To further study the function of the predicted high affinity mutant K287C/K294C and low affinity closed mutant L289C/K294C, stable K562 transfectants that express these mutants were generated.

Briefly, the human erythroleukemia cell line K562 was cultured in RPMI 1640, 10% FBS and 50 μg/ml gentamycin. For generating stable K562 cell lines, 2 μg of PvuI-linearized pEFpuro containing αL subunit cDNA was cotransfected with 40 μg of SfiI-linearized AprM8 containing the β subunit cDNA by electroporation at 250V and 960 μF. Transfectants were selected for resistance to 4 μg/ml puromycin (Sigma), and subcloned by limiting dilution. All stable cell lines were maintained in RPMI 1640, 10% FBS supplemented with 4 μg/ml puromycin.

TABLE 2

Reactivity of antibodies with LFA-1 cysteine substitution mutants (% wild-type binding)

| Mab | Epitope | K287C/K294C | | L298C/K294C | | K287C | L289C | K294C |
|---|---|---|---|---|---|---|---|---|
| | | 293T | K562 | 293T | K562 | 293T | 293T | 293T |
| | I-domain | | | | | | | |
| BL5 | 119-153, 185-215 | 92.4 ± 11.29 | 92.39 | 85.79 ± 16.4 | 97.61 | 93.35 | 92.44 | 88.31 |
| F8.8 | 119-153, 185-215 | 93.70 | 102.15 | 83.56 | 93.88 | 95.86 | 99.63 | 95.47 |
| CBRLFA-1/9 | 119-153, 185-215 | ND | 84.7 | ND | ND | ND | ND | ND |
| TS2/6 | 154-183 | 84.88 ± 5.64 | 89.24 | 78.59 ± 2.62 | 95.89 | 91.39 | 88.24 | 91.67 |
| May.035 | 185-215 | 92.61 ± 8.4 | 92.59 | 82.14 ± 14.15 | 101.10 | 95.8 | 95.4 | 106.39 |
| TS1/11 | 185-215 | 94.36 | 95.96 | 93.67 | 104.54 | ND | ND | ND |
| TS1/12 | 185.215 | 88.66 | 87.32 | 101.98 | 105.63 | 99.32 | 103.89 | 93.68 |
| TS1/22 | 185-302 | 95.85 ± 12.04 | 93.06 | 90.96 ± 8.11 | 110.49 | 102.99 | 96.21 | 92.24 |
| TS2/14 | 250-303 | 85.54 ± 9.38 | 95.41 | 83.31 ± 10.59 | 102.85 | 102.6 | 100.4 | 102.83 |
| 25-3-1 | 250-303 | 93.06 | 88.48 | 90.93 | 85.66 | ND | ND | ND |
| CBRLFA-1/1 | 1- Andβ-propeller | 43.59 ± 0.58 | 55.53 | 95.89 ± 7.74 | 118.44 | 86.11 | 93.32 | 89.41 |
| S6F1 | B-propeller | 89.39 | 97.38 | 95.32 | 85.69 | 98.3 | 86.39 | 92.34 |
| | B2 subunit | | | | | | | |
| TS1/18 | I-like domain | 99.82 ± 10.47 | 97.42 | 95.72 ± 4.67 | 105.71 | 87.88 | 87.35 | 107.58 |
| YFC51 | I-like domain | 102.63 | 100.73 | 95.09 | 110.96 | ND | ND | ND |
| CLBLFA-1/1 | I-like domain | ND | 96.48 | ND | 100.50 | ND | ND | ND |
| CBRLFA-1/7 | C-terminal region | 95.32 | 95.25 | 91.68 | 97.19 | ND | ND | ND |

Wild-type LFA-1 and LFA-1 mutant K287C/K294C, L289C/K294C, K287C, L289C, and K294C were transiently expressed on the surface of 293T cells or stably expressed on K562 transfectants.
Reactivity of antibodies with the transfectants was determined by flow cytometry.
Mean fluorescence of each antibody binding was normalized to the mean fluorescence of mAb TS2/4 binding, except for CBRLFA-1/9 that was normalized to mAb TS1/22 binding.
TS2/4 bound to wild-type LFA-1 and the mutants equally #well.
The results expressed as percent of wild-type binding.
Data are mean .+−.
SD of at least two independent FCAS experiments.
For some antibodies, only one experiment was done.
ND: not determined.

Example 3

Ligand Binding Activity of LFA-1 Cysteine Substitution Mutants

The ability of the LFA-1 cysteine substitution mutants to bind to the LFA-1 ligand ICAM-1 was determined. 293T cell transfectants that express wild-type LFA-1 and the predicted high-affinity open I-domain mutant K287C/K294C showed constitutively strong binding to immobilized ICAM-1 (FIG. 4A). By contrast, the low-affinity closed mutant L289C/

Clones of the transfectants that expressed similar levels of cell surface LFA-1, as determined by flow cytometry using monoclonal antibody TS2/4 (FIG. 3B), were tested for their ability to bind to immobilized ICAM-1, as previously described (Lu, C and Springer, T A (1997) J Immunol 159: 268-278).

Briefly, ICAM-1 was purified from human tonsil, and coated to 96-well plates as described previously (Lu, C and Springer T A, (1997) J Immunol 159:268-278). Cells were labeled with a florescence dye 2',7'-bis-(carboxyethyl)-5 (and-6)-carboxyfluorescein, acetoxymethyl ester (BCECF- AM), and resuspended to 1.times.10.sup.6/ml in L15/FBS. 50 µl cell suspension was mixed in ICAM-1 coated wells with an equal volume of L15/FBS in the absence or presence of monoclonal antibody (CBRLFA-1/2, 10 µg/ml). Monoclonal antibodies were used at final concentration of 1:20 hybridoma supernatant, 1:200 ascites, or µg/ml purified IgG. For testing the effect of divalent cations, BCECF-AM-labeled cells were washed 2× with TS buffer, pH7.5 (20 mM Tris, pH 7.5, 150 mMNaCl) containing 5 mM EDTA, followed by 2 washes with TS buffer, pH7.5. Cells were then resuspended to $5 \times 10^5$/ml in the TS buffer, pH7.5 supplemented with 1 mM $MgCl_2$/$CaCl_2$, $MgCl_2$, $MnCl_2$ mM EDTA, and 100 µl cell suspension was added to ICAM-1 coated wells. After incubation at 37° C. for 30 minutes, unbound cells were washed off on a Microplate Autowasher (Bio-Tek Instruments, Winooski, Vt.). The fluorescence content of total input cells and the bound cells in each well was quantitated on a Fluorescent Concentration Analyzer (IDEXX, Westbrook, Me.). The bound cells were expressed as a percentage of total input cells per sample well.

K562 transfectants that express wild-type LFA-1 showed low basal binding to ICAM-1, and binding was greatly increased by the activating monoclonal antibody CBRLFA-1/2 (FIG. 4B). By contrast, cells expressing the predicted high-affinity open mutant K287C/K294C strongly bound to ICAM-1, and monoclonal antibody CBRLFA-1/2 did not further enhance binding of this mutant, whereas the predicted low-affinity closed mutant L289C/K294C did not binding to ICAM-1 even in the presence of the activating antibody.

The effect of divalent cations on binding of K562 transfectants to ICAM-1 was also examined. As shown in FIG. 4C, binding of mutant K287C/K294C to ICAM-1 was abolished in the presence of EDTA, confirming that ligand binding of mutant K287C/K294C is divalent cation dependent. Whereas binding of wild-type LFA-1 was greatly enhanced by $Mn^{2+}$, and to a lesser degree by $Mg^{2+}$, the presence of $Mn^{2+}$ and $Mg^{2+}$ did not increase binding of the low-affinity closed mutant L289C/K294C to ligand.

The binding of soluble ICAM-1 to K562 transfectants that expressed wild-type LFA-1, mutant K287C/K294C, or mutant L289C/K294C was also assessed. Briefly, a soluble ICAM-1-IgA chimera containing the 5 Ig domains of human ICAM-1 was purified from the culture supernatant of stable CHO transfectants by monoclonal antibody R6.5 affinity chromatography as previously described (Martin, S et al. (1993) J Virol 67:3561-3568). K562 transfectants were washed once with L15/FBS, and resuspended in the same buffer to $1 \times 10^7$/ml. 25 µl cell suspension was mixed with 25 µL15/FBS containing ICAM-1-IgA fusion protein at final concentration 100 µg/ml in the presence or absence of antibody CBRLFA-1/2 (10 µg/ml), and incubated at 37° C. for 30 minutes. After incubation, cells were washed once in L15/FBS, and incubated with FITC-conjugated anti-human IgA (Sigma) at room temperature for 20 minutes. After 2 washes, cells were resuspended in PBS, and analyzed on a FACScan (Becton Dickinson, San Joe, Calif.).

Figure 5:
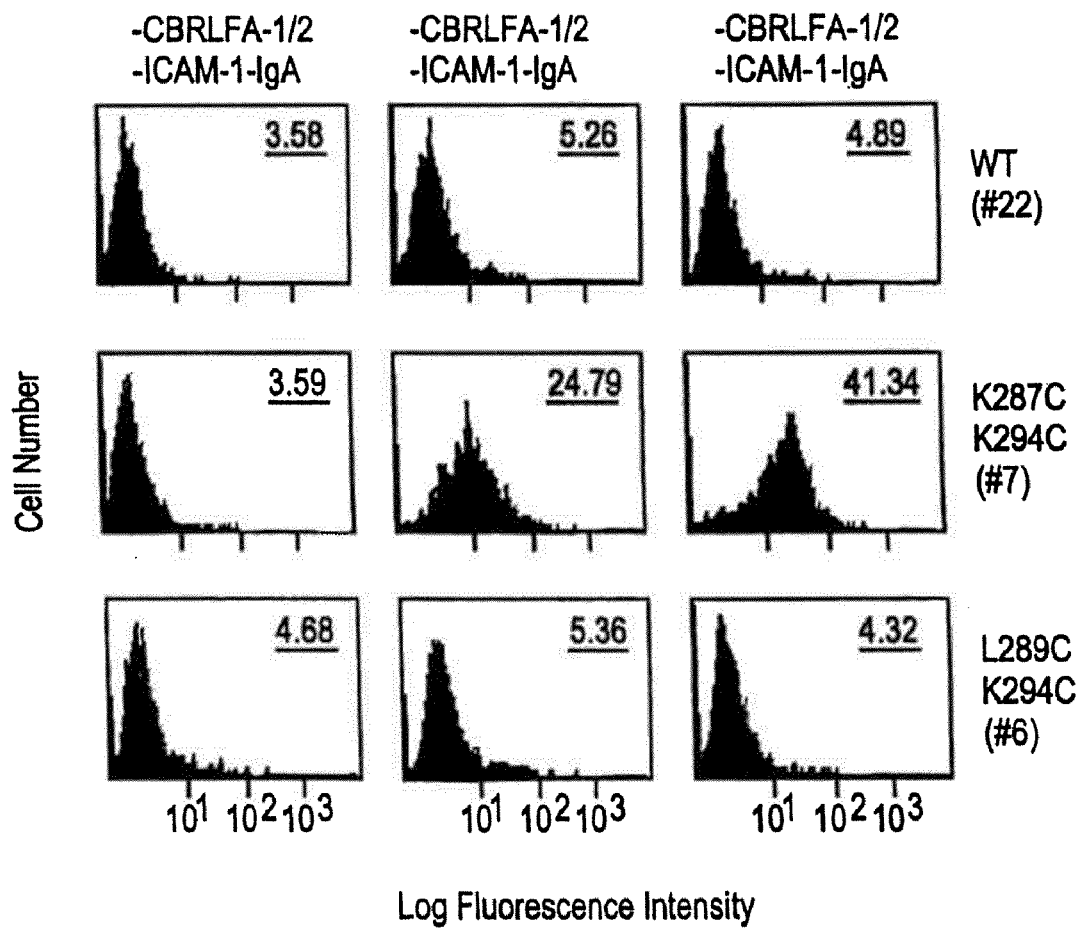
FIG. 5 depicts the binding of soluble ICAM-1-IgA fusion protein to K5 62 transfectants that express wild-type LFA-1, the predicted high-affinity mutant K287C/K294C, or mutant L289C/K294C as assessed by flow cytometric analysis. Mean fluorescent intensity of ICAM-1-IgA binding is indicated on the upper right corner of the histogram plot. Numbers in the parentheses are clone numbers of the K562 stable transfectants. Results are representative of three experiments.

As shown in FIG. 5, the soluble ICAM-1-IgA fusion protein bound to cells expressing the high-affinity open mutant K287C/K294C, and binding was further increased in the presence of the activating monoclonal antibody CBRLFA-1/2. However, the ICAM-1 fusion protein did not bind to the transfectants that expressed wild-type LFA-1 or the low affinity closed mutant L289C/K294C in the absence or presence of monoclonal antibody CBRLFA-1/2, and binding was not detected at a higher ICAM-1 fusion protein concentration (300 µg/ml).

Taken together these data indicate that the high affinity open mutant K287C/K294C is constitutively active, whereas the low-affinity closed mutant L289C/K294C appears to be locked in an inactive state and lacks ligand binding ability.

In another study, a panel of monoclonal antibodies to different domains of the αL and β subunits were tested for their inhibitory effect on ligand binding of wild-type LFA-1 and mutant K287C/K294C. The results obtained with the 293T transient transfectants and K562 stable transfectants were similar, and summarized in Table 3. Although all antibodies, except for CBRLFA-111, reacted with the high affinity open mutant K287C/K294C as well as wild-type (Table 2), they showed differential inhibition on ligand binding of wild-type LFA-1 and mutant K287C/K294C.

As shown in Table 3, the I-domain antibodies differentially inhibited binding of wild-type LFA-1 and the high affinity open mutant K287C/K294C to ICAM-1. Monoclonal antibodies BL5, F8.8, CBRLFA-1/9, May.035, TS1/22 and TS2/6 strongly inhibited binding of both wild-type and mutant K287C/K294C, and the levels of inhibition to wild-type LFA-1 and the mutant were similar. While monoclonal antibodies TS1/11 and TS1/12 inhibited >90% binding of transfectants that express wild-type LFA-1, these antibodies showed reduced inhibition on binding of mutant K287C/K294C (40-60%). Monoclonal antibodies TS2/14, 25-3-1 and CBRLFA-1/1 that showed >90% inhibition on binding of wild-type had no to little inhibition on mutant K287C/K294C binding to ICAM-1. While the β-propeller domain antibody S6F1 and TS2/4 and antibody CBRLFA-1/7 to the C-terminal region of the β subunit did not inhibit binding of both wild-type and mutant K287C/K294C, all five antibodies to the β2 conserved domain, TS1/18, YFC51, CLBLFA-1/1, May.017, and 6.5E, inhibited binding of wild-type LFA-1 (>90% inhibition), but did not inhibit binding of mutant K287C/K294C.

Antibodies to the β-propeller domain and to the C-terminal region of β did not inhibit binding of wild-type LFA-1, or mutant K287C/K294C. Antibodies to the I-like domain of the β subunit blocked binding of wild-type LFA-1 to ICAM-1, but did not block mutant K287C/K294C.

TABLE 3

Differential inhibition of antibodies on binding of wild-type LFA-1 and mutant K287C/K294C to immobilized ICAM-1

% inhibition

| MAb | Epitope | Wild-type LFA-1 | | K287C/K294C | |
|---|---|---|---|---|---|
| | | 293T | K562 (+CBRLFA-1/2) | 293T | K562 |
| RR1/1 | I-CAM-1 I-domain | 95.98 | ND | 97.89 | ND |
| BL5 | 119-153, 185-215 | 97.01 ± 1.63 | 97.54 | 91.06 ± 3.8 | 90.68 ± 6.23 |
| F8.8 | 119-153, 185-215 | 94.51 | 97.61 | 91.94 | 98.18 |

TABLE 3-continued

Differential inhibition of antibodies on binding of wild-type LFA-1 and mutant
K287C/K294C to immobilized ICAM-1

% inhibition

| MAb | Epitope | Wild-type LFA-1 | | K287C/K294C | |
|---|---|---|---|---|---|
| | | 293T | K562 (+CBRLFA-½) | 293T | K562 |
| CBRLFA-1/9 | 119-153, 185-215 | ND | 97.83 | ND | 3.60 |
| TS2/6 | 154-183 | 96.84 ± 1.73 | 91.76 ± 4.67 | 79.09 ± 10.06 | 88.12 ± 7.40 |
| May.035 | 185-215 | 96.20 ± 0.57 | 95.80 ± 1.66 | 97.43 ± 1.52 | 93.33 ± 2.54 |
| TS1/1 | 185-215 | 94.12 | 96.55 | 45.18 | 41.30 |
| TS1/1 | 185-215 | 95.68 ± 3.92 | 97.46 ± 0.66 | 48.96 ± 9.52 | 63.67 ± 8.13 |
| TS1/1 | 250-303 | 95.77 | 96.94 ± 0.79 | 95.07 | 93.56 ± 4.79 |
| TS2/14 | 250-303 | 94.47 ± 2.34 | 96.24 ± 1.70 | 2.95 ± 9.87 | 8.55 ± 0.66 |
| 25-3-1 | 250-303 | 90.49 | 92.01 ± 0.36 | 3.71 | 2.53 ± 4.10 |
| CBRLFA1/1 | I- and β-propeller | 92.52 ± 1.68 | 94.69 ± 5.22 | 9.03 | 2.85 ± 4.90 |
| S6F1 | B-propeller | ND | 6.19 | ND | 9.70 |
| TS2/4 | B-propeller B2 subunit | ND | 6.99 | ND | 2.82 |
| TS1/18 | I-like domain | ND | 98.48 | ND | 5.90 |
| YFC51 | I-like domain | ND | 98.43 | ND | 0.08 |
| CLBLFA-1/1 | I-like domain | ND | 94.63 | ND | 6.69 |
| May.017 | I-like domain | ND | 97.76 | ND | 2.98 |
| 6.5E | I-like domain | ND | 98.36 | ND | 5.79 |
| CBRLFA-1/7 | C-terminal region | ND | 5.04 | ND | 5.77 |

Wild-type LFA-1 and LFA-1 mutant K287C/K294C were transiently expressed on the surface of 293T cells or stably expressed in K562 transfectants.
Binding of the transfectants to immobilized ICAM-1 was determined in the presence of the indicated antibodies.
For binding of K562 transfectants that express wild-type LFA-1, the cells were preincubated with the activating mAb CBRLFA-½ at 10 .mu · g/ml for 30 min.
Data shown are % inhibition .+−.
SD of at least two # independent experiments.
% inhibition is defined as % bound cells in the presence of the indicated mAb/% bound cells in the presence of the nonbinding mAb X63 .times. 100.
For some antibodies, only one experiment was done. However, in each experiment, each antibody was repeated in triplicate, and the standard deviation of the triplicate samples was <5%.
ND: not determined Taken together, these results suggest that a subset of I-domain antibodies and antibodies to the β conserved domain do not directly block LFA-1 binding to ICAM-1, and that the high-affinity open mutant K287C/K294C appears to be conformationally locked in a high affinity open state, and thus, antibodies that block ligand binding via indirect mechanisms could not block binding of mutant K287C/K294C to ICAM-1.

The high affinity open I-domains of the invention can be used to discriminate between direct/competitive and indirect/non-competitive modes of inhibition of LFA-1. For example, the LFA-1 inhibitor lovastatin binds to the I-domain in a hydrophobic pocket formed by the β sheet and the C-terminal α-helix (Kallen, J et al. (1999) J Mol Biol 292:1-9) and thus inhibits LFA-1 by an indirect mechanism. Accordingly, the ability of lovastatin to inhibit ligand binding of the high-affinity I-domain (K287C/K294C) was assessed. Lovastatin dissolved in DMSO at 50 mM was diluted in assay buffer. Cells ($10^6$/ml) labeled with BCECF-AM were preincubated with lovastatin (0-50 μM) at 37° C. for 15 minutes, then transferred to a 96 well plate coated with ICAM-1 and further incubated at 37° C. for 30 minutes in the presence or absence of activating monoclonal antibody (CBR LFA1/2) or $MnCl_2$. L15 medium supplemented with fetal bovine serum (L15/FBS) which contains $Ca^{2+}$ and $Mg^{2+}$ was used for wild-type αL.β2 activated by antibody CBR LFA1/2. and 20 mM HEPES pH7.4, 140 mM NaCl, 1 mM MnCl12, 2 mg/ml glucose, 1% BSA was used for activation by $Mn^{2+}$.

Figure 6:
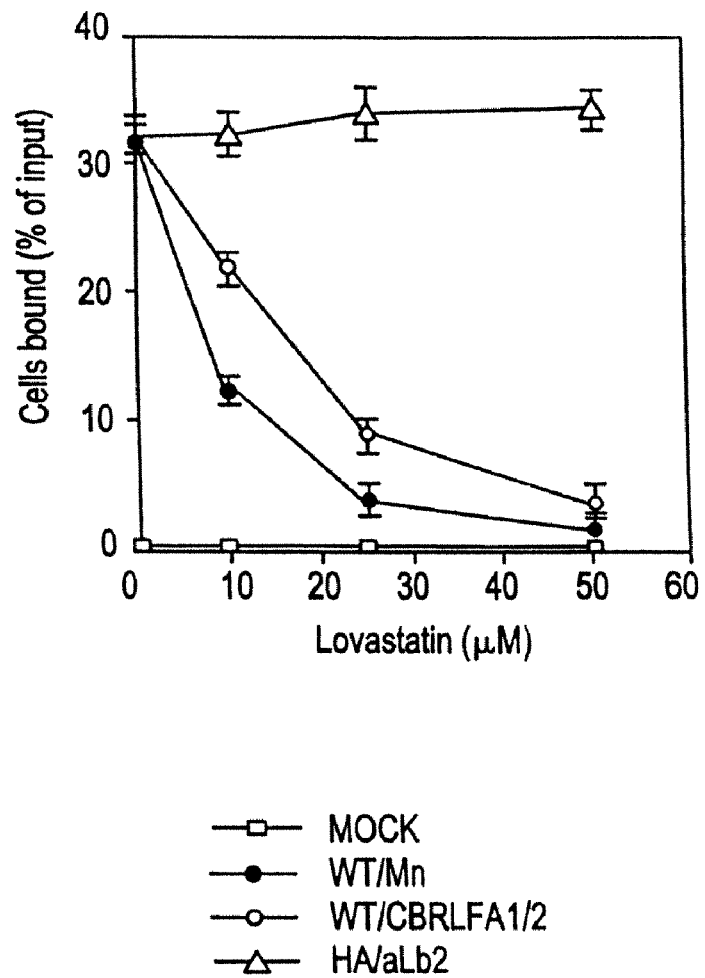
FIG. 6 depicts the inhibitory activity of lovastatin on ligand binding by cells expressing activated wild-type and high affinity (K287C/K294C) LFA-1.

As shown in FIG. 6, lovastatin inhibits ICAM-1 binding by cells expressing wild-type LFA-1 and stimulated with $Mn^{2+}$ or antibody (CBRLFA1/2), but does not interfere with ligand binding by the high affinity open K287C/K294C mutant (HA/aLb2).

Example 4

Expression and Function of Isolated Wild-Type and Mutant LFA-1 I-Domains

To further examine the function of the predicted high and low affinity mutants, the wild-type I-domain and the I-domains of mutant K287C/K294C and L289C/K294C from residues V130 to A338 were expressed on the surface of K562 cells by the transmembrane domain of the PDGF receptor.

To construct the isolated, cell-surface expressed I domains, DNA sequences that encode the signal peptide and the following 6 amino acids from the 5' end of repeat II of αL were ligated to the sequences encoding residues V1 30-A3 38 that contains the I domain. HindIII and SalI sites were introduced immediately adjacent to the 5' and 3' ends of this fragment, respectively. The HindIII-SalI fragment was subcloned in frame at the 5' to the c-myc tag and the PDGF receptor (PDGFR) transmembrane domain in vector pDisplay™ (Invitrogen), and further subcloned into pcDNA3.1/Hygro using HindIII and NotI. All DNA amplification was carried out with Pfu DNA polymerase (Stratagene), and the final constructs were verified by DNA sequencing.

Figure 7:
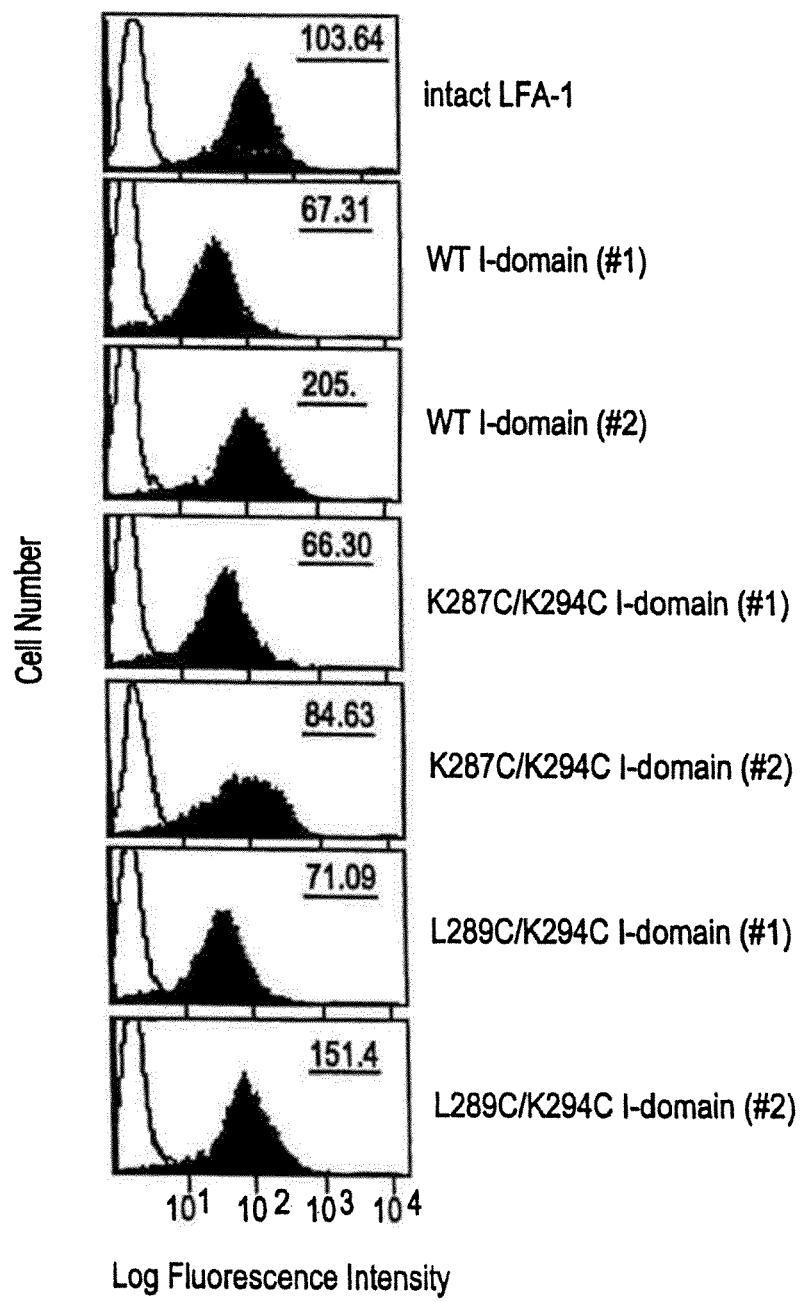
FIG. 7 depicts the cell surface expression of the isolated LFA-1 I-domains. The wild-type αL I-domain and the mutant K287C/K294C and L289C/K294C I-domains were expressed on the surface of the K562 transfectants by the PDGFR transmembrane domain. The level of cell surface I-domain was determined by flow cytometry using monoclonal antibody TS1/22 to the I-domain (shaded histogram). Binding of the control mAb X63 is shown as open histograms. Mean fluorescent intensity of TS 1/22 binding was indicated on the upper right corner of the histogram plot. Results of two individual clones (#1 and #2) from each I-domain transfectants are shown.
Figure 8A:
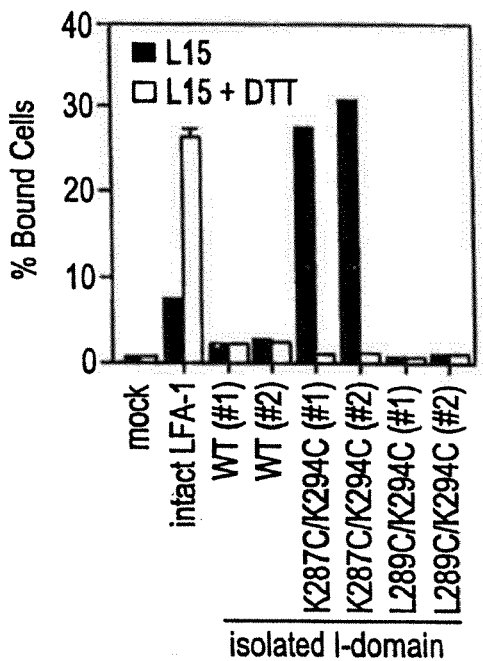
FIG. 8 depicts the ligand binding activity of the cell surface expressed LFA-1 I-domains. Panel A, Binding of K562 transfectants to immobilized ICAM-1 in the presence or absence of DTT. Binding was performed in the presence (white bar) or absence (black bar) of DTT. Panel B, Effect of divalent cations on binding of K562 transfectants to ICAM-1. Binding was performed in the presence of $Mn^{2+}$ (black bar), $Mg^{2+}$ (shaded bar) or EDTA (white bar). In Panels A and B, two clones (#1 and #2) of the transfectants expressing the wild-type I-domain or mutant I-domain were tested. Panel C, Effect of LFA-1 blocking antibodies on binding of the K287C/K294C I-domain to ICAM-1. Results are mean±SD of triplicate samples and representative of 3 experiments.

For generating stable K562 transfectants that express the I-domain on the surface, 20 μg of SspI-linearized pcDNA3.1/Hygro(+) containing the sequences encoding the I domain and the PDGFR transmembrane domain was used to transfect K562 cells by electroporation as described above. Transfectants were selected for resistance to 100 μg/ml hygromycin B, and were further subcloned by cell sorting and limiting dilution; clones that expressed similar levels of surface wild-type and mutant I domain-PDGFR were selected for functional studies. Stable cell lines were maintained in RPMI medium 1640 supplemented with 10% FBS and 100 μg/ml hygromycin B. Cell surface expression of the isolated I-domains was determined by flow cytometry using antibody TS1/22 to the I-domain (FIG. 7). Two clones from each transfectant were selected and tested for binding to immobilized ICAM-1, and similar results were obtained with each of the two clones (FIG. 8A). Transfectants that expressed intact wild-type LFA-1 showed low basal binding to ICAM-1. However, cells that expressed the isolated wild-type I-domain and the mutant L289C/K294C I-domain did not bind to ICAM-1. This suggests that the isolated wild-type I-domain alone is not sufficient to mediate strong and stable interaction with ligand (Knorr, R and Dustin, M L (1997) J Exp Med 186:719-730). By contrast, cells that expressed the mutant K287C/K294C I-domain showed strong binding to ICAM-1.

If the constitutive ligand binding activity of mutant K287C/K294C is due to the formation of a disulfide bond between the introduced C287 and C294, disruption of the disulfide bond with a reducing agent would abolish ligand binding ability of the mutant. Accordingly, the transfectants were treated with the reducing agent DTT (10 mM) in L15/FBS containing $Mg^{2+}$ and $Ca^{2+}$, and the ability of transfectants to bind to ICAM-1 was assessed. As shown in FIG. 8A, binding of the cell surface-expressed mutant K287C/K294C I-domain to ICAM-1 who abolished after DTT treatment. By contrast, DTT increased binding of intact wild-type LFA-1, and similar results were observed with intact αIIbβ3 integrin. DTT treatment presumably disrupts disulfide bonds in the intact molecule that constrain the integrin in an inactive conformation. However, DTT treatment did not affect binding of the isolated wild-type I-domain or the mutant L289C/K294C I-domain. Since there is no other no disulfide bond in the LFA-1 I-domain as the I-domain structure reveals, these data strongly suggest that the introduced Cys287 and Cys294 formed a disulfide bridge that constrains the I-domain in a high affinity state.

Figure 8B:
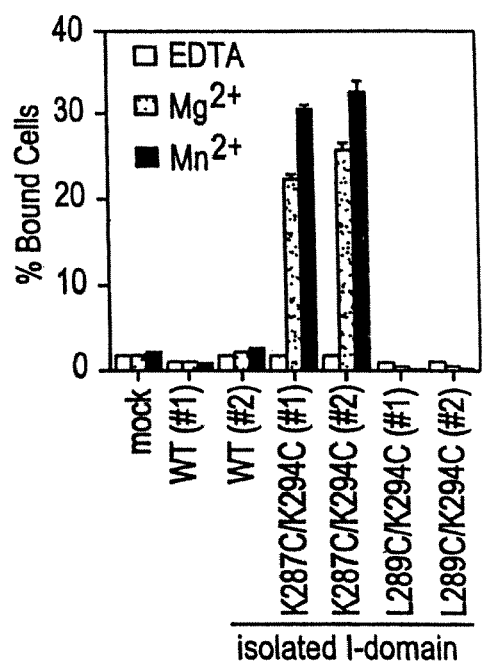

Furthermore, the effect of divalent cations on ligand binding of the isolated I-domains expressed on the surface of K562 transfectants was tested. The binding reactions were performed in HEPES/NaCl/glucose (20 mM HEPES, pH 7.5, 140 mM NaCl, 2 mg/ml glucose) supplemented with 1 mM $Mn^{0.2+}$, 1 mM $Mg^{2+}$, or 1 mM EDTA. As shown in FIG. 8B, the binding of the K287C/K294C I-domain to ICAM-1 was divalent cation dependent, as EDTA treatment abolished the binding. In contrast to intact wild-type LFA-1, $Mn^{2+}$ or $Mg^{2+}$ did not activate ligand binding of the isolated wild-type I-domain or the mutant L289C/K294C I-domain.

Figure 8C:
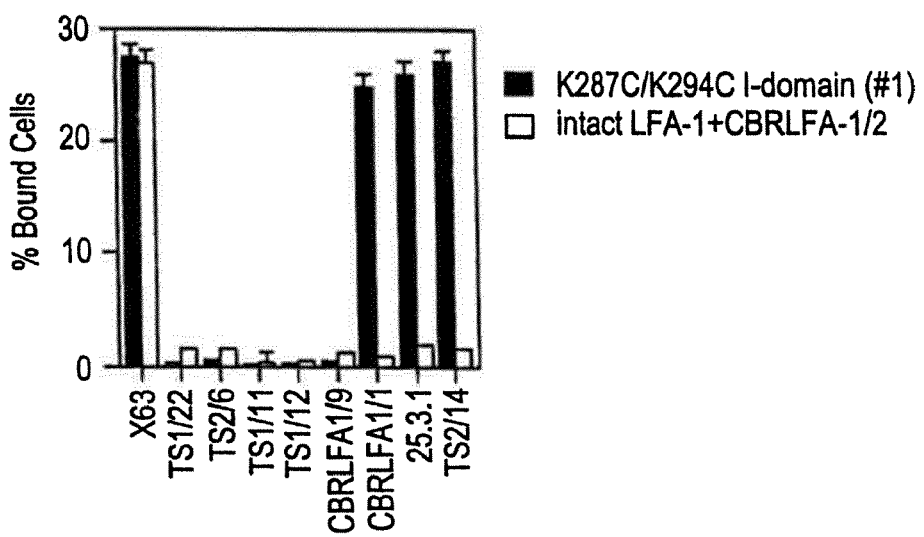
Figure 9A:
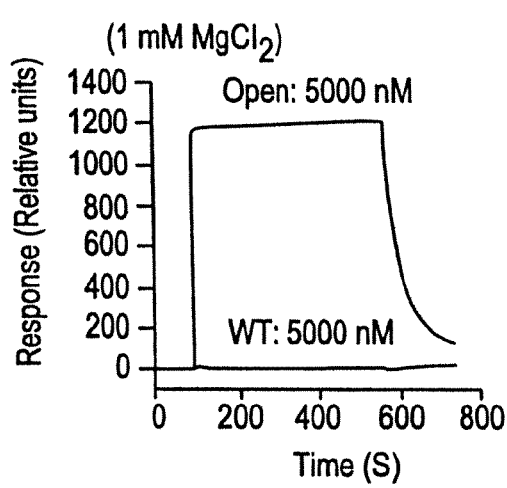
FIG. 9 depicts the surface plasmon resonance sensograms by BIAcore™ recording the interaction of the open (K287C/K294C) or wild-type I-domain with ligands, ICAM-1 (Panels A and B), ICAM-2 (Panels C and D), and ICAM-3 (Panels E and F).
Figure 9B:
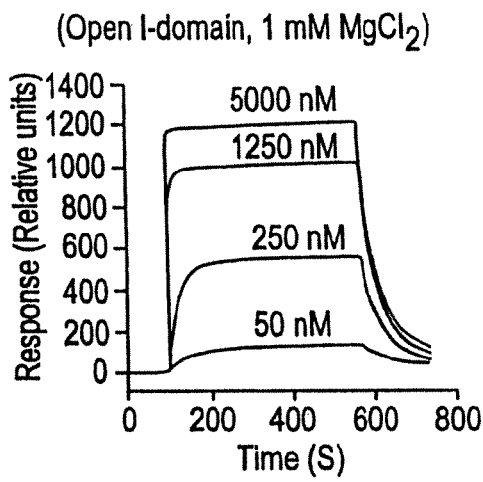
Figure 9C:
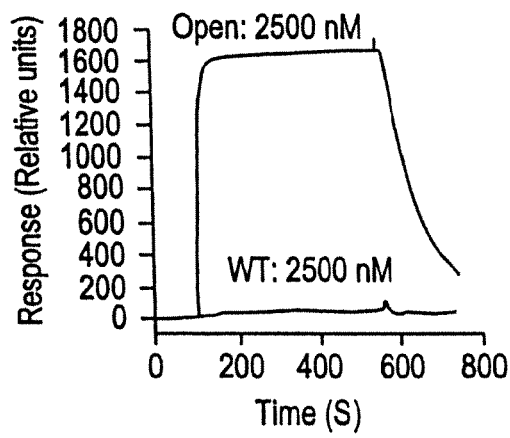
Figure 9D:
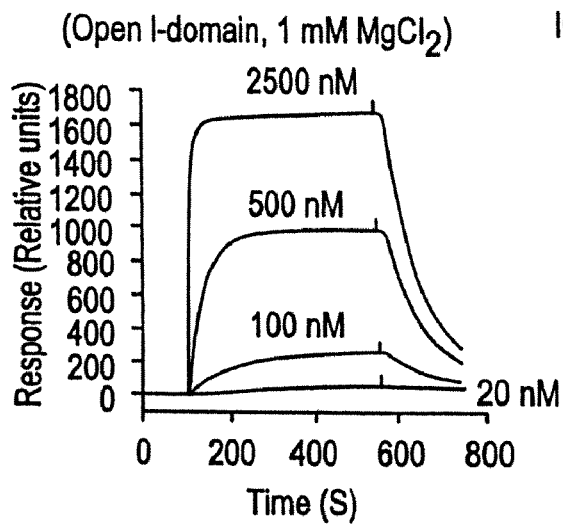
Figure 9E:
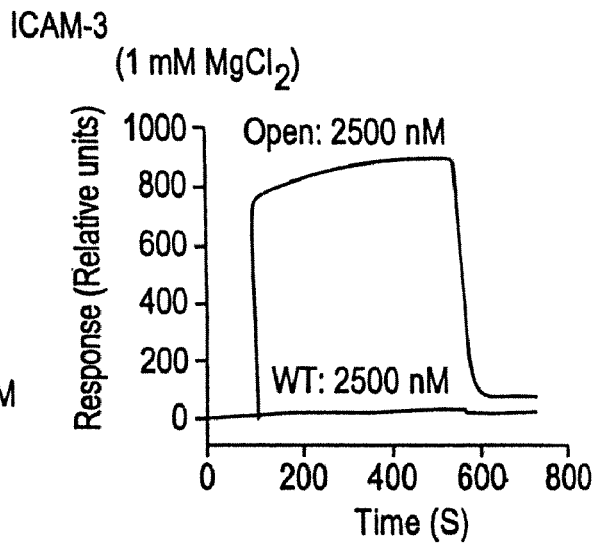
Figure 9F:
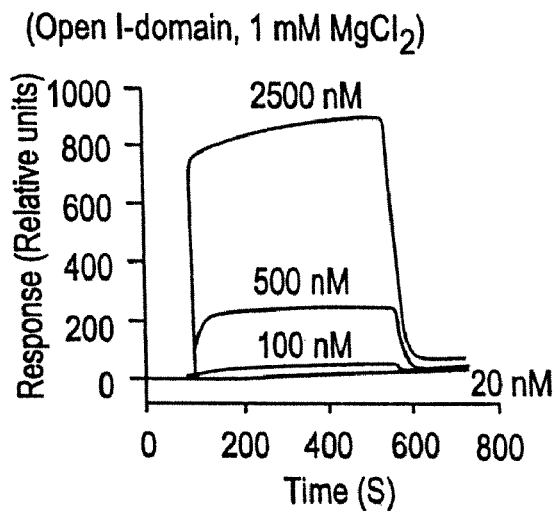

The effect of the I-domain antibodies on ligand binding of the isolated K287C/K294C I-domain was also examined. Transfectants expressing intact LFA-1 were pre-incubated with the activating antibody CBRLFA-1/2, and binding of the cells to ICAM-1 was performed in the presence of the I-domain antibodies TS 1/22, TS2/6, TS1/11, TS11/12, CBRLFA-1/9, CBRLFA-1/, 25.3.1, TS2/14, or the nonbinding antibody X63, as indicated. Monoclonal antibodies TS1/22, TS2/6, TS1/11, TS1/12 and CBRLFA-1/9 inhibited binding of the isolated K287C/K294C I-domain to ICAM-1, whereas antibodies 25-3-1, TS214 and CBRLFA-1/1 did not (FIG. 8C). All antibodies, except for CBRLFA-1/1, bound to the mutant K287C/K294C I-domain as well as the wild-type I-domain as determined by flow cytometry. The binding of CBRLFA-1/1 to the mutant I-domain was reduced to 80% of the wild-type I-domain. These results are consistent with those obtained with the intact LFA-1 K287C/K294C mutant (Tables 2 and 3), and indicate that the isolated K287C/K294C I-domain remains structural integrity as in the intact molecule.

Example 5

Inhibition of LFA-1 Function In Vivo and In Vivo by Soluble I-Domain Mutants

A soluble αL I-domain mutant stabilized in the open conformation by a disulfide bond (K287C/K294C) was made in *E. coli*.

Briefly, recombinant mutant αL I-domain stabilized in the open conformation (K287C/K294C), or recombinant wild-type αL I-domain from amino acid residue G128 to Y307, were cloned into pET11b (Novagen) and expressed in *E. coli* induced with 1 mM IPTG for 4 hours. The recombinant proteins were purified from inclusion bodies by solubilization of inclusion bodies in 6M guanidine HCl and were refolded by dilution in the presence of 0.1 mM $Cu^{2+}$/phenanthrolin to enhance formation of disulfide bonds. Protein was concentrated by ammonium sulfate precipitation, dialyzed, and purified over a monoQ ion-exchange column. To remove any material in which the disulfide bond did not form, free sulfhydryls were reacted with activated biotin and passed over a streptavidin column. The recombinant proteins were then purified by gel filtration and concentrated by Centriprep. For BIAcore™ analysis, recombinant ICAM-1, ICAM-2 and ICAM-3 Fc chimeras were immobilized on the BIAcore™ sensor chip by an amine-coupling method. Recombinant αL I-domains were flowed in, and BIAcore™ assays were performed with Tris-buffered saline supplemented with 1 mM $MgCl_2$ or 2 mM EDTA, at a flow rate of 10 μl/minute at 25° C.

The purified open I-domain showed high affinity to its ligands, ICAM-1, -2, and 3, in the presence of 1 mM $MgCl_2$ as assessed by BIAcore™ analysis, whereas binding of a soluble wild-type I domain was not detectable (FIG. 9, Panels A, C and E; Table 4). The interaction of the open I-domain with ligands was divalent cation-dependent, and was abolished in the presence of 2 mM EDTA, suggesting that the interaction depends on MIDAS. Since the wild-type I-domain showed no interaction with ligands, the open I-domain allowed for the detailed analysis of the binding kinetics of LFA-1 with its ligands. To analyze binding kinetics, different concentrations of open I-domain were tested for ligand binding (FIG. 9, Panels B, D and F). Kinetic analysis demonstrated a fast association rate ($1.28 \times 10^5$ $M^{-1}s^{-1}$) and an intermediate dissociation rate (0.0230 $s^{-1}$) for ICAM-1, the major ligand on endothelial cells (Table 4). The KD for ICAM-1 is in the nanomolar range and ICAM-1 showed the highest affinity, followed by ICAM-2 and ICAM-3. The open I-domain also showed nanomolar range affinity for murine ICAM-1.

TABLE 4

Kinetics of open I-domain binding to ICAMs

| Ligand | $K_{on}$ (M$^{-1}$s$^{-1}$) | $K_{off}$ (s$^{-1}$) | $K_D$ (nM$^{-1}$) |
|---|---|---|---|
| ICAM-1 | $1.28 \times 10^5$ | 0.0230 | 180 |
| ICAM-2 | $0.23 \times 10^5$ | 0.0118 | 513 |
| ICAM-3 | $0.19 \times 10^5$ | 0.0749 | 3942 |

$k_{on}$, $k_{off}$, and $K_D$ were calculated based on 1:1 interaction model using BIAevaluation$_{TM}$ software.

In another study, measurements of the affinity of the recombinant, soluble high affinity αL I domain for its ligand ICAM-1 show a Kd of 200 nM, as assessed by BIAcore. Thus, the isolated, high affinity conformer of the αL I domain is as active as the most activated αLβ2 heterodimer.

Figure 10A:
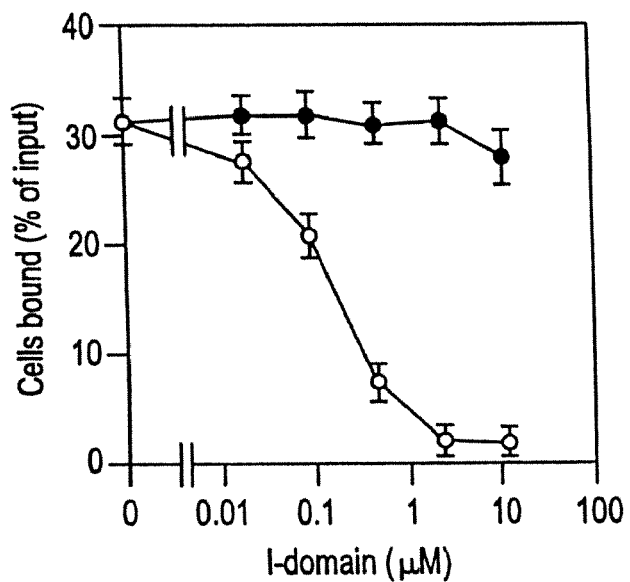
FIG. 10 depicts the inhibition of LFA-1-dependent adhesion in vitro by the open αL I-domain. Panel A depicts the adhesion of K562 stable transfectants expressing wild-type LFA-1 to immobilized ICAM-1 in the presence of soluble wild-type (closed circles) or open (K287C/K294C) I-domain (open circles); Panel B depicts the homotypic aggregation of the murine EL-4 T lymphoma cell line in the presence of soluble wild-type (closed circles) or open (K287C/K294C) I-domain (open circles).

The activity of the soluble open I-domain to inhibit LFA-1I-dependent adhesion was tested. In one study, K562 cells stably expressing wild-type LFA-1 were fluorescently labeled by BCECF and LFA-1 on the cell surface was activated by the activating monoclonal antibody, CBRLFA-1/2 in L15 media supplemented with FCS. The cells were subsequently incubated in ICAM-1 coated 96-well plastic plates in the presence or absence of I-domains. After incubation for 40 minutes at 37° C., unbound cells were washed off on a Microplate Autowasher. The fluorescence content of total input cells and the bound cells in each well was quantitated on a Fluorescent Concentration Analyzer. The bound cells were expressed as a percentage of total input cells per sample well. In contrast to the wild-type I-domain, the open I-domain mutant strongly inhibited adhesion of LFA-1 expressing cells to immobilized ICAM-1 (FIG. 10A).

Figure 10B:
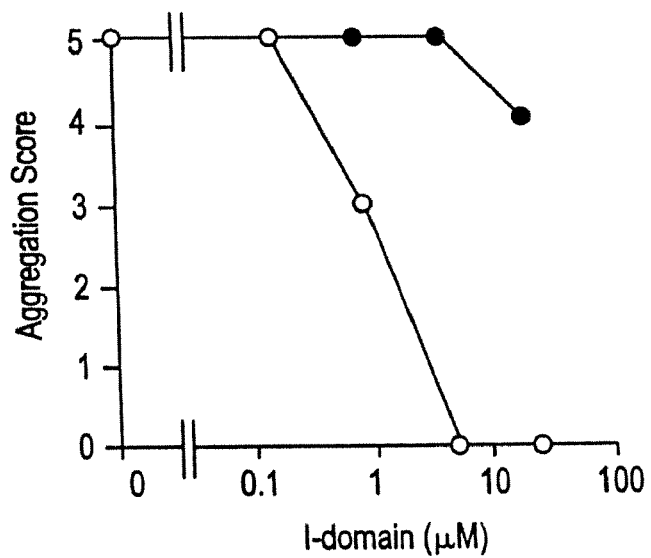

In another study, the murine T lymphoma cell line EL-4 which expresses both murine LFA-1 and its ligands, including murine ICAM-1, and which exhibits LFA-1-dependent homotypic aggregation upon activation by PMA was used. Cells were incubated in a 96 well plate in the presence of 50 ng/ml PMA and varying amounts of soluble I-domains. After incubation for 2 hours at 37° C., 5% $CO_2$, the degree of aggregation was scored under the microscope as follows: 0 indicated that essentially no cells were clustered; 1 indicated that <10% of cells were aggregated; 2 indicated clustering of <50%; 3 indicated that up to 100% of cells were in small, loose aggregates; 4 indicated that nearly 100% of cells were in larger clusters; and 5 indicated that nearly 100% of cells were in very large, tight clusters. As shown in FIG. 10B, the soluble open I-domain also inhibited PMA-induced LFA-1 dependent homotypic aggregation of the murine T-cell line EL-4.

Moreover, the ability of the open I-domain mutants to inhibit LFA-1 function in vivo was tested by visualizing microcirculation in the peripheral lymph node (LN) with intravital microscopy. Briefly, a small bolus (20-50 .mu.l) of LN cell suspensions from T-GFβ mice were retrogradely injected through a femoral artery catheter and visualized in the subiliac LN by fluorescent epi-illumination from a video-triggered xenon arc stroboscope. After recording control TGFβ cell behavior in the absence of 1-domain, the mouse was pretreated by intra-arterial injection of 1-domain (10 .mu.g/g of weight) 5 minutes before T$^{GFP}$ cell injection. All scenes were recorded on videotape and off-line analysis was done. The rolling fraction was calculated as percentage of rolling cells amount the total number of TGFβ cells that entered a venule. The sticking (firm adhesion) fraction was determined as the percentage of T$^{GFP}$ cells becoming firmly adherent for >20 seconds in the number of T$^{GFP}$ cells that rolled in a venule. Results were semi-quantitatively scored as follows: −: 0%, .+−.: 0-5%, +: 5-20%, ++: 20-40%, +++: 40-60%, ++++: 60-80%, +++++:80-100%.

As shown in Table 5, below, injection of the open I-domain but not the wild-type I-domain effectively blocked firm adhesion of T-lymphocytes to high endothelial venules, which is LFA-1-dependent. Lymphocyte rolling that is mediated by L-selectin and PNAd was not compromised, suggesting that the inhibitory effects of the open I-domain was LFA-1 specific.

TABLE 5

In vivo firm adhesion of lymphocytes under flow in peripheral lymph node high endothelial venules was inhibited by open but not wild-type I-domain

| | Fraction | | |
|---|---|---|---|
| I-domain | Rolling | firm adhesion | transmigration |
| None | +++ | ++ | ± |
| wild-type | +++ | ++ | ± |
| Open | ++++ | ± | − |

Kinetics of the Binding of .alpha.L Mutant I-Domains to ICAM-1

To further investigate the kinetics of the interaction of the αL I-domains with ICAM-1, recombinant soluble αL I-domains were expressed in *E. coli*, refolded and purified. As shown in Table 6, below, the affinity of E284C/E301C is nearly comparable to K287C/K294C. The affinity of L161C/F299C, K160C/F299C, and L 161 C/T300C are significantly higher than wild type, but 20-30 times lower than high-affinity open αL I-domain, K287C/K294C. L161C/F299C, K160C/F299C, and L161C/T300C are referred to as intermediate-affinity αL I-domains.

TABLE 6

Kinetics of interaction of αL I-domains with ICAM-1

| αL I-domain | $K_{on}$ (1/Ms) | $K_{off}$ (1/s) | $K_D$ (μM) |
|---|---|---|---|
| Locked open | | | |
| K287C/K294C | $1.28 \times 10^5$ | 0.0230 | 0.180 |
| E284C/E301C | $1.28 \times 10^5$ | 0.0459 | 0.360 |
| L161C/F299C | $1.36 \times 10^5$ | 0.513 | 3.76 |
| K160C/F299C | $1.53 \times 10^5$ | 0.67 | 4.39 |
| L161C/T300C | $1.35 \times 10^5$ | 0.65 | 4.8 |
| WT | $2.22 \times 10^3$ | 3.00 | 1350 |
| Locked closed | | | |
| L289C/K294C | $2.11 \times 10^3$ | 2.84 | 1760 |

Recombinant soluble αL I-domains were expressed in *E. coli*, refolded and purified. Kinetics of binding of the I-domains to ICAM-1 was measured by BIAcore™ instruments. Kinetics was analyzed BIAevaluation™ software.
KD was calculated by Scatchard plots using data at steady states.
Koff was obtained by curve fitting of the dissociation phase using 1:1 binding model.
Kon was calculated by Koff/KD.

Example 6

Construction and Activity of Mac-1 Cysteine Substitution Mutants

A similar approach was taken to design an open, high affinity conformation of Mac-1 by introducing a disulfide bond into the I-domain. The design of Mac-1 cysteine substitution mutants was described in Example 1.

TABLE 7

Cα and Cβ between mutated residues in either open or closed conformation

| Mutations | ido (open conformation) | | jlm (closed conformation) | |
|---|---|---|---|---|
| | Cα | Cβ | Cα | Cβ |
| Locked open | | | | |
| Q163C/Q309C | 8.37 | 6.36 | 9.11 | 7.16 |
| Q298C/N301C | 5.31 | 4.21 | 9.05 | 10.91 |
| D294C/T307C | 9.21 | 8.67 | 16.01 | 17.52 |
| D294C/Q311C | 9.02 | 7.08 | 9.79 | 10.02 |
| F297C/A304C | 6.31 | 3.78 | 11.18 | 10.17 |
| Locked closed | | | | |
| Q163C/R313C | 13.8 | 13.33 | 7.36 | 5.15 |

The distance between wild-type residues was measured by Look .TM. software in open conformation (1ido) or closed conformation (1jlm).

In order to assess the effect of the introduction of pairs of potentially disulfide bond-forming cysteines into the I-domain of αMβ2 on CBRM 1/5 activation-dependent epitope expression and ligand binding, plasmids encoding the wild-type or mutant αM subunits and the β2 subunit were co-transfected into 293T and K562 cells. α.β heterodimer formation was confirmed using monoclonal antibody CBRM1/32 which recognizes an epitope in the putative β-propeller domain of the αM subunit only after association with the β2 subunit, and antibody CBRM1/5 was used to detect integrin activation.

Figure 11A:
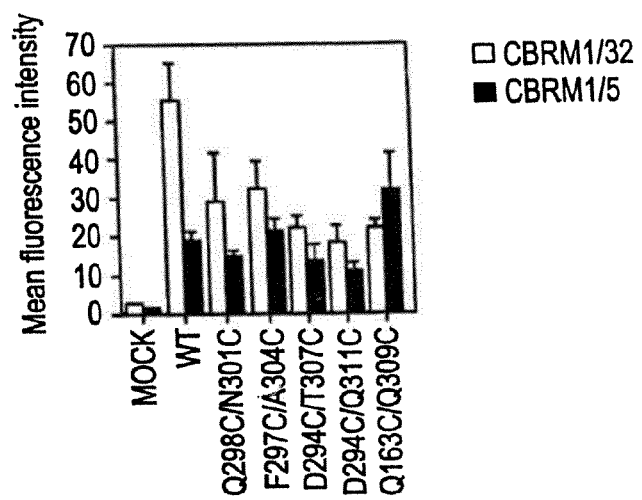
FIG. 11 depicts the expression and ligand binding activity of the Mac-1 cysteine substitution mutants in transiently transfected 293T cells. Panel A, binding of monoclonal antibodies CBRM1/32 (open bars) and CBRM1/5 (black bars) to intact Mac-1 I-domain mutants. Panel B, adhesion of 293T transient transfectants expressing intact Mac-1 cysteine substitution mutants to iC3b coated on plastic. Panel C, adhesion of 293T transient transfectants expressing isolated Mac-1 mutant I-domains to iC3b ligand in the presence (black bars) or absence (open bars) of antibody CBRM1/5.
Figure 11B:
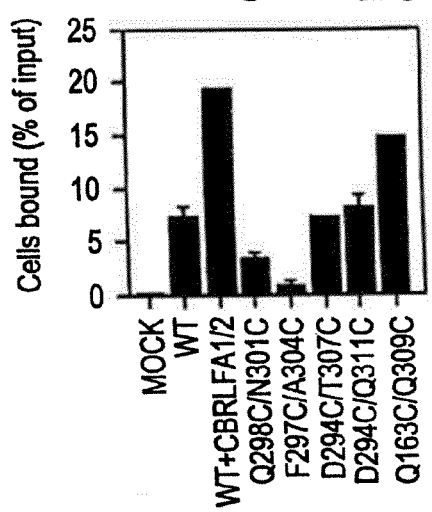
Figure 12A:
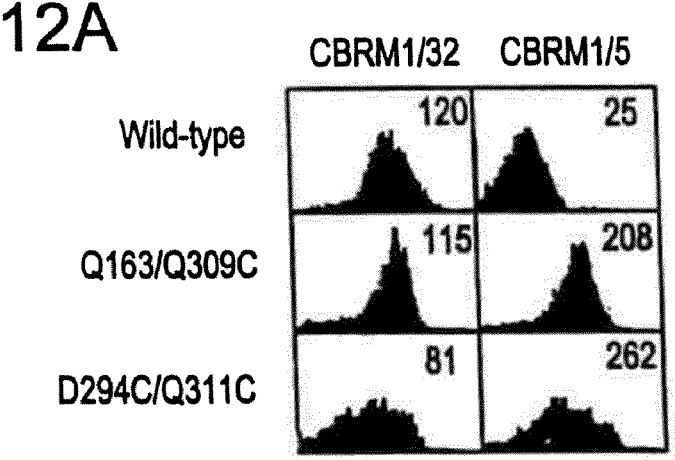
FIG. 12 depicts the expression and ligand binding activity of the Mac-1 cysteine substitution mutants in K562 stable transfectants. Panel A, representative histogram showing binding of monoclonal antibodies CBRM1/32 and CBRM1/5 to intact Mac-1 I-domain mutants as assessed by flow cytometry. Mean fluorescence intensity is indicated in the upper right hand corner of the histogram plot. Panel B, adhesion of K562 stable transfectants expressing intact Mac-1 cysteine substitution mutants to iC3b coated on plastic. Panel C, adhesion of K562 stable transfectants expressing isolated Mac-1 I-mutant I-domains to iC3b ligand. Adhesion was assayed in the presence (black bars) or absence (open bars) of monoclonal antibody CBRM1/5, or in the presence of 10 mM DTT (gray bars).
Figure 12B:
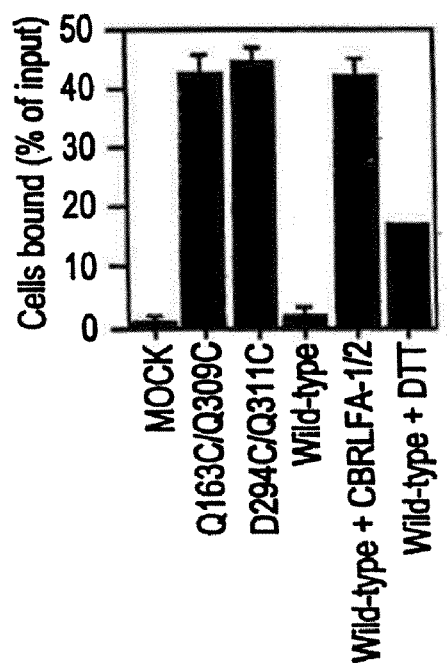

The Q163C/Q309C pair of mutations worked well (FIG. 11B, FIGS. 12B and C). This mutant introduces a putative disulfide bond near the bottom front of the I-domain, between residues that are in the lower one-third of the last α-helix and the first α-helix, and have Cβ carbons that are 6.36.ANG. apart in the 1ido structure. In contrast, the Cβ carbons for the D294C/T307C and D294C/N311C substitutions are 8.67.ANG. and 7.08.ANG. apart, respectively. The Cβ carbons for the Q298C/N301C and F297C/A304C substitutions are within the ideal range, however these substitutions are closer to the loop between the last β-strand and α-helix, and must have unfavorable effects such as distorting the ligand binding site.

When expressed within an intact heterodimer in transiently transfected 293T cells, the Q163C/Q309C mutant is expressed half as well as wild-type as measured by CBRM1/32 antibody, but the ratio of the CBRM1/5 activation-dependent epitope to CBRM1/32 expression is markedly higher (FIG. 11A). In addition, the adhesion of 293T cells expressing the Mac-1 Q163C/Q309C mutant to iC3b coated on plastic, as assayed in L15/FBS medium at room temperature, was higher than wild-type, despite its lower expression (FIG. 11B).

Figure 11C:
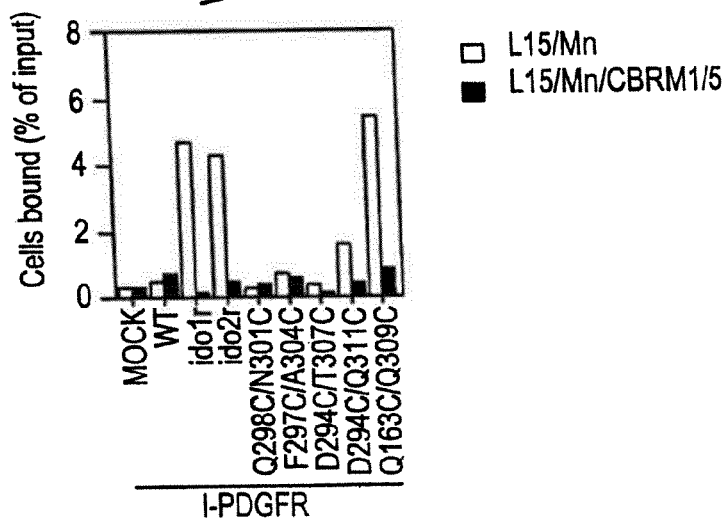

Alternatively, isolated Mac-1 mutant I-domains were expressed on the cell surface in conjunction with an artificial signal sequence and transmembrane domain of the PDGF receptor. Adhesion was assayed in L15/FBS/MnCl$_2$ at 37° C. The isolated wild-type I-domain showed no binding to iC3b, whereas the previously described mutants with computationally redesigned hydrophobic cores, ido1r and ido2r, were active (FIG. 11C) (Shimaoka, M et al. (2000) Nature Structural Biology 7:674-678). The Q163C/Q309C mutant I-domain exhibited strong specific ligand binding that was completely blocked by the inhibitory I-domain monoclonal antibody CBRM1/5 (FIG. 12C).

In a further study, the open I-domain mutants Q 163C/Q309C and D294C/Q311C were stably expressed in K562 cells, and clones expressing the same levels of receptors were selected. Adhesion assays to immobilized iC3b were performed with L15/FBS at 37° C. In contrast to 293T cells, wild-type Mac-1 has little basal activity for ligand binding in these cells (FIGS. 12A and 12B). Both Q163C/Q309C and D294C/Q31 iC showed increased CBRM1/5 activation-dependent epitope expression and increased ligand binding when expressed in an intact αMβ2 heterodimer, as compared to wild-type (FIGS. 12A and 12B). Moreover, K562 cells expressing isolated open I-domain mutants on the cell surface showed strong specific binding to iC3b as compared to wild-type (FIG. 12C).

In order to confirm that the increased ligand binding activity of the open I-domain mutants is induced by the formation of a disulfide bond, the effect of the reducing agent DTT was tested. Binding of αMβ2 transfectants containing mutant I-domains to immobilized iC3b on plastic was tested in the presence and absence of DTT. As summarized in Table 8, below, locked open αM I-domains, (Q163C/Q309C) and (D294C/Q311 C), are active in the absence of activation and their activities are partly reduced by disulfide reduction by DTT. By contrast, locked closed αM I-domain Q163C/R313C is inactive and resistant to activation, but becomes activatable after disulfide reduction by DTT.

Figure 12C:
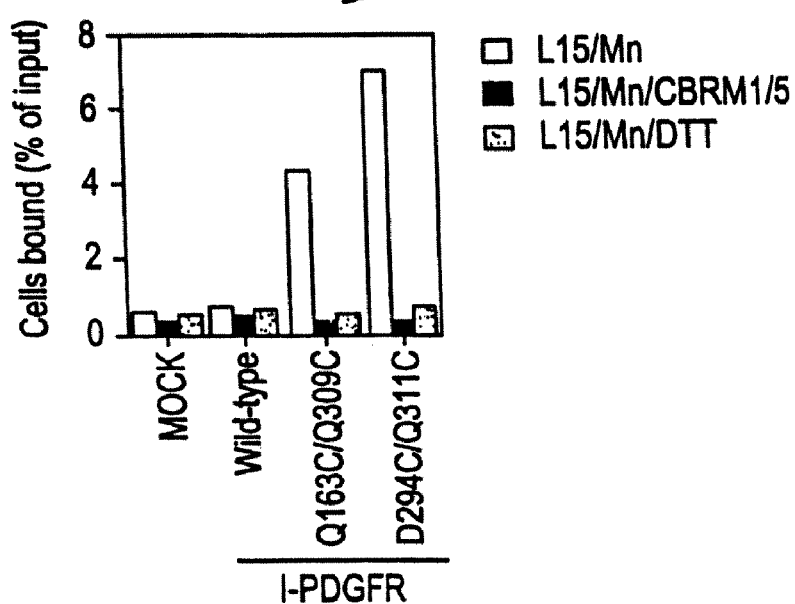

As shown in FIG. 12C, DTT treatment abolished ligand binding by isolated locked open I-domains. In contrast, DTT increased binding of the intact wild-typeαMβ2 (FIG. 2B), indicating that DTT used in this experiment was not toxic and abolishment of ligand binding by the open I-domain mutants was not due to a non-specific effect of DTT. Taken together, these data suggest that the introduced cysteines result in the formation of a disulfide bridge that constrains the Mac-1 I-domain in an open or closed conformation.

TABLE 8

Summary of adhesion assay of αMβ2 transfectant containing mutant I-domains

| mutations | −DTT −activation | −DTT +activation | +DTT −activation | +DTT +activation |
|---|---|---|---|---|
| Wild type | ± | ++++ | ++ | ++++ |
| Locked open | | | | |
| Q163C/Q309C | ++++ | ++++ | ++ | ++++ |
| Q298C/N301C | ± | + | NT | NT |
| D294C/T307C | ± | + | NT | NT |
| D294C/Q311C | ++++ | ++++ | ++ | ++++ |
| F297C/A304C | ± | ++ | NT | NT |
| Locked closed | | | | |
| Q163C/R313C | ± | ± | ++ | +++ |

Binding of αMβ2 transfectants containing mutant I-domains to immobilized iC3b on plastic was tested.
Results were semi-quantitatively scored as follow; .
+−.: 0-5%, +: 5-25%, ++25-50%, +++: 50-75%, ++++: 75-100% of binding by activated wild type transfectant.
NT: not tested
DTT: disulfide reduction by DTT treatment.
+activation: activated by activating mAB CBR LFA-½

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for inhibiting αL-mediated interaction with ICAM-1 in an inflammatory disorder or an autoimmune disease in a subject comprising administering to said subject a therapeutically effective amount of an antibody, or an antigen binding fragment thereof, which selectively binds only to a modified integrin αL I-domain polypeptide of SEQ ID NO:2 stabilized in the open conformation by the substitution K287C/K294C, but not to the modified integrin αL I-domain of SEQ ID NO:2 stabilized in the closed conformation, said mutation is based on the mature form of SEQ ID NO:2, thereby inhibiting αL-mediated interaction with ICAM-1 in a subject.

2. The method of claim 1, wherein the antibody is an LFA-1 antibody, or an antigen binding fragment thereof.

3. The method of claim 1, wherein the subject has treated for an inflammatory disorder.

4. The method of claim 1, where in the subject has is an autoimmune disorder.

5. The method of claim 1, wherein the antibody, or antigen binding fragment thereof, is a humanized antibody.

6. The method of claim 1, wherein the antibody, or antigen binding fragment thereof, is a chimeric antibody.

7. The method of claim 1, wherein the antibody, or antigen binding fragment thereof, is a monoclonal antibody.

8. The method of claim 1, wherein the antibody, or antigen binding fragment thereof, is a recombinant antibody.

* * * * *

UNITED STATES PATENT AND TRADEMARK OFFICE
CERTIFICATE OF CORRECTION

| | | |
|---|---|---|
| PATENT NO. | : 8,241,627 B2 | Page 1 of 1 |
| APPLICATION NO. | : 13/165873 | |
| DATED | : August 14, 2012 | |
| INVENTOR(S) | : Timothy A. Springer et al. | |

It is certified that error appears in the above-identified patent and that said Letters Patent is hereby corrected as shown below:

Claim 3, column 82, lines 1-2, delete "treated for";

Claim 4, column 82, line 3, delete "where in" and insert therefor -- wherein --; and Claim 4, column 82, line 3, delete "is".

Signed and Sealed this
Sixteenth Day of October, 2012

David J. Kappos
*Director of the United States Patent and Trademark Office*